US008455629B2

(12) United States Patent
Boyle et al.

(10) Patent No.: US 8,455,629 B2
(45) Date of Patent: Jun. 4, 2013

(54) HUMAN ANTI-OPGL NEUTRALIZING ANTIBODIES AS SELECTIVE OPGL PATHWAY INHIBITORS

(75) Inventors: William J. Boyle, Malibu, CA (US); Eugene Medlock, Westlake, CA (US); John K. Sullivan, Newbury Park, CA (US); Robin L. Elliott, Newbury Park, CA (US); Frank Martin, Newbury Park, CA (US); Haichun Huang, Fremont Park, CA (US)

(73) Assignees: Amgen Inc., Thousand Oaks, CA (US); Medarex, Inc., Princeton, NJ (US)

( * ) Notice: Subject to any disclaimer, the term of this patent is extended or adjusted under 35 U.S.C. 154(b) by 17 days.

(21) Appl. No.: 13/360,454

(22) Filed: Jan. 27, 2012

(65) Prior Publication Data

US 2012/0156725 A1 Jun. 21, 2012

Related U.S. Application Data

(63) Continuation of application No. 12/705,962, filed on Feb. 15, 2010, now abandoned, which is a continuation of application No. 10/408,901, filed on Apr. 7, 2003, now Pat. No. 7,718,776.

(60) Provisional application No. 60/370,407, filed on Apr. 5, 2002.

(51) Int. Cl.
*C07H 21/04* (2006.01)
*C12P 21/02* (2006.01)
*C12P 21/08* (2006.01)
*C12N 5/16* (2006.01)

(52) U.S. Cl.
USPC ..... 536/23.53; 536/23.1; 536/23.5; 435/69.1; 435/69.6; 435/70.21; 435/326; 435/335

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,179,337 A | 12/1979 | Davis et al. | |
| 4,399,216 A | 8/1983 | Axel et al. | |
| 4,474,893 A | 10/1984 | Reading | |
| 4,699,880 A | 10/1987 | Goldstein | |
| 4,710,457 A | 12/1987 | Dupont et al. | |
| 4,710,473 A | 12/1987 | Morris | |
| 4,740,461 A | 4/1988 | Kaufman | |
| 4,816,567 A | 3/1989 | Cabilly et al. | |
| 4,892,538 A | 1/1990 | Aebischer et al. | |
| 4,912,040 A | 3/1990 | Kaufman et al. | |
| 4,946,778 A | 8/1990 | Ladner et al. | |
| 4,959,314 A | 9/1990 | Mark et al. | |
| 4,959,455 A | 9/1990 | Clark et al. | |
| 5,011,472 A | 4/1991 | Aebischer et al. | |
| 5,106,627 A | 4/1992 | Aebischer et al. | |
| 5,118,667 A | 6/1992 | Adams et al. | |
| 5,151,510 A | 9/1992 | Stec et al. | |
| 5,234,784 A | 8/1993 | Aslam et al. | |
| 5,260,203 A | 11/1993 | Ladner et al. | |
| 5,393,739 A | 2/1995 | Bentz et al. | |
| 5,447,851 A | 9/1995 | Beutler et al. | |
| 5,457,035 A | 10/1995 | Baum et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,578,569 A | 11/1996 | Tam | |
| 5,585,089 A | 12/1996 | Queen et al. | |
| 5,585,479 A | 12/1996 | Hoke et al. | |
| 5,599,708 A | 2/1997 | Mundy et al. | |
| 5,625,126 A | 4/1997 | Lonberg et al. | |
| 5,625,825 A | 4/1997 | Rostoker et al. | |
| 5,633,425 A | 5/1997 | Lonberg et al. | |
| 5,641,747 A | 6/1997 | Popoff et al. | |
| 5,658,756 A | 8/1997 | Rodan et al. | |
| 5,661,016 A | 8/1997 | Lonberg et al. | |
| 5,693,761 A | 12/1997 | Queen et al. | |
| 5,693,762 A | 12/1997 | Queen et al. | |
| 5,763,223 A | 6/1998 | Wiley et al. | |
| 5,770,429 A | 6/1998 | Lonberg et al. | |
| 5,789,650 A | 8/1998 | Lonberg et al. | |
| 5,814,318 A | 9/1998 | Lonberg et al. | |
| 5,843,678 A | 12/1998 | Boyle | |
| 5,843,901 A | 12/1998 | Roeske | |
| 5,874,299 A | 2/1999 | Lonberg et al. | |
| 5,877,397 A | 3/1999 | Lonberg et al. | |

(Continued)

FOREIGN PATENT DOCUMENTS

AU 56180/98 B2 7/1998
AU 68518/98 11/1998

(Continued)

OTHER PUBLICATIONS

Adams et al., "Complementary DNA Sequencing: Expresses Sequence Tags and Human Genome Project", Science, 252: 1651-1656 (1991).
Anderson et al., "A homologue of the TNF receptor and its ligand enhance T-cell growth and dendritic-cell function", Nature, 390: 175-179 (1997).
Benjamini et al., Immunology: A Short Course, 2nd edition, Wiley-Liss, New York, p. 40.
Bugress, T. C., et al., "The ligand for osteoprotegrin (OPGL) directly activates mature osteoclasts." J. Cell Bio., 145:527-38 (1999).
Chambers et al., "Generation of osteocast-inductive and osteoclastogenic cell lines fom the H-2KbtsA58 transgenic mouse", Proceedings of the National Academy of Sciences of USA, 90:5578-5582 (1993).

(Continued)

*Primary Examiner* — Xiaozhen Xie
(74) *Attorney, Agent, or Firm* — McDonnell Boehnen Hulbert & Berghoff LLP

(57) ABSTRACT

Monoclonal antibodies and hybridomas producing them that interact with osteoprotegerin ligand (OPGL) are provided. Methods of treating osteopenic disorders by administering a pharmaceutically effective amount of antibodies to OPGL are also provided. Methods of detecting the amount of OPGL in a sample using antibodies to OPGL are further provided.

18 Claims, 26 Drawing Sheets

U.S. PATENT DOCUMENTS

| | | | |
|---|---|---|---|
| 5,961,974 A | 10/1999 | Armitage et al. | |
| 5,981,220 A | 11/1999 | Ni et al. | |
| 5,985,832 A | 11/1999 | Roodman et al. | |
| 6,015,938 A | 1/2000 | Boyle et al. | |
| 6,017,729 A | 1/2000 | Anderson et al. | |
| 6,046,048 A | 4/2000 | Ashkenazi et al. | |
| 6,087,555 A | 7/2000 | Dunstan et al. | |
| 6,180,370 B1 | 1/2001 | Queen et al. | |
| 6,242,213 B1 * | 6/2001 | Anderson | 435/69.1 |
| 6,242,586 B1 | 6/2001 | Gorman et al. | |
| 6,248,516 B1 | 6/2001 | Winter et al. | |
| 6,271,349 B1 | 8/2001 | Dougall et al. | |
| 6,284,485 B1 | 9/2001 | Boyle et al. | |
| 6,284,728 B1 | 9/2001 | Boyle et al. | |
| 6,284,740 B1 | 9/2001 | Boyle et al. | |
| 6,288,032 B1 | 9/2001 | Boyle et al. | |
| 6,316,408 B1 | 11/2001 | Boyle et al. | |
| 6,369,027 B1 | 4/2002 | Boyle et al. | |
| 6,410,516 B1 | 6/2002 | Baltimore et al. | |
| 6,419,929 B1 | 7/2002 | Anderson | |
| 6,479,635 B1 | 11/2002 | Anderson | |
| 6,525,180 B1 | 2/2003 | Gorman et al. | |
| 6,528,482 B1 | 3/2003 | Anderson et al. | |
| 6,537,763 B2 | 3/2003 | Dougall et al. | |
| 6,562,948 B2 | 5/2003 | Anderson | |
| 6,569,430 B1 | 5/2003 | Waldmann et al. | |
| 6,645,500 B1 * | 11/2003 | Halkier et al. | 424/185.1 |
| 6,649,164 B2 | 11/2003 | Maraskovsky | |
| 6,740,522 B2 | 5/2004 | Anderson et al. | |
| 6,838,262 B1 | 1/2005 | Anderson | |
| 6,884,598 B2 | 4/2005 | Dougall | |
| 7,084,257 B2 | 8/2006 | Deshpande et al. | |
| 7,097,834 B1 | 8/2006 | Boyle | |
| 7,192,718 B2 | 3/2007 | Yamaguchi et al. | |
| 7,262,274 B2 | 8/2007 | Anderson et al. | |
| 7,364,736 B2 | 4/2008 | Boyle et al. | |
| 7,411,050 B2 | 8/2008 | Anderson | |
| 7,449,185 B2 | 11/2008 | Yamaguchi | |
| 7,527,790 B2 | 5/2009 | Yamaguchi | |
| 7,572,594 B2 | 8/2009 | Dougall | |
| 7,744,886 B2 | 6/2010 | Anderson | |
| 7,923,008 B2 | 4/2011 | Boyle | |
| 8,058,418 B2 | 11/2011 | Boyle et al. | |
| 2002/0081720 A1 | 6/2002 | Dougall et al. | |
| 2002/0086312 A1 | 7/2002 | Dougall et al. | |
| 2002/0086826 A1 | 7/2002 | Anderson et al. | |
| 2002/0086827 A1 | 7/2002 | Anderson | |
| 2002/0127637 A1 | 9/2002 | Ni et al. | |
| 2002/0150989 A1 | 10/2002 | Greene et al. | |
| 2002/0169117 A1 | 11/2002 | Maraskovsky | |
| 2003/0017151 A1 | 1/2003 | Dougall et al. | |
| 2003/0021785 A1 | 1/2003 | Dougall et al. | |
| 2003/0100069 A1 | 5/2003 | Ni et al. | |
| 2003/0100488 A1 | 5/2003 | Boyle | |
| 2003/0103978 A1 | 6/2003 | Desphpande et al. | |
| 2003/0104485 A1 | 6/2003 | Boyle | |
| 2003/0144480 A1 | 7/2003 | Gorman et al. | |
| 2003/0166097 A1 | 9/2003 | Greene et al. | |
| 2003/0175840 A1 | 9/2003 | Anderson et al. | |
| 2003/0176647 A1 | 9/2003 | Yamaguchi et al. | |
| 2003/0208045 A1 | 11/2003 | Yamaguchi et al. | |
| 2004/0033535 A1 | 2/2004 | Boyle et al. | |
| 2005/0003391 A1 | 1/2005 | Anderson | |
| 2005/0003400 A1 | 1/2005 | Boyle | |
| 2005/0003457 A1 | 1/2005 | Yamaguchi et al. | |
| 2005/0196801 A1 | 9/2005 | Dougall et al. | |
| 2005/0208580 A1 | 9/2005 | Yamaguchi | |
| 2006/0246064 A1 | 11/2006 | Boyle | |
| 2007/0009520 A1 | 1/2007 | Yamaguchi | |
| 2008/0009014 A1 | 1/2008 | Anderson | |
| 2008/0187540 A9 | 8/2008 | Yamaguchi | |
| 2009/0004196 A1 | 1/2009 | Anderson | |
| 2009/0017033 A1 | 1/2009 | Anderson | |
| 2010/0209435 A1 | 8/2010 | Boyle et al. | |
| 2011/0052604 A1 | 3/2011 | Boyle et al. | |

FOREIGN PATENT DOCUMENTS

| | | |
|---|---|---|
| AU | 71205/98 B2 | 11/1998 |
| AU | 713471 | 12/1999 |
| AU | 735355 | 7/2001 |
| AU | 7432574 | 1/2002 |
| EP | 0 036 676 | 9/1981 |
| EP | 0 058 481 | 8/1982 |
| EP | 0 088 046 | 9/1983 |
| EP | 0133988 | 3/1985 |
| EP | 0 143 949 | 6/1985 |
| EP | 0 154 316 | 9/1985 |
| EP | 0514130 A2 | 11/1992 |
| EP | 0526905 A2 | 2/1993 |
| EP | 0727211 A1 | 8/1996 |
| EP | 0 873 998 | 10/1998 |
| EP | 0874045 A1 | 10/1998 |
| EP | 0911342 A1 | 4/1999 |
| EP | 1257648 | 5/2005 |
| JP | 11009269 | 1/1999 |
| NZ | 330400 | 5/1999 |
| WO | 86/00922 A1 | 2/1986 |
| WO | WO 88/01649 | 3/1988 |
| WO | 89/01555 | 2/1989 |
| WO | 89/11540 | 11/1989 |
| WO | 90/14363 A1 | 11/1990 |
| WO | 91/10425 | 7/1991 |
| WO | WO 92/03918 | 3/1992 |
| WO | WO 92/22646 | 12/1992 |
| WO | 93/12227 A1 | 6/1993 |
| WO | 93/15722 | 8/1993 |
| WO | WO 93/15722 | 8/1993 |
| WO | 93/21946 A1 | 11/1993 |
| WO | 94/20069 | 9/1994 |
| WO | WO 94/20069 | 9/1994 |
| WO | 95/11308 A1 | 4/1995 |
| WO | 96/14328 | 5/1996 |
| WO | 96/26217 A1 | 8/1996 |
| WO | 96/28546 A1 | 9/1996 |
| WO | 96/34095 | 10/1996 |
| WO | 97/00317 A1 | 1/1997 |
| WO | 97/00318 A1 | 1/1997 |
| WO | 97/01633 | 1/1997 |
| WO | 97/23614 A1 | 7/1997 |
| WO | 98/01555 | 1/1998 |
| WO | 98/07840 A1 | 2/1998 |
| WO | 98/24893 | 6/1998 |
| WO | 98/25958 A2 | 6/1998 |
| WO | WO 98/24884 | 6/1998 |
| WO | 98/28246 A1 | 7/1998 |
| WO | 98/28423 | 7/1998 |
| WO | 98/28424 A2 | 7/1998 |
| WO | 98/28426 A2 | 7/1998 |
| WO | 98/46644 A1 | 10/1998 |
| WO | 98/46751 A1 | 10/1998 |
| WO | 98/49305 A1 | 11/1998 |
| WO | 98/54201 A1 | 12/1998 |
| WO | 99/19468 A1 | 4/1999 |
| WO | 99/29865 | 6/1999 |
| WO | 99/53942 A1 | 10/1999 |
| WO | 99/58674 A2 | 11/1999 |
| WO | 99/65495 | 12/1999 |
| WO | 99/65499 | 12/1999 |
| WO | 00/15807 | 3/2000 |
| WO | WO 00/24782 | 5/2000 |
| WO | 01/03719 A2 | 1/2001 |
| WO | WO 01/09187 | 2/2001 |
| WO | 01/17543 A2 | 3/2001 |
| WO | 01/18203 A1 | 3/2001 |
| WO | 01/23549 | 4/2001 |
| WO | 01 62932 | 8/2001 |
| WO | 02/15846 | 2/2002 |
| WO | 02/16551 | 2/2002 |
| WO | 03/002713 A2 | 9/2003 |

OTHER PUBLICATIONS

Chambers, T.J., "Regulation of the differentiation and function of osteoclasts." J. Pathol. 192:4-13 (2000).

Chenu et al., "Transforming growth factor β inhibits formation of osteoclast-like cells in long-term human marrow cells." Proceed. of the National Acad. of Science of USA, vol. 90, Jun. 1993, pp. 5578-5532.
Database GenEMBL, EMBL Accession No. AF019048, Nov. 19, 1996.
Database GenBank, Accession No. AB008426.
Database GenBank, Accession No. AF019047.
Database GenBank, Accession No. AF013170.
Database GenBank, Accession No. AF013171.
Database GenBank, Accession No. AF019048.
Fata, J. E., et al., "The osteoclast differentiation factor osteoprotegerin-ligand is essential for mamary glad development." Cell 103:41-50 (2000).
Faust, J., et al., "Osteoclast markers accumulate on cells developing from human peripheral blood monomuclear precursors." J. Cell Biochem. 72:67-80 (1999).
Fawtrop et al. "The Effect of Transforming Growth Factor β on the Plasminogen Activator Activity of Normal Osteoblask-like Cells and a Human Osteosarcoma Cell Line MG-63", Journal of Bone and Mineral Research, 7 (12):1383-1371 (1992).
Fenton et al. "Long-Term Culture of Disaggregated Rat Osteclasts: Inhibition of Bone Resorpton and Reduction of Osteoclast-like Cell Number by Calcitonin and PTHrP[107-139]", Journal of Cellular Physiology, 155:1-7 (1993).
Fuller, K., et al., "TRANCE is necessary and sufficient for osteoblast-mediated activation of bone resorportion in osteoclasts." J. Exp. Med., 188:997-1001 (Sep. 7, 1998).
Gao, Y. H., et al., "Potential role of cbfa1, an essentail transcriptional factor for osteoblast differentiation, in osteoclastogenesis: regulation of mRNA espression ofosteoclast differentiation factor (ODF)." Biochem. Biophys. Res. Commun. 252:697-702 (1998).
Geroge et al., "Macromolecular Sequencing and Synthesis", edited by David Schlesinger, Alan R. Loss. Inc., New York, pp. 127-149, (1988).
Goodwin et al., "Molecular Cloning and Expression of the Type 1 and Type 2 Murine Receptors for Tumor Necrosis Factor", Molecular and Cellular Biology,11(6):3020-3026 (1991).
Gowen et al., "Preferential Inhibition of Cytokine-Stumulated Bone Resorption by Reconbinant Interferon Gamma", Journal of Bone and Mineral Research, 1(5):469-474 (1986).
Greenfield, E. M., et al., "Regulation of osteocast activity." Life Sci. 65:1087-102 (1999).
Hattersley et al., "Hyman Macrophage Colony-Stimulating Factor Inhibits Bone Resorption by Osteclasts Disaggregated From Rat Bone", Journal of Cellular Physiology,137:199-203 (1988).
Hsu, H., et al., "Tumor necrosis factor receptor family member RANK mediates osteoclast differentiation and activation induced by osteoprotegrin lignad". Poc. Natl. Acad. Sci. USA 96:3540-5 (1999).
International Search Report, International Application No. PCTJP98/10728 (1998).
Itonaga, I., et al., "Rheumatiod arthritis synovial macrophage-osteoclast differentiation is osteoprotegrin ligand-dependent," J. Pathol. 192:97-104 (2000).
Kaji et al., "Insulin-Like Growth Factor-I Medicates Osteoclast-Like Cell Formation Stimulated by Parathyroid Hormone", Journal of Cellular Physiology,172:55-62 (1997).
Kasona et al., "Inhibitory Effect of Interleukin-4 on Osteoclast-Like Cell Formation in Mouse Bone Marrow Culture", Bone and Mineral, 21(3):179-188 (1993).
Kim, D., et al., "Regulation of peripheral lumph node genesis by the tumor necrosis factor family member TRANCE." J. Exp. Med. 192:1467-78 (2000).
Kim, Nacksung, et al., "Diverse roles of the tumor necrosis factor family member TRANCE in skeletal physiology revealed by TRANCE deficiency and partial rescue by a lymphocyte-expresses TRANCE trangene." Proc. Natl. Acad. Sci. USA 97:10905-10 (2000).
Kinpara, K., et al., "Osteoclast differentiation factor in human osteosarcoma cell line." J. Immunoassay 21:327-40 (2000).
Kitazawa, R., et al., "Promoter structure of mouse RANKL/TRANCE/ODF gene," Biochim. Biophys. Acta 1445:134-41 (1999).

Kong, Y. Y. et al., "Activated T cells regulate bone loss and joing destruction in adjuvant arthritis through osteoprotegrin ligand." Nature 402:304-9 (1999).
Kong, Y. Y. and J. M. Penninger, "Molecular control of bone remodeling and osteoporosis." Exp. Gerontol. 35:947-56 (2000).
Kukita et al., "Osteoinductive Factor Inhibits Formation of Human Osteoclast-Like Cells", Proceedings of the National Academy of Sciences of USA, 87:3023-3026 (1990).
Lacey et al., "Osteoprotegrin ligand is a cytokine that regulates osteoclast differentiation and activation", Cell 93:165-75 (Apr. 17, 1998).
Lacey et al., "Osteoprotegrin ligand modulates murine osteoclast survival in vitro and in vivo." Am J. Pathol.157:435-48 (2000).
Lewis et al., "Cloning and Expression of cDNAs for Two Distinct Murine Tumor Necrosis Factor Receptors Demonstrate One Receptor in Species Specific", Proceedings of the National Academy of Sciences of USA, 88:2830-2834 (1991).
Nakagawa, N., et al., "RANK is the essential signaling receptor for osteoclast differentiation factor in osteoclastogenesis." Biochem, Biophys. Res. Commun. 253:395-400 (1998).
O'Brien, E. A., et al., "Osteoprotegrin ligand regulates osteoclast adherence to the bone surface in mouse calvaria." Biochem, Bopphys. Res. Commun. 274:281-90 (2000).
Oyajobi et al., "Therapeutic efficacy of a soluble receptor activator of nuclear factor kappa-B-IgG Fc Fusion Protien in suppressing Bone resorption and hypercalcemia in a model of humoral hyperclacemia of malignancy", Cancer Res., vol. 61:2572-78 (Mar. 15, 2001).
Peterson et al., "AMG162, A Fully Human Monoclonal Antibody Against Receptor Activator of NF-Kappa B Ligand (RANKL), Repidly and Profoundly Suppresses Bone Resorption in Cunomolgus Monkey", International Bone and Mineral Society—Japan Bone and Mineral Society, 2003, Poster Session 2 "Osteoclasts", Osaka, Japan (Jun. 6, 2003).
Reddi, A. H. "Bone Morphogenesis and Modeling: Soluble Signals Sculpt Osteosomes in the Solid State", Cell, 89:151-161 (1997).
Reiger et al., Glossary of Genetics and Cytogenetics, p. 17, Springer-Verlag Berlin Heidlberg, New York (1976).
Shalhoub, V., et al., "Osteoprotegrin and osteoprotegrin ligand effects on osteoclast formation for human peripheral blood mononuclear cell precursors," J. Cell Biochem. 72:251-61 (1999).
Simonet et al., "Osteoprotegrin: A Novel Secreted Protein Involved in the Regulation of Bone Density", Cell, 89:309-319 (1997).
Smith et al., "The TNF Receptor Superfamily of Cellular and Viral Proteins: Activation, Costimulation, and Death", Cell, 76:959-962 (1994).
Suda et al., "Modulation of Osteoclast Differentation by Local Factors", Bone, 17(2 Suppl):87S-91S (1995).
Suda, T., et al., "Modulation of osteoclast differentiation and function by the new members of the tumor necrosis factor receptor and ligand familes." Endocr. Rev. 20:345-57 (1999).
Takada et al., "A Simple Method to Assess Osteoclast-Mediated Bone Resorption Using Unfractionated Bone Cells", Bone and Mineral, 17:347-359 (1992).
Takahasi, N., et al., "A new member of tumor necrosis factor ligand family, ODF/OPGL/GRANCE/RANKL, regulates osteoclast differentiation and function." Biochem. Biophys. Res. Commun. 256:449-55 (1999).
Takeyama, S., et al., "Low calcium environment effects osteoprotegrin ligand/osteoclast differentiation factor." Biochim. Biophys. Res. Commun. 276:524-9 (2000).
Teng, Y. A., et al., "Functional human T-cell immunity and osteoprotegrin ligand control alveolar bone destruction in periodontal infection." J. Clin. Invest. 106:749-52 (2000).
Tsuda et al., "Isolation of a Novel Cutokine From Human Fibroblasts That Specifically Inhibits Osteoclastogenesis", Biochemical and Biophysical Research Communications, 234(1):137-142 (1997).
Udagawa, N., et al., "Osteoblsts/stromal cells stimulate osteoclast activation through expression of osteoclast differentiation factor/RANKL but no macrophage colony-stimulating factos." Bone 25:517-23 (1999).
Wantable et al., "Interlukin-4 as a Potent Inhibitor of Bone Resorption" Biochemical and Biophysical Research Communications, 172(3):1035-1041 (1990).

Willard, D. et al., "Expression, purification, and characterization of the human receptor activator of NF-kappaB ligand (RANKL) extracellular domain." Protein Expr. Purif. 20:48-57 (2000).
Wong et al., "TRANCE is a Novel Ligand of the Tumor Necrosis Factor Receptor Family That Activates c-Jun N-terminal Kinase in T Cells", Journal of Biological Chemistry, 272(40):25190-25194 (1997).
Wong et al., "TRANCE (Tumor Necroses Factor [TNF]-related Activation-induced Sytokine), a New TNF Family Member Predominantly Expressed in T Cells, Is Dendritic Cell-Specific Survival Factor", J. Exp. Med. 186:2075-80 (1997).
Yasuda et al., "Osteoclast differentiation factor is aligand for osteoprotegrin/osteoclastogenesis-inhibitory and is identical to TRANCE/RANKL." Proc. Natl. Acad. Sci. USA, 95:3597-3602 (Mar. 1998).
Yoneda et al., "Suramin Suppesses Hypercalcemia and Osteoclastic Bone Resoption in Nude Mice Bearing a Human Squamous Cancer", Cancer Research, 55:1989-1993 (1995).
Zhang et al., "Tumor necrosis factor-alpha (TNF) stimulates RANKL-induced ostepclastogenesis via coupling of TNF tyoe I receptor and RANK signaling pathways." J. Biol. Chem., vol. 276(1):563-68 (Jan. 5, 2001).
Marks et al., By-passing immunization: building high affinity human antibodies by chain shuffling, Biotechnology, 10(7): 779-783 (1992).
Marston et al., Solubilization of protein aggregates, Meth. Enz., 182: 264-276 (1990).
Mason et al., The hypogonadal mouse: reproductive functions restored by gene therapy, Science, 234: 1372-1378 (1986).
Merrifield et al., Solid Phase Peptide Synthesis. I. The Synthesis of a Tetrapeptide, J. Am. Chem. Soc., 85(14): 2149-2154 (1963).
Morrison et al., Research Articles: Chimeric human antibody molecules: mouse antigen-binding domains with human constant region domains, PNAS USA, 81: 6851-6855 (1984).
Muller, Determination of affinity and specificity of anti-hapten antibodies by competitive radioimmunoassay, Meth. Enzymol., 92: 589-601 (1983).
Neuberger et al., Recombinant antibodies possessing novel effector functions, Nature, 312(5995): 604-608 (1984).
Ornitz et al., Elastase I Promoter Directs Expression of Human Growth Hormone and SV40 T Antigen Genes to Pancreatic Acinar Cells in Transgenic Mice, Cold Spring Harbor Symposium Quantitative Biology, 50: 399-409 (1985).
Pinkert et al., Research Papers: An albumin enhancer located 10 kb upstream functions along with its promoter to direct efficient, liver-specific expression in transgenic mice, Genes and Devel., 1: 268-276 (1987).
Readhead et al., Expression of a myelin basic protein gene in transgenic shiverer mice: correction of the dysmyelinating phenotype, Cell, 48(4): 703-712 (1987).
Riechmann et al., Reshaping human antibodies for therapy, Nature, 332(6162): 323-327 (1988).
Sambrook et al., Molecular Cloning: A Laboratory Manual, Cold Spring Harbor Laboratory Press, Cold Springs Harbor, New York (1989) (Table of Contents Only).
Shani, Tissue-specific expression of rat myosin light-chain 2 gene in transgenic mice, Nature, 314(6008): 283-286 (1985).
Sidman et al., Controlled release of macromolecules and pharmaceuticals from synthetic polypeptides based on glutamic acid, Biopolymers, 22(1): 547-556 (1983).
Smith, D. W., ed., Biocomputing: Informatics and Genome Projects, Academic Press, New York (1993) (Table of Contents Only).
Stewart and Young, Solid Phase Peptide Synthesis, Pierce Chemical Co., Rockford, IL (1984) (Table of Contents Only).
Swift et al., Tissue-specific expression of the rat pancreatic elastase I gene in transgenic mice, Cell, 38(3): 639-646 (1984).
Urlaub et al., Research Articles: Isolation of Chinese hamster cell mutants deficient in dihydrofolate reductase activity, PNAS USA, 77: 4216-4220 (1980).
Verhoeyen et al., Reshaping human antibodies: grafting an antilysozyme activity, Science, 239: 1534-1536 (1988).
Villa-Komaroff et al., Research Articles: A bacterial clone synthesizing proinsulin, PNAS USA, 75: 3727-3731 (1978).

von Heinje, G., Sequence Analysis in Molecular Biology, Academic Press (1987) (Table of Contents Only).
Wagner et al., Research Articles: Nucleotide sequence of the thymidine kinase gene of herpes simplex virus type 1, PNAS USA, 78: 1441-1445 (1981).
Wahl et al., Investigative Nuclear Medicine: Improved Radioimaging and Tumor Localization with Monoclonal F(ab')2, J. Nucl. Med., 24: 316-325 (1983).
Yamamoto et al., Identification of a functional promoter in the long terminal repeat of Rous sarcoma virus, Cell, 22(3): 787-797 (1980).
Zola, "Using Monoclonal Antibodies: Soluble Antigents", Monoclonal Antibodies: A Manual of Techniques, CRC Press, pp. 147-158 (1987).
Abbas, A.K. et al., Cellular and Molecular Immunology, W.B. Saunders Company, 2nd Edition, (1994).
Ausubel et al., Current Protocols in Molecular Biology, Chapter 18, John Wiley & Sons, NY, NY, (1997).
Banner et al., Crystal structure of the soluble human 55 kd TNF receptor-human TNF beta complex: implications for TNF receptor activation, Cell, 73(3):431-445, (1993).
Bork, P., Insight/Outlook: Powers and Pitfalls in Sequence Analysis: The 70% Hurdle, Genome Research, 10: 398-400 (2000).
*Boyle v. Gorman and Mattson*, Board of Patent Appeals and Interferences, Interference No. 104,336, Paper No. 39.
Bruggermann et al, Strategies for expressing human antibody repertoires in transgenic mice, Immunololgy Today, 17(8): 391-397 (1996).
Camerini et al., The T cell activation antigen CD27 is a member of the nerve growth factor/tumor necrosis factor receptor gene family, J. Immunol., 147: 3165-3169 (1991).
Caux et al., Activation of human dendritic cells through CD40 cross-linking, J. Exp. Med., 180: 1263-1272 (1994).
Chomczynski and Sacchi, Single-step method of RNA isolation by acid guanidinium thiocyanate-phenol-chloroform extraction, Anal. Biochem., 162(1): 156-159 (1987).
Crooke, An overview of progress in antisense therapeutics, Antisense & Nucleic Acid Drug Dev., 8(2): 115-122 (1998).
Doerks et al, Protein annotation: detective work for function prediction, Trends in Genetics, 14(6): 248-250 (1998).
Durkop et al., Molecular cloning and expression of a new member of the nerve growth factor receptor family that is characteristic for Hodgkin's disease, Cell, 68(3): 421-427 (1992).
EMBL Database, Accession No. AA170348, 1997.
EMBL-EBI Database Entry HS421358, Accession No. W74421, *Homo sapiens* cDNA Clone IMAGE:346544 3' Similar to Contains Alu Repetitive Element, Hillier et al., (Jun. 1996).
Emery, Cell Biology and Metabolism: Osteoprotegerin is a Receptor for the Cytotoxic Ligand TRAIL, V.G. et al., J. Biol. Chem., 273: 14363-14367 (1998).
Galibert et al., Cell Biology and Metabolism: The Involvement of Multiple Tumor Necrosis Factor Receptor (TNFR)-associated Factors in the Signaling Mechanisms of Receptor Activator of NF-B, a Member of the TNFR Superfamily, J. Biol. Chem., 273(51): 34120-34127 (1998).
Goeddel, D.V. ed., Systems for heterologous gene expression, Methods in Enzymology, v. 185:3-7, Academic Press (1990).
Goh et al., Original Articles: Aspartic acid 50 and tyrosine 108 are essential for receptor binding and cytotoxic activity of tumour necrosis factor beta (lymphotoxin), Protein Engineering, 4: 785-791 (1991).
Gray et al., Investigations: P-Element-Induced Recombination in *Drosophila melanogaster*: Hybrid Element Insertion, Genetics, 144(4): 1601-1610 (1996).
Gribskov et al., Research Articles: Profile analysis: detection of distantly related proteins, PNAS USA, 84: 4355-4358 (1987).
Harlow et al., Antibodies, A Laboratory Manual, Cold Spring Harbor Laboratory, Chapter 5, p. 76 only, (1988).
Imgenex product use sheet for product IMG-185B, anti-TRANCE/RANKL/OPGL/ODF, clone 12A380, downloaded Jan. 26, 2006.
Itoh et al., The polypeptide encoded by the cDNA for human cell surface antigen Fas can mediate apoptosis, Cell, 66(2):233-243 (1991).

Jakobovits, Aya, Production of fully human antibodies by transgenic mice, Current Opinion in Biotechnology, 6(5): 561-566 (1995).
Jimi et al., Osteoclast function is activated by osteoblastic cells through a mechanism involving cell-to-cell contact [corrected and republished in Endocrinology Aug. 1996;137(8)2187-90], Endocrinology, 137: 2187-2190 (1996).
Johnson et al., Cell, 47: 545-554 (1986).
Jones et al., J. Cell Sci., Suppl 13: 11-18 (1990).
Kodaira et al., Gene, 230: 121-127 (1999).
Kwon et al., PNAS USA, 86: 1963-1967 (1989).
Liu et al., Mol Reprod. Dev., 25:302-308 (1990).
Lonberg et al., Intern. Rev. Immunol., 13: 65-93 (1995).
Luthy et al., Protein Sci., 3:139-146 (1994).
Mallett et al., EMBO J., 9: 1063-1068 (1990).
Matsudaira et al., J. Biol. Chem., 262: 10035-10038 (1987).
Montgomery et al., Cell, 87: 427-436 (1996).
Nagata and Golstein, Science, 267: 1449-1456 (1995).
Pearson, Meth. Enzymol., 183: 63-98 (1990).
Romani et al., J. Exp. Med., 180: 83-93 (1994).
Roodman, G.D., Calcified Tissue Internatl, S94-S98 (1993).
Rothe, M. et al., Cell, 83: 1243-1252 (1995).
Schall, et al., Cell, 61: 361-370 (1990).
Skolnick et al., Trends in Biotech, 18(1): 34-39 (2000).
Stamenkovic et al., EMBO J., 8: 1403-1410 (1989).
Stressgen product use sheet for product AAM-425AF, anti-TRANCE/RANKL, clone 12A668, revised Jun. 27, 2005.
Suda et al., Endocr. Rev., Monograph, 4(1) :266-270 (1995).
Viney et al., J. Immunol., 160: 5815-5825 (1998).
Wiley et al., Immunity, 3: 673-682 (1995).
Wong et al., J. Biol. Chem., 273(43): 28355-28359 (1998).
Yang et al., PNAS USA, 82: 7994-7998 (1985).
Yun et al., Immunol., 161: 6113-6121 (1998).
Cha, Sun-Shin et al., Immunity, 11: 253-261 (1999).
Hymowitz, Sarah G. et al., Biochemistry, 39: 633-640 (2000).
Mongkolsapaya, J et al., Nature Structural Biology, 6: 1048-1053, (1999).
LaPlanche et al., 1986, Nucl. Acids Res. 14: 9081.
Stec et al., 1984, J. Am. Chem. Soc. 106: 6077.
Stein et al., 1988, Nucl. Acids Res. 16: 3209.
Zon et al., 1991, Anti-Cancer Drug Design 6: 539.
Uhlmann and Peyman, 1990, Chemical Reviews 90: 543.
Graham et al., 1973, Virology 52: 456.
Moult, 1996, Curr. Op. in Biotech. 7: 422-427.
Chu et al., 1981, Gene 13: 197.
Durbin et al., 1998, Biological Sequence Analysis, Cambridge University Press.
Dayhoff et al., 1978, Atlas of Protein Sequence and Structure 5:345-352.
Henikoff et al., 1992, Proc. Natl. Acad. Sci. USA 89: 10915-10919.
Needleman et al., 1970, J. Mol. Biol. 48:443-453.
Immunology—A Synthesis, 2nd Edition, (E. S. Golub and D. R. Gren, Eds.), 1991, Sinauer Associates, Sunderland, Mass.
Kyte et al., 1982, J. Mol. Biol. 157:105-131.
Tsukii, K; et al.; 1998; Biochemical and Biophysical Research Communications; 246(2): 337-341.
Takayanagi, H; et al.; 2000; Nature; 408:600-605.
Database GenBank, Accession No. AB008426; May 2, 1998.
Database GenBank, Accession No. AF019047; Nov. 22, 1997.
Database GenBank, Accession No. AF013170; Nov. 5, 1998.
Database GenBank, Accession No. AF019048; Nov. 22, 1997.
Database GenBank, Accession No. AF013171; Sep. 19, 1997.
Nagai. M .. et al.. 2000; Biochem Biophys Res Comm; 269:532-536.
Kong et al, "Osteoprotegerin ligand: a regulator of immune resonses and bone physiology", Immunology Today, vol. 21, No. 10, pp. 495-502 (2000).
Zola, 1987, Monoclonal Antibodies: A Manual of Techniques, pp. 147-158, CRC Press, Inc.
Zon et al., 1991, Oligonucleotides and Analogues: A Practical Approach, (F. Eckstein, ed.), Oxford University Press, Oxford England, pp. 87-108.
Genbank Accession No. J01749, dated Sep. 30, 2008.
Takebe et al., 1988, Mol. Cell Biol. 8:466-72.
Genbank Accession No. J02400, dated Dec. 14, 2000.
Seiki et al., 1983, Proc. Natl. Acad. Sci. U. S. A. 80:3618-22.
Genbank Accession No. J02029, dated Oct. 1, 1999.
Okayama and Berg, 1983. Mol. Cell Biol. 3:280-9.
Schillberg et al. (2003), Cell and Molecular Life Science 60: 433-45.
Bendig (1995), Methods: A Companion to Methods in Enzymology 8: 83-93.
Paul (1993), Fundamental Immunology, 3rd Edition, pp. 292-295.
Rudikoff et al. (1982), Proc. Natl. Acad. Sci. USA 79: 1979-83.
O'Brien et al. (2001), Bone 28(2): 208-14.
Mancini et al. (2000), Biochem. Biophys. Res. Comm. 279: 391-7.
Yoshimura et al. (2002), "Expression of receptor activator of NF-kappa B ligand and osteoprotegerin in culture of human periodontal ligaments cells", J. Periodont Res. 37: pp. 405-411.
Wise et al. (2002), "Inhibition of osteoclastogenesis by the secretion of osteoprotegerin in vitro by rat dental follicle cells and its implications for tooth eruption", Archives of Oral Biology 47: pp. 247-254.
Yasuda et al. (1998), "Identity of Osteoclastogenesis inhibitory factor OCIF inhibits Osteoclastogenesis in Vitro", Endocrinology 139:1329-1337.
Barbas et al. (1995), "Human autoantibody recognition of DNA", Proc. Natl .Acad. Sci. USA 92(7): pp. 2529-2533.
Beiboer et al. (2000), "Guided selection of a pan carcinoma specific antibody reveals similar binding characteristics yet structural divergence between the original murine antibody and its human equivalent", J. Mol. Biol. 296(3):833-49.
Desiderio et al. (2001), "A semi-synthetic repertoire of intrinsically stable antibody fragments derived from a single-framework scaffold", J. Mol. Biol. 310: pp. 603-615.
Desmyter et al. (2001), "Antigen specificity and high affinity binding provided by one single loop of a camel single-domain antibody" J. Biol. Chem. 276:26285-26290.
Ditzel et al. (1996), "Determinates of polyreactivity in a large panel of recombinant human antibodies from HIV-1 infection", J. Immunol. 157(2):739-49.
Kabat et al., Sequences of Proteins of Immunological Interest, Fifth Edition, NIH Publication No. 91-3242.
Klimka et al. (2000), "Human anti-CD30 recombinant antibodies by guided phage antibody selection using cell panning", Br. J. Cancer 83(2):252-60.
Hasemann and Capra (1993) "Immunoglobulins: Structure and Function," Fundamental Immunology, Third Edition pp. 288-292.
Rader et al. (1998), "A phage display approach for rapid antibody humanization designed combinatorial V gene libraries" Proc. Natl. Acad. Sci. USA 95(15):8910-5.
Schier et al. (1996), "Isolation of picomolar affinity anti-c-erbB-2 Single-Chain Fv by molecular evolution of the complementarity determing Regions in the Center of the Antibody Binding Site", J. Mol. Biol. 263:551-567.
Xu and Davis (2000), "Diversity in the CDR3 Region of Vh is sufficient for most antibody specificities", Immunity 13:37-45.
Adams et al., Nature, "The c-myc oncogene driven by immunoglobulin enhancers induces lymphoid malignancy in transgenic mice", 318: 533-538 (1985).
Alexander et al., "Expression of the c-myc oncogene under control of an immunoglobulin enhancer in E mu-myc transgenic mice", Mol. Cell. Biol., 7: 1436-1444 (1987).
Altschul et al., "Basic local alignment search tool.Current Protocols in Molecular Biology", J. Mol. Biol., 215: 403-410 (1990).
Ausubel et al., John Wiley & Sons, New York (1993) (Table of Contents Only).
Bayer et al., "Protein Biotinylation", Meth. in Enz., 184: 138-162 (1990).
Benoist and Chambon, "In vivo sequence requirements of the SV40 early promoter region", Nature, 290: 304-310 (1981).
Boulianne et al., "Production of functional chimaeric mouse/human antibody", Nature, 312: 643-646 (1984).
Brinster et al., "Regulation of metallothionein—thymidine kinase fusion plasmids injected into mouse eggs", Nature, 296: 39-42 (1982).
Brodeur et al., Monoclonal Antibody Production Techniques and Applications, 51-63, Marcel Dekker, Inc., New York (1987).

Bruggemann et al., "Designer mice: the production of human antibody repertoires in transgenic animals", Year in Immunol., 7: 33-40 (1993).
Cabilly et al., "Generation of Antibody Activity from Immunoglobulin Polypeptide Chains Produced in *Escherichia coli*", PNAS USA, 81: 3273-3277 (1984).
Carrillo et al., "The Multiple Sequence Alignment Problem in Biology", SIAM J. Applied Math., 48: 1073-1082 (1988).
Coligan et al., eds. Current Protocols in Immunology, Greene Publishing Assoc. and Wiley Interscience, New York, (1992, 1993) (Table of Contents Only).
Cunningham et al., "High-resolution epitope mapping of hGH-receptor interactions by alanine-scanning mutagenesis", Science, 244: 1081-1085 (1989).
DeBoer et al., "The tac promoter: A functional hybrid derived from the trp and lac promoters", PNAS USA, 80: 21-25 (1983).
de Haard et al., "Creating and engineering human antibodies for immunotherapy", Advanced Drug Delivery Reviews, 31: 5-31 (1998).
Devereux et al., "A comprehensive set of sequence analysis programs for the VAX", Nucleic Acids Research, 12(1): 387-395 (1984).
Eppstein et al., "Biological activity of liposome-encapsulated murine interferon y is mediated by a cell membrane receptor", PNAS USA, 82: 3688-3692 (1985).
Francis, "Protein modification and fusion protein", Focus on Growth Factors, 3: 4-10 (1992).
Gennero, A. R., ed., Remington's Pharmaceutical Sciences, 18th Edition, Mack Publishing Co. (1990) (Table of Contents Only).
Gribskov, M. and Devereux, J., eds., Sequence Analysis Primer, M. Stockton Press, New York (1991) (Table of Contents Only).
Griffin, A. M. and Griffin, H. G., eds. Computer Analysis of Sequence Data, Part 1, Humana Press, New Jersey (1994) (Table of Contents Only).
Grosschedl et al., "Introduction of a µ immunoglobulin gene into the mouse germ line: Specific expression in lymphoid cells and synthesis of functional antibody", Cell, 38: 647-658 (1984).
Hammer et al., "Diversity of alpha-fetoprotein gene expression in mice is generated by a combination of separate enhancer elements", Science, 235: 53-58 (1987).
Hanahan, "Heritable formation of pancreatic β-cell tumours in transgenic mice expressing recombinant insulin/simian virus 40 oncogenes", Nature, 315: 115-122 (1985).
Harlow and Lane, Antibodies: A Laboratory Manual, Cold Spring Harbor Laboratory Press, New York (1988) (Table of Contents Only).
Houghten, "General method for the rapid solid-phase synthesis of large numbers of peptides: Specificity of antigen-antibody interaction at the level of individual amino acids", PNAS USA, 82: 5131-5135 (1985).
Huycke et al., "Simplified Agar Plate Method for Quantifying Viable Bacteria", BioTechniques, 23: 648-650 (1997).
Jakobovits et al., "Analysis of homozygous mutant chimeric mice: Deletion of the immunoglobulin heavy-chain joining region blocks B-cell development and antibody production", PNAS USA, 90: 2551-2555 (1993).
Jakobovits et al, "Germ-line transmission and expression of a human-derived yeast artificial chromosome" Nature, 362: 255-258 (1993).
Johnston et al., "Bone Density Measurement and the Management of Osteoporosis", Primer on the Metabolic Bone Disease and Disorders of Mineral Metabolism, 2nd ed., M. J. Favus, ed., Raven Press, pp. 137-146 (1993).
Jones et al., "Replacing the complementarity-determining regions in a human antibody with those from a mouse." Nature, 321: 522-525 (1986).
Kelsey et al., "Species- and tissue-specific expression of human alpha 1-antitrypsin in transgenic mice", Genes and Devel., 1: 161-171 (1987).
Kitts et al., "A method for producing recombinant baculovirus expression vectors at high frequency. BioTechniques", Biotechniques, 14: 810-817 (1993).
Kohler et al., "Continuous cultures of fused cells secreting antibody of predefined specificity", Nature, 256: 495-497 (1975).

Kollias et al., "Regulated expression of human A gamma-, beta-, and hybrid gamma beta- globin genes in transgenic mice: manipulation of the developmental expression patterns", Cell, 46: 89-94 (1986).
Kong et al., "OPGL is a key regulator of osteoclastogenesis, lymphocyte development and lymph-node organogenesis.", Nature, 397: 315-323 (1999).
Kozbor, "A human hybrid myeloma for production of human monoclonal antibodies", J. Immunol., 133: 3001-3005 (1984).
Kranz et al., "Restricted reassociation of heavy and light chains from hapten-specific monoclonal antibodies", PNAS USA, 78: 5807-5811 (1981).
Krumlauf et al., "Developmental Regulation of ox-Fetoprotein Genes in Transgenic Mice", Mol. Cell. Biol., 5: 1639-1648 (1985).
Langer et al., "Biocompatibility of polymeric delivery systems for macromolecules", J. Biomed. Mater. Res., 15: 267-277 (1981).
Langer, "Controlled release of macromolecules", ChemTech., 12: 98-105 (1982).
Leder, "Consequences of widespread deregulation of the c-myc gene in transgenic mice: multiple neoplasms and normal development", Cell, 45: 485-495 (1986).
Lesk, A. M., ed., Computational Molecular Biology, Oxford University Press, New York (1988) (Table of Contents Only).
Lewis et al., "Use of a Novel Mutagenesis Strategy, Optimized Residue Substitution, to Decrease the Off-Rate of an Anti-gp120 Antibody", Mol. Immunol., 32: 1065-1072 (1995).
Liu et aHofbauer et al, "Osteoprotegerin and its cognate ligand: a new paradigm of osteoclastogenesis", European Journal of Endocrinology, vol. 139, No. 2, pp. 152-154 (1998)I., "Chimeric mouse-human IgGi antibody that can mediate lysis of cancer cells", PNAS USA, 84: 3439-3443 (1987).
Lucklow, "Bachulovirus systems for the expression of human gene products", Curr. Opin. Biotechnol., 4: 564-572 (1993).
Lucklow et al., "Efficient generation of infectious recombinant baculoviruses by site-specific transposon-mediated insertion of foreign genes into a baculovirus genome propagated in *Escherichia coli*", J. Virol., 67: 4566-4579 (1993).
MacDonald, "Expression of the pancreatic elastase I gene in transgenic mice. Hepatology", Hepatology, 7: 42S-51S (1987).
Magram et al., "Developmental regulation of a cloned adult β-globin gene in transgenic mice", Nature, 315: 338-340 (1985).
Chou et al., Prediction of protein conformation, 1974, Biochemistry 13(2): 222-245.
Chou et al., Conformational parameters for amino acids in helical, beta-sheet, and random coil regions calculated from proteins, 1974, Biochemistry 13(2): 211-222.
Chou et al., Prediction of the secondary structure of proteins from their amino acid sequence, 1978, Adv. Enzymol. Relat. Areas Mol. Biol. 47: 45-148.
Chou et al., Empirical predictions of protein conformation, 1978, Ann. Rev. Biochem. 47: 251-276.
Chou et al., Prediction of beta-turns, 1979, Biophys. J. 26(3): 367-383.
Holm et al., Protein folds and families: sequence and structure alignments, 1999, Nucl. Acid. Res. 27: 244-247.
Brenner et al., Population statistics of protein structures: lessons from structural classifications, 1997, Curr. Op. Struct. Biol. 7(3): 369-376.
Jones, Progress in protein structure prediction, 1997, Curr. Opin. Struct. Biol. 7(3): 377-87.
Sippl et al., Threading thrills and threats, 1996, Structure 4(1): 15-19.
Bowie et al., A method to identify protein sequences that fold into a known three-dimensional structure, 1991, Science 253: 164-170.
Burton and Woof, Human antibody effector function, 1992, Advances in Immunology 51: 1-84.
Ravetch and Bolland, IgG Fc receptors, 2001, Annu. Rev. Immunol. 19: 275-90.
Shields et al., Molecular Basis of Cell and Developmental Biology: High Resolution Mapping of the Binding Site on Human IgG1 for FcRI, FcRII, FcRIII, and FcRn and Design of IgG1 Variants with Improved Binding to the FcR, 2001, Journal of Biol. Chem 276: 6591-6604.

Telleman and Junghans, The role of the Brambell receptor (FcRB) in liver: protection of endocytosed immunoglobulin G (IgG) from catabolism in hepatocytes rather than transport of IgG to bile, 2000, Immunology 100(2): 245-251.

Medesan et al., Comparative studies of rat IgG to further delineate the Fc:FcRn interaction site, 1998, Eur. J. Immunol. 28(7): 2092-2100.

Berger and Kimmel, Methods in Enzymology, vol. 152, Guide to Molecular Cloning Techniques, 1987, Academic Press, Inc., San Diego, CA.

Proteins, Structures and Molecular Principles (Creighton, Ed.), 1984, W. H. New York: Freeman and Company.

Introduction to Protein Structure (Branden and Tooze, eds.), 1991, New York: Garland Publishing.

Thornton et at., Protein structure. Prediction of progress at last, 1991, Nature 354(6349): 105-6.

Fauchere, Elements for the Rational Design of Peptide Drugs, 1986, Adv. Drug Res. 15: 29.

Veber and Freidinger, The design of metabolically-stable peptide analogs, 1985, TINS p. 392-6.

Evans et al., Design of nonpeptidal ligands for a peptide receptor: cholecystokinin antagonists, 1987, J. Med. Chem. 30(7): 1229-39.

Rizo and Gierasch, Constrained peptides: models of bioactive peptides and protein substructures, 1992, Ann. Rev. Biochem. 61: 387-418.

Fundamental Immunology, 2nd ed., Ch. 7 (Paul, W., ed.) 1989, New York: Raven Press, ISBN: 0881674915 DDC: 616.079 LCC: QR181.

Kabat et al, Sequences of Proteins of Immunological Interest 1987 and 1991, 5th edn., National Institutes of Health, Bethesda, MD, NIH Publication No. 91-3242, pp. XV-338.

Chothia & Lesk, Canonical structures for the hypervariable regions of immunoglobulins, 1987, J. Mol. Biol. 196(4): 901-917.

Chothia et al., Conformations of immunoglobulin hypervariable regions, 1989, Nature 342(6252): 877-883.

Songsivilai & Lachmann, Bispecific antibody: a tool for diagnosis and treatment of disease, 1990, Clin. Exp. Immunol. 79(3): 315-321.

Kostelny et al., Formation of a bispecific antibody by the use of leucine zippers, 1992, J. Immunol. 148: 1547-1553.

Mendez et al., Functional transplant of megabase human immunoglobulin loci recapitulates human antibody response in mice, 1997, Nature Genetics 15(2): 146-156.

Lonberg et al., Antigen-specific human antibodies from mice comprising four distinct genetic modifications, 1994, Nature 368(6474): 856-859.

Harding and Lonberg, Class switching in human immunoglobulin transgenic mice, 1995, Ann. N.Y. Acad. Sci 764: 536-546.

Taylor et al., Molecular Biology: A transgenic mouse that expresses a diversity of human sequence heavy and light chain immunoglobulins, 1992, Nucleic Acids Research, 20: 6287-6295.

Chen et al., Original Research Papers: Immunoglobulin gene rearrangement in B cell deficient mice generated by targeted deletion of the JH locus, 1993, International Immunology 5: 647-656.

Tuaillon et al., Biased utilization of DHQ52 and JH4 gene segments in a human Ig transgenic minilocus is independent of antigenic selection, 1994, J. Immunol. 152: 2912-2920.

McGrogan et al., Heterogeneity at the 5' termini of mouse dihydrofolate reductase mRNAs. Evidence for multiple promoter regions, 1985, J. Biol. Chem. 260:2307-14.

Lonberg, "Transgenic Approaches to Human Monoclonal Antibodies," the Pharmacology of Monoclonal Antibodies, 1994, Handbook of Exp. Pharmacology 113: 49-101.

Taylor et al., Original Research Papers: Human immunoglobulin transgenes undergo rearrangement, somatic mutation and class switching in mice that lack endogenous IgM, 1994, International Immunology 6: 579-591.

Lonberg and Huszar, Human antibodies from transgenic mice, 1995, Intern. Rev. Immunol. 13(1): 65-93.

Setzer et al., Nucleotide sequence surrounding multiple polyadenylation sites in the mouse dihydrofolate reductase gene, 1982, J. Biol. Chem. 257:5143-7.

Fishwild et al., High-avidity human IgG kappa monoclonal antibodies from a novel strain of minilocus transgenic mice, 1996, Nature Biotechnology 14(7): 845-851.

Zuo et al., Gene targeting in the Ig kappa locus: efficient generation of lambda chain-expressing B cells, independent of gene rearrangements in Ig kappa, 1993, EMBO J. 12(3): 811-20.

Nunberg et al., Structure and genomic organization of the mouse dihydrofolate reductase gene, 1980, Cell 19(2):355-64.

Gasser et al, Research Articles: Expression of abbreviated mouse dihydrofolate reductase genes in cultured hamster cells, 1982, Proc. Natl. Acad. Sci. U. S. A. 79:6522-6.

Goodwin, et al., Molecular Biology: Characterization and nucleotide sequence of the gene for the common subunit of the bovine pituitary glycoprotein hormones, 1983, Nucleic Acids Res. 11:6873-82.

Genbank Accession No. X00004, dated Nov. 14, 2006.

Kuby, J, Immunology, "Cross-Reactivity", Publisher: W. H. Freeman and Company, New York, p. 125, (1992).

NCBI, Marra et al., The WashU-HHMI Mouse EST Project, GenBank Accession No. AA170348, (Feb. 16, 1997).

Parslow, T. et al., Medical Immunology, Appleton & Lange, eds., Edition 9, pp. 74-82, (1997).

Hofbauer et al, "Osteoprotegerin and its cognate ligand: a new paradigm of osteoclastogenesis", European Journal of Endocrinology, vol. 139, No. 2, pp. 152-154 (1998).

Clemens, J. Daniel et al.: "Evidence that serum NTx (collagen-type I N-telopeptides) can act as an immunochemical marker of bone resorption," Clinical Chemistry (1997) vol. 43, No. 11, pp. 2058-2063.

Kim et al.: "Effects of mushroom, *Pleurotus eryngii*, extracts on bone metabolism," Clinical Nutrition (2006) vol. 25, pp. 166-170.

Mitra, S.K. et al.: "The beneficial effect of OST-6 (OsteoCare), a herbomineral formulation, in experimental osteoporosis," Phytomedicine (2001) vol. 8, No. 3, pp. 195-201.

Murthy, P.S. Narayana et al.: "Effect of ormeloxifene on ovariectomy-induced bone resorption, osteoclast differentiation and apoptosis and TGF beta-3 expression," Journal of Steroid Biochemistry & Molecular Biology (2006) vol. 100, pp. 117-128.

Pascalis, Roberto De et al.: "Grafting of "Abbreviated" Complementarity-Determining Regions Containing Specificity-Determining Residues Essential for Ligand Contact to Engineer a Less Immunogenic Humanized Monoclonal Antibody," Journal of Immunology (2002) vol. 169, pp. 3076-3084.

* cited by examiner

Constant region Heavy Chain IgG1

```
gcctccacca  agggcccatc  ggtcttcccc  ctggcaccct  cctccaagag  cacctctggg  60
ggcacagcgg  ccctgggctg  cctggtcaag  gactacttcc  ccgaaccggt  gacggtgtcg  120
tggaactcag  gcgccctgac  cagcggcgtg  cacaccttcc  cggctgtcct  acagtcctca  180
ggactctact  ccctcagcag  cgtggtgacc  gtgccctcca  gcagcttggg  cacccagacc  240
tacatctgca  acgtgaatca  caagcccagc  aacaccaagg  tggacaagaa  agttgagccc  300
aaatcttgtg  acaaaactca  cacatgccca  ccgtgcccag  cacctgaact  cctggggga   360
ccgtcagtct  tcctcttccc  cccaaaaccc  aaggacaccc  tcatgatctc  ccggacccct  420
gaggtcacat  gcgtggtggt  ggacgtgagc  cacgaagacc  ctgaggtcaa  gttcaactgg  480
tacgtggacg  gcgtggaggt  gcataatgcc  aagacaaagc  cgcgggagga  gcagtacaac  540
agcacgtacc  gtgtggtcag  cgtcctcacc  gtcctgcacc  aggactggct  gaatgcaag   600
gagtacaagt  gcaaggtctc  caacaaagcc  ctcccagccc  ccatcgagaa  aaccatctcc  660
aaagccaaag  ggcagccccg  agaaccacag  gtgtacaccc  tgcccccatc  ccgggatgag  720
ctgaccaaga  accaggtcag  cctgacctgc  ctggtcaaag  gcttctatcc  cagcgacatc  780
gccgtggagt  gggagagcaa  tgggcagcca  gagaacaact  acaagaccac  gcctcccgtg  840
ctggactccg  acggctcctt  cttcctctat  agcaagctca  ccgtggacaa  gagcaggtgg  900
cagcagggga  acgtcttctc  atgctccgtg  atgcatgagg  ctctgcacaa  ccactacacg  960
cagaagagcc  tctccctgtc  tccgggtaaa  tgataagtcg  acatgccctg  aattctgcag  1020
atatccatca  cactggcggc  cgctcgagca  tgcatctaga           gggccc         1066
```

Figure 1A

```
ASTKGPSVFP LAPSSKSTSG GTAALGCLVK DYFFEPVTVS WNSGALTSGV HTFPAVLQSS  60
GLYSLSSVVT VPSSSLGTQT YICNVNHKPS NTKVDKKVEP KSCDKTHTCP PCPAPELLGG 120
PSVFLFPPKP KDTLMISRTP EVTCVVVDVS HEDEEVKFNW YVDGVEVHNA KTKPREEQYN 180
STYRVVSVLT VLHQDWLNGK EYKCKVSNKA LPAFIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK                                 330
```

Figure 1B

Kappa chain constant region

```
actgtggctg caccatctgt cttcatcttc ccgccatctg atgagcagtt gaaatctgga    60
actgcctctg ttgtgtgcct gctgaataac ttctatccca gagaccccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat caggccctga gctcgcccgt cacaaagagc   300
ttcaacaggg gagagtgtta g                                             321
```

Figure 2A

```
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106
```

Figure 2B

22B3 Heavy Chain

```
gaggtgcagc tggtgcagtc tgggggaggc ttggtacatc ctgggggtc cctgagactc    60
tcctgtgaag gctctggatt caccttcagt agcaatggta tgcactgggt gcgccagact   120
ccaggaaaag gtctggagtg gtctggagt attggtactg ctggtggcac atactatgca   180
gactccgtga agggccgatt caccattcc agagacaatg tcaagaagtc ctgtatctt    240
caaatgaaca gcctgagagc cgaggacatg gctattatt attgtgtaag aaaaaactgg   300
ggatggttcg acccctgggg ccaggagcc ctggtcaccg tctctagt                348
```

Figure 3A

```
EVQLVQSGG  LVHPGGSLRL  SCEGSGFTFS  SNGMHWVRQT  PGKGLEWVSG  IGTAGGTYYA    60
DSVKGRFTIS  RDNVKKSLYL  QMNSLRAEDM  AIYYCVRKNW  GWFDPWGQGA  LVTVSS      116
```

Figure 3B

22B3 Kappa Chain

```
gaaattgtgc tgacccagtc tccagccacc ctgtctttgt ctccagggga aagagccacc   60
ctctcctgca ggccagtca gagtgttaac agctacttag cctgttcca acagaaacct  120
ggccaggctc ccagactcct catctatgat gcatccaaca gggccactgg catcccagcc  180
aggttcagtg gcagtgggtc tggacagac ttcactctca ccatcagcag ccttgagcct  240
gaagattttg caatttatta ctgtcagcag cgtagcaact ggcctccgtt cactttggc  300
caggggacca agctggagat caaacga                                     327
```

Figure 4A

```
EIVLTQSPAT LSLSPGERAT LSCRASQSVN SYLAWFQQKP GQAPRLLIYD ASNRATGIPA   60
RFSGSGSGTD FTLTISSLEP EDFAIYYCQQ RSNWPPFTFG QGTKLEIKR             109
```

Figure 4B

2E11 Heavy Chain

```
gaggtgcagc tggtgcagtc gggggagac ttggtacatc ctgggggtc cctgagactc    60
tcctgtgtcg gctctggatt caccttcagt cactatcctt tgcactgggt tgcgccaggct  120
ccaggaaaag gtctggagtg gatatcaggt attcatactg gtggtggcac atactataca  180
gactccgtga agggccggtt caccatctcc agcgacaatg ccaagaactc cttatatctt  240
caaatgaaca ccctgagagc cgaggacatg gctgtgtatt actgtgcaag agggcgaaac  300
tcctttgact actggggcca gggaaccctg gtcatcgtct ctagt               345
```

Figure 5A

```
EVQLVQSGGD LVHPGGSLRL SCVGSGFTFS HYPIHWVRQA PGKGLEWISG IHTGGGTYYT    60
DSVKGRFTIS SDNAKNSLYL QMNTLRAEDM AVYYCARGRN SFDYWGQGTL VIVSS       115
```

Figure 5B

2E11 Kappa Chain

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagtct   240
gaagattttg caacttatta ctgccaacag tataatagtt acccccccac cttcggccaa   300
gggacacgac tggagattaa acga                                          324
```

Figure 6A

DIQMTQSPSS LSASVGDRVT ITCRASQGIS SWLAWYQQKP EKAPKSLIYA ASSLQSGVPS    60
RFSGSGSGTD FTLTISSLQS EDFATYYCQQ YNSYPPTFGQ GTRLEIKR               108

Figure 6B

2D8 Heavy Chain

```
gaggtgcagc tggtgcagtc tgggggaggc ttggtacatc ctggggggtc cctgagactc    60
tcctgtgcag gctctggatt cacccttcagt agctatggga tgcactgggt tcgccaggct   120
ccaggaaaag gtctggagtg ggtctcaggt attggtactg gtggtggcac atactatgca   180
gactccgtga agggccgatt caccatctcc agagacaatg tcaagaactc cttgtatctt   240
caaatgaaca gcctgagagc cgaggacatg gctgtgtatt actgtgcaag aaaaaactgg   300
ggatggtttg actactgggg ccaggaacc ctggtcaccg tctcctagt                 348
```

Figure 7A

```
EVQLVQSGGG LVHPGGSLRL SCAGSGFTFS SYGMHWVRQA PGKGLEWVSG IGTGGGTYYA    60
DSVKGRFTIS RDNVKNSLYL QMNSLRAEDM AVYYCARKNW GWFDYWGQGT LVTVSS        116
```

Figure 7B

2D8 Kappa Chain

```
gaaattgtgc tgacccagtc tccagccacc ctgtctttgt ctccagggga aagagccacc   60
ctctcctgca gggccagtca gagtattagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaaat ggcctccgta cacttttggc  300
cagggacca aactcgagat caaacga                                        327
```

Figure 8A

```
EIVLTQSPAT LSLSPGERAT LSCRASQSIS SYLAWYQQKP GQAPRLLIYD ASNRATGIPA   60
RFSGSGSGTD FTLTISSLEP EDFAVYYCQQ RSKWPPYTFG QGTKLEIKR             109
```

Figure 8B

18B2 Heavy Chain

```
gaggtgcagc tggtgcagtc tgggggaggc ttggtacatc ctgggggtc cctgagactc    60
tcctgtgtag gctctagatt cacctcagt gcctatccta tgcactggt tgccaggct    120
ccaggaaaag gtctggagtg gtatcaggt attgttctg gtgttggcac aaactatgca    180
gactccgtga agggccgatt caccatctcc agagacactg ccaagaactc cttgtatctt    240
caaatgaaca gcctgagagc cgaggacatg gctgtgtatt actgtgcaag agggaggaat    300
tctttgact actggggcca gggaaccctg gtcaccgtct ctagt                     345
```

Figure 9A

```
EVQLVQSGGG LVHPGGSLRL SCVGSRFTFS AYPMHWVRQA PGKGLEWVSG IGSGGGTNYA    60
DSVKGRFTIS RDTAKNSLYL QMNSLRAEDM AVYYCARGRN SFDYWGQGTL VTVSS        115
```

Figure 9B

18B2 Kappa Chain

```
gacatccaga tgacccagtc tccatcctca ctgtctgcat ctgtaggaga cagagtcacc    60
atcacttgtc gggcgagtca gggtattagc acctggttag cctgtatca gcagaaacca   120
gagaaagccc ctaagtccct gatctatgct gcatccagtt tcactctca ggtcccatcg   180
aggttcagcg gcagtggatc tgggacagat ttcactctca ccatcagcag cctgcagcct   240
gaagattttg caacttatta ctgccaacag tataatagtt acccctccga gttcggccaa   300
gggaccaagg tggagatcaa acga                                          324
```

Figure 10A

```
DIQMTQSPSS LSASVGDRVT ITCRASQGIS TWLAWYQQKP EKAPKSLIYA ASSLQSGVPS    60
RFSGSGSGTD FTLTISSLQP EDFATYYCQQ YNSYPPTFGQ GTKVEIKR              108
```

Figure 10B

16E1 Heavy Chain

```
gaggtccagc tggtgcagtc tggggaggc ttggtacatc ctgggggtc cctgagactc    60
tcctgtgcag gctctgatt cacttcagt ggccatgctt tgcactggt tcgccaggct   120
ccaggaaaag gtctggagtg gtctcaggt attgtactc attgtgggac atactatgca   180
gactccgtga aggccgatt caccatctcc agagacaatg ccaagaactc cttgttcctt   240
caaatgaaca gcctgagcgc cgaggacatg gctgtgtatt actgtacaag aagaaactgg   300
ggacaatttg actactgggg ccaggaaacc ctggtcaccg tctctagt              348
```

Figure 11A

```
EVQLVQSGGG LVHPGGSLRL SCAGSGFTFS GHALHWVRQA PGKGLEWVSG IGTHGGTYYA    60
DSVKGRFTIS RDNAKNSLFL QMNSLSAEDM AVYYCTRRNW GQFDYWGQGT LVTVSS      116
```

Figure 11B

16E1 Kappa

```
gaaattgtgc tgactcagtc tccagccacc ctgtctttgt ctccagggga aagagccacc   60
ctctcctgca gggccagtca gagtgttagc agctacttag cctggtacca acagaaacct  120
ggccaggctc ccaggctcct catctatgat gcatccaaca ggccactgg catcccagcc  180
aggttcagtg gcagtgggtc tgggacagac ttcactctca ccatcagcag cctagagcct  240
gaagattttg cagtttatta ctgtcagcag cgtagcaact ggcctccgta cactttggc   300
cagggacca agctggagat caaacga                                       327
```

Figure 12A

```
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPPYTFG QGTKLEIKR            109
```

Figure 12B

9H7 Heavy Chain

```
gaggtgcagc tggtgcagtc tgggggaggc ttggtacatc ctggggggtc cctgagactc    60
tcctgtgaag gctctggatt caccttcagt agcaatggta tgcactgggt gcgccagact   120
ccaggaaaag gtctggagtg gtctcaggt attgtactg cggtggcac atactatgca    180
gactccgtga agggccgatt caccatttcc agagacaatg tcaagaagtc cttgtatctt   240
caaatgaaca gcctgagagc cgaggacatg gctattatt attgtgtaag aaaagactgg   300
ggatggttcg accccctggg ccagggagcc ctggtcaccg tctctagt              348
```

Figure 13A

```
EVQLVQSGGG LVHPGGSLRL SCEGSGFTFS SNGMHWVRQT PGKGLEWVSG IGTAGGTYYA    60
DSVKGRFTIS RDNVKKSLYL QMNSLRAEDM AIYYCVRKDW GWFDPWGQGA LVTVSS       116
```

Figure 13B

9H7 Kappa Chain

```
gaaattgtgc tgacccagtc tccagccacc ctgtctttgt ctccaggga aagagccacc    60
ctctcctgca ggccagtca gagtattagc agctacttag cctggtacca acagaaacct   120
ggccagcctc ccaggctcct catctatgat gcatccaaca ggccactgg catcccagcc   180
aggttcagtg gcagtgggtc tgggacagac ttcactctca ccatcagcag cctagagcct   240
gaagattttg cagtttatta ctgtcagcag cgtagcaaat ggcctccgta cactttggc   300
cagggacca agctggagat caaacga                                        327
```

Figure 14A

EIVLTQSPAT LSLSPGERAT LSCRASQSIS SYLAWYQQKP GQAPRLLIYD ASNRATGIPA    60
RFSGSGSGTD FTLTISSLEP EDFAVYYCQQ RSKWPPYTFG QGTKLEIKR              109

Figure 14B

HEAVY CHAIN ALIGNMENT

|  | FR1 | CDR1 | FR2 | CDR2 |
|---|---|---|---|---|
| 16E1 | EVQLVQSGGG LVHPGGSLRL SCAGSGFTFS | GHALH | WVRQA PGKGLEWVSG | IGTHGGTYY ADSVKGRFTI |
| 2E11 | EVQLVQSGGD LVHPGGSLRL SCVGSGFTFS | HYPLH | WVRQA PGKGLEWISG | IHTGGGTYY TDSVKGRFTI |
| 18B2 | EVQLVQSGGG LVHPGGSLRL SCVGSRFTFS | AYPMH | WVRQA PGKGLEWVSG | IGSGGTNY ADSVKGRFTI |
| 2D8 | EVQLVQSGGG LVHPGGSLRL SCAGSGFTFS | SYGMH | WVRQA PGKGLEWVSG | IGTGGGTYY ADSVKGRFTI |
| 22B3 | EVQLVQSGGG LVHPGGSLRP SCEGSGFTFS | SNGMH | WVRQT PGKGLEWVSG | IGTAGGTYY ADSVKGRFTI |
| 9H7 | EVQLVQSGGG LVHPGGSLRL SCEGSGFTFS | SNGMH | WVRQT PGKGLEWVSG | IGTAGGTYY ADSVKGRFTI |

|  | FR3 | CDR3 |
|---|---|---|
| 16E1 | SRDNAKNSLF LQMNSLSAED MAVYYCTR | NWGQFDY |
| 2E11 | SSDNAKNSLY LQMNTLRAED MAVYYCARG | RNS--FDY |
| 18B2 | SRDTAKNSLY LQMNSLRAED MAVYYCARG | RNS--FDY |
| 2D8 | SRDNKNSLY LQMNSLRAED MAVYYCARK | NWGWFDY |
| 22B3 | SRDNVKKSLY LQMNSLRAED MAIYYCVRK | NWGWFDP |
| 9H7 | SRDNVKKSLY LQMNSLRAED MAIYYCVRK | DWGWFDP |

Figure 15

LIGHT CHAIN ALIGNMENT

| | FR1 | CDR1 | FR2 | CDR2 | |
|---|---|---|---|---|---|
| 16E1 | DIQMTQSPSS LSASVGDRVT | ITCRASQGI SSWLA | WYQQK PEKAPKSLIY | AASSLQSGVP | SRFSGSGSGT |
| 2E11 | DIQMTQSPSS LSASVGDRVT | ITCRASQGI STWLA | WYQQK PEKAPKSLIY | AASSLQSGVP | SRFSGSGSGT |
| 18B2 | EIVLTQSPAT LSLSPGERAT | LSCRASQSI SSYLA | WYQQK PGQAPRLLIY | DASNRATGIP | ARFSGSGSGT |
| 2D8 | EIVLTQSPAT LSLSPGERAT | LSCRASQSI SSYLA | WYQQK PGQAPRLLIY | DASNRATGIP | ARFSGSGSGT |
| 22B3 | EIVLTQSPAT LSLSPGERAT | LSCRASQSV NSYLA | WYQQK PGQAPRLLIY | DASNRATGIP | ARFSGSGSGT |
| 9H7 | EIVLTQSPAT LSLSPGERAT | LSCRASQSV SSYLA | WYQQK PGQAPRLLIY | DASNRATGIP | ARFSGSGSGT |

| | FR3 | CDR3 |
|---|---|---|
| 16E1 | DFTLTISSLQ SEDFATYYCQ | QYNSYPP-T |
| 2E11 | DFTLTISSLQ PEDFATYYCQ | QYNSYPP-T |
| 18B2 | DFTLTISSLE PEDFAVYYCQ | QRSKWPPYT |
| 2D8 | DFTLTISSLE PEDFAVYYCQ | QRSKWPPYT |
| 22B3 | DFTLTISSLE PEDFAIYYCQ | QRSNWPPET |
| 9H7 | DFTLTISSLE PEDFAVYYCQ | QRSNWPPYT |

Figure 16

```
Mouse OPG ligand    199  TLSNGKLRVNQDGFYYLYANICFRHHETSGSVPTDYLQLMVYVVKTSIKI  248
Human OPG ligand    200  TLSNGKLIVNQDGFYYLYANICFRHHETSGDLATEYLQLMVYVVIKTSIKI 249

Mouse OPG ligand/DE      TLSNGKLRVNQDGFYYLYANICFRHHETSGDLATEYLQLMVYVVKTSIKI
```

HUMAN ANTI-OPGL NEUTRALIZING ANTIBODIES AS SELECTIVE OPGL PATHWAY INHIBITORS

This application is a continuation of U.S. patent application Ser. No. 12/705,962, filed Feb. 15, 2010, which is a continuation of U.S. patent application Ser. No. 10/408,901, filed Apr. 7, 2003, now U.S. Pat. No. 7,718,776, which is related to and claims priority to U.S. provisional application Ser. No. 60/370,407, filed Apr. 5, 2002. The disclosure of each of these applications is incorporated by reference herein.

FIELD OF THE INVENTION

The invention relates to antibodies that bind osteoprotegerin ligand (OPGL). Compositions and methods for the treatment of bone diseases, such as osteoporosis, bone loss from arthritis, Paget's disease, and osteopenia, are also provided.

BACKGROUND OF THE INVENTION

Living bone tissue exhibits a dynamic equilibrium between formation of bone, known as deposition, and breakdown of bone, known as resorption. These processes can be mediated by at least two cell types: osteoblasts, which secrete molecules that comprise the organic matrix of bone (deposition); and osteoclasts, which promote dissolution of the bone matrix and solubilization of bone salts (resorption). In certain individuals, such as post-menopausal women, the rate of resorption can exceed the rate of deposition, which may result in reduced bone mass and strength, increased risk of fractures, and slow or incomplete repair of broken bones.

Osteoprotegerin ligand (OPGL) is a member of the TNF family of cytokines and promotes formation of osteoclasts through binding to the receptor activator of NF-κB (RANK, also called osteoclast differentiation and activation receptor, or ODAR). Osteoprotegerin (OPG), on the other hand, inhibits the formation of osteoclasts by sequestering OPGL and preventing OPGL association with ODAR. Thus, the amount of OPGL associated with ODAR correlates with the equilibrium between bone deposition and resorption. Individuals who suffer from osteopenic diseases, such as osteoporosis, show a greater rate of bone resorption than deposition, which may result from increased levels or activity of OPGL. Thus, it would be useful to have molecules that can regulate the activity of OPGL in osteoclastogenesis. It would also be useful to be able to detect the amount of OPGL in a biological sample, such as a blood sample, to diagnose an osteopenic disorder relating to increased levels of OPGL.

SUMMARY OF THE INVENTION

The invention provides monoclonal antibodies that bind to osteoprotegerin ligand (OPGL). Preferably, the antibodies inhibit binding of OPGL to an osteoclast differentiation and activation receptor (ODAR). Also provided by this invention are hybridoma cell lines that produce, and most preferably, secrete into cell culture media the monoclonal antibodies of the invention. The antibodies of the invention are useful for treating various disorders associated with low bone density.

In certain aspects, the invention provides antibodies, preferably monoclonal antibodies, most preferably human antibodies, comprising a heavy chain and a light chain, wherein the heavy chain comprises an IgG$_1$, IgG$_2$, or an IgG$_4$ heavy chain constant region. Preferably, an antibody of the invention comprises an amino acid sequence of the IgG$_1$ heavy chain constant region as set forth in SEQ ID NO: 2 or an antigen-binding or an immunologically functional immunoglobulin fragment thereof.

The invention also provides antibodies, preferably monoclonal antibodies, most preferably human antibodies, comprising a heavy chain and a light chain, wherein the light chain comprises an amino acid sequence as set forth in SEQ ID NO: 4 or an antigen-binding or an immunologically functional immunoglobulin fragment thereof.

The invention relates specifically to human antibodies, most preferably monoclonal antibodies that specifically bind the D-E loop region of OPGL. The invention also relates to human antibodies, preferably monoclonal antibodies, that bind to a region of osteoprotegerin ligand (OPGL) that is outside the D-E loop region. In addition, the invention relates to human antibodies, preferably monoclonal antibodies, that bind to both a region of OPGL that is outside the D-E loop region and all or a portion of the D-E loop region. In one aspect, antibodies of the invention bind to a first region of OPGL that is outside the D-E loop region and then, while remaining bound to the first region, bind to a second region that is all or a portion of the D-E loop region. Such binding is referred to herein as consecutive. In another aspect, antibodies of the invention can bind to a first region of OPGL that is outside the D-E loop region and a second region that is all or a portion of the D-E loop region at the same time. Such binding is referred to herein as simultaneous.

In certain aspects, antibodies of the invention comprise a heavy chain and a light chain, wherein the variable region of the heavy chain comprises an amino acid sequence as set forth in any of SEQ ID NO: 6, SEQ ID NO: 14, SEQ ID NO: 22, or SEQ ID NO: 26, or an antigen-binding or an immunologically functional immunoglobulin fragment thereof. In other aspects, the light chain variable region comprises an amino acid sequence as set forth in any of SEQ ID NO: 8, SEQ ID NO: 16, SEQ ID NO: 24, or SEQ ID NO: 28, or an antigen-binding or an immunologically functional immunoglobulin fragment thereof. In additional aspects, the heavy chain comprises an amino acid sequence as set forth in any of SEQ ID NO: 30, SEQ ID NO: 38, SEQ ID NO: 46, or SEQ ID NO: 50, or an antigen-binding or an immunologically functional immunoglobulin fragment thereof. In still further aspects, the light chain comprises an amino acid sequence as set forth in any of SEQ ID NO: 32, SEQ ID NO: 40, SEQ ID NO: 48, or SEQ ID NO: 52, or an antigen-binding or an immunologically functional immunoglobulin fragment thereof.

The invention also provides antibodies that bind specifically to OPGL, wherein the heavy chain comprises a heavy chain variable region as set forth in SEQ ID NO: 6, or an antigen-binding or an immunologically functional immunoglobulin fragment thereof, and the light chain comprises a light chain variable region comprising an amino acid sequence as set forth in SEQ ID NO: 8, or an antigen-binding or an immunologically functional immunoglobulin fragment thereof.

In certain aspects, the invention provides antibodies, comprising a heavy chain and a light chain, (a) wherein the heavy chain comprises a first variable region, and wherein the first variable region comprises a sequence that has at least 90% identity to the amino acid sequence set forth in SEQ ID NO: 6, and (b) wherein the light chain comprises a second variable region, and wherein the second variable region comprises a sequence that has at least 90% identity to the amino acid sequence set forth in SEQ ID NO: 8, and (c) wherein the antibody interacts with OPGL.

In other aspects, the first variable region comprises a sequence that has at least 95% identity to the amino acid sequence set forth in SEQ ID NO: 6, and the second variable region comprises a sequence that has at least 95% identity to the amino acid sequence set forth in SEQ ID NO: 8.

In still other aspects, the first variable region comprises a sequence that has at least 99% identity to the amino acid sequence set forth in SEQ ID NO: 6, and the second variable region comprises a sequence that has at least 99% identity to the amino acid sequence set forth in SEQ ID NO: 8.

The invention further provides antibodies that bind specifically to OPGL, wherein the heavy chain comprises a heavy chain variable region as set forth in SEQ ID NO: 14, or an antigen-binding or an immunologically functional immunoglobulin fragment thereof, and the light chain comprises a light chain variable region comprising an amino acid sequence as set forth in SEQ ID NO: 16, or an antigen-binding or an immunologically functional immunoglobulin fragment thereof.

In certain aspects, the invention provides antibodies, comprising a heavy chain and a light chain, (a) wherein the heavy chain comprises a first variable region, and wherein the first variable region comprises a sequence that has at least 90% identity to the amino acid sequence set forth in SEQ ID NO: 14, and (b) wherein the light chain comprises a second variable region, and wherein the second variable region comprises a sequence that has at least 90% identity to the amino acid sequence set forth in SEQ ID NO: 16, and (c) wherein the antibody interacts with OPGL.

In other aspects, the first variable region comprises a sequence that has at least 95% identity to the amino acid sequence set forth in SEQ ID NO: 14, and the second variable region comprises a sequence that has at least 95% identity to the amino acid sequence set forth in SEQ ID NO: 16.

In further aspects, the first variable region comprises a sequence that has at least 99% identity to the amino acid sequence set forth in SEQ ID NO: 14, and the second variable region comprises a sequence that has at least 99% identity to the amino acid sequence set forth in SEQ ID NO: 16.

The invention provides antibodies that bind specifically to OPGL, wherein the heavy chain comprises a heavy chain variable region as set forth in SEQ ID NO: 22, or an antigen-binding or an immunologically functional immunoglobulin fragment thereof, and the light chain comprises a light chain variable region comprising an amino acid sequence as set forth in SEQ ID NO: 24, or an antigen-binding or an immunologically functional immunoglobulin fragment thereof.

In certain aspects, the invention provides antibodies, comprising a heavy chain and a light chain, (a) wherein the heavy chain comprises a first variable region, and wherein the first variable region comprises a sequence that has at least 90% identity to the amino acid sequence set forth in SEQ ID NO: 22, and (b) wherein the light chain comprises a second variable region, and wherein the second variable region comprises a sequence that has at least 90% identity to the amino acid sequence set forth in SEQ ID NO: 24, and (c) wherein the antibody interacts with OPGL.

In particular aspects, the first variable region comprises a sequence that has at least 95% identity to the amino acid sequence set forth in SEQ ID NO: 22, and the second variable region comprises a sequence that has at least 95% identity to the amino acid sequence set forth in SEQ ID NO: 24.

In further aspects, the first variable region comprises a sequence that has at least 99% identity to the amino acid sequence set forth in SEQ ID NO: 22, and the second variable region comprises a sequence that has at least 99% identity to the amino acid sequence set forth in SEQ ID NO: 24.

In addition, the invention provides antibodies that bind specifically to the D-E loop region of OPGL, wherein the heavy chain comprises a heavy chain variable region as set forth in SEQ ID NO: 26, or an antigen-binding or an immunologically functional immunoglobulin fragment thereof, and the light chain comprises a light chain variable region comprising an amino acid sequence as set forth in SEQ ID NO: 28, or an antigen-binding or an immunologically functional immunoglobulin fragment thereof.

In certain aspects, the invention provides antibodies, comprising a heavy chain and a light chain, (a) wherein the heavy chain comprises a first variable region, and wherein the first variable region comprises a sequence that has at least 90% identity to the amino acid sequence set forth in SEQ ID NO: 26, and (b) wherein the light chain comprises a second variable region, and wherein the second variable region comprises a sequence that has at least 90% identity to the amino acid sequence set forth in SEQ ID NO: 28, and (c) wherein the antibody interacts with OPGL.

In other aspects, the first variable region comprises a sequence that has at least 95% identity to the amino acid sequence set forth in SEQ ID NO: 26, and the second variable region comprises a sequence that has at least 95% identity to the amino acid sequence set forth in SEQ ID NO: 28.

In additional aspects, the first variable region comprises a sequence that has at least 99% identity to the amino acid sequence set forth in SEQ ID NO: 26, and the second variable region comprises a sequence that has at least 99% identity to the amino acid sequence set forth in SEQ ID NO: 28.

The invention also provides antibodies that bind specifically to OPGL, wherein the heavy chain comprises an amino acid sequence as set forth in SEQ ID NO: 30, or an antigen-binding or an immunologically functional immunoglobulin fragment thereof, and the light chain comprises an amino acid sequence as set forth in SEQ ID NO: 32, or an antigen-binding or an immunologically functional immunoglobulin fragment thereof.

The invention also provides antibodies that bind specifically to OPGL, wherein the heavy chain comprises an amino acid sequence as set forth in SEQ ID NO: 38, or an antigen-binding or an immunologically functional immunoglobulin fragment thereof, and the light chain comprises a light chain variable region comprising an amino acid sequence as set forth in SEQ ID NO: 40, or an antigen-binding or an immunologically functional immunoglobulin fragment thereof.

The invention provides antibodies that bind specifically to OPGL, wherein the heavy chain comprises an amino acid sequence as set forth in SEQ ID NO: 46, or an antigen-binding or an immunologically functional immunoglobulin fragment thereof, and the light chain comprises a light chain variable region comprising an amino acid sequence as set forth in SEQ ID NO: 48, or an antigen-binding or an immunologically functional immunoglobulin fragment thereof.

The invention provides antibodies that bind specifically to OPGL, wherein the heavy chain comprises an amino acid sequence as set forth in SEQ ID NO: 50, or an antigen-binding or an immunologically functional immunoglobulin fragment thereof, and the light chain comprises a light chain variable region comprising an amino acid sequence as set forth in SEQ ID NO: 52, or an antigen-binding or an immunologically functional immunoglobulin fragment thereof.

In certain aspects, the invention provides antibodies that specifically bind OPGL and comprises a heavy chain and a light chain, wherein the heavy chain variable region comprises an amino acid sequence as set forth in SEQ ID NO: 10 or SEQ ID NO: 18, or an antigen-binding or an immunologically functional immunoglobulin fragment thereof. In other aspects, the light chain variable region comprises an amino acid sequence as set forth in SEQ ID NO: 12 or SEQ ID NO:

20, or an antigen-binding or an immunologically functional immunoglobulin fragment thereof.

The invention also provides antibodies that specifically bind OPGL, wherein the heavy chain variable region comprises an amino acid sequence as set forth in SEQ ID NO: 34 or SEQ ID NO: 42, or an antigen-binding or an immunologically functional immunoglobulin fragment thereof. In other aspects, the light chain variable region comprising an amino acid sequence as set forth in SEQ ID NO: 36 or SEQ ID NO: 44, or an antigen-binding or an immunologically functional immunoglobulin fragment thereof.

The invention further provides antibodies that specifically bind OPGL, wherein the heavy chain comprises a heavy chain variable region as set forth in SEQ ID NO: 10, or an antigen-binding or an immunologically functional immunoglobulin fragment thereof, and the light chain comprises a light chain variable region comprising an amino acid sequence as set forth in SEQ ID NO: 12, or an antigen-binding or an immunologically functional immunoglobulin fragment thereof.

In certain aspects, the invention provides antibodies, comprising a heavy chain and a light chain, (a) wherein the heavy chain comprises a first variable region, and wherein the first variable region comprises a sequence that has at least 90% identity to the amino acid sequence set forth in SEQ ID NO: 10, and (b) wherein the light chain comprises a second variable region, and wherein the second variable region comprises a sequence that has at least 90% identity to the amino acid sequence set forth in SEQ ID NO: 12, and (c) wherein the antibody interacts with OPGL.

In further aspects, the first variable region comprises a sequence that has at least 95% identity to the amino acid sequence set forth in SEQ ID NO: 10, and the second variable region comprises a sequence that has at least 95% identity to the amino acid sequence set forth in SEQ ID NO: 12.

In other aspects, the first variable region comprises a sequence that has at least 99% identity to the amino acid sequence set forth in SEQ ID NO: 10, and the second variable region comprises a sequence that has at least 99% identity to the amino acid sequence set forth in SEQ ID NO: 12.

The invention also provides antibodies that specifically bind, wherein the heavy chain comprises a heavy chain variable region as set forth in SEQ ID NO: 18, or an antigen-binding or an immunologically functional immunoglobulin fragment thereof, and the light chain comprises a light chain variable region comprising an amino acid sequence as set forth in SEQ ID NO: 20, or an antigen-binding or an immunologically functional immunoglobulin fragment thereof.

In certain aspects, the invention provides antibodies, comprising a heavy chain and a light chain, (a) wherein the heavy chain comprises a first variable region, and wherein the first variable region comprises a sequence that has at least 90% identity to the amino acid sequence set forth in SEQ ID NO: 18, and (b) wherein the light chain comprises a second variable region, and wherein the second variable region comprises a sequence that has at least 90% identity to the amino acid sequence set forth in SEQ ID NO: 20, and (c) wherein the antibody interacts with OPGL.

In other aspects, the first variable region comprises a sequence that has at least 95% identity to the amino acid sequence set forth in SEQ ID NO: 18, and the second variable region comprises a sequence that has at least 95% identity to the amino acid sequence set forth in SEQ ID NO: 20.

In still other aspects, the first variable region comprises a sequence that has at least 99% identity to the amino acid sequence set forth in SEQ ID NO: 18, and the second variable region comprises a sequence that has at least 99% identity to the amino acid sequence set forth in SEQ ID NO: 20.

The invention also provides antibodies that specifically bind OPGL, wherein the heavy chain comprises an amino acid sequence as set forth in SEQ ID NO: 34, or an antigen-binding or an immunologically functional immunoglobulin fragment thereof, and the light chain comprises a light chain variable region comprising an amino acid sequence as set forth in SEQ ID NO: 36, or an antigen-binding or an immunologically functional immunoglobulin fragment thereof.

The invention provides antibodies that specifically bind OPGL, wherein the heavy chain comprises an amino acid sequence as set forth in SEQ ID NO: 42, or an antigen-binding or an immunologically functional immunoglobulin fragment thereof, and the light chain comprises a light chain variable region comprising an amino acid sequence as set forth in SEQ ID NO: 44, or an antigen-binding or an immunologically functional immunoglobulin fragment thereof.

The invention also provides single chain antibodies, single chain Fv antibodies, Fab antibodies, Fab' antibodies, and (Fab')$_2$.

In particular aspects, the invention provides a heavy chain comprising a variable region and a constant region, wherein the variable region comprises an amino acid sequence as set forth in any of SEQ ID NO: 6, SEQ ID NO: 10, SEQ ID NO: 14, SEQ ID NO: 18, SEQ ID NO: 22, or SEQ ID NO: 26, or an antigen-binding or an immunologically functional immunoglobulin fragment thereof.

In addition, the invention also provides a heavy chain comprising an amino acid sequence as set forth in any of SEQ ID NO: 30, SEQ ID NO: 34, SEQ ID NO: 38, SEQ ID NO: 42, SEQ ID NO: 46, or SEQ ID NO: 50, or an antigen-binding or an immunologically functional immunoglobulin fragment thereof.

In certain aspects, the invention provides a light chain comprising a variable region and a constant region, wherein the variable region comprises an amino acid sequence as set forth in any of SEQ ID NO: 8, SEQ ID NO: 12, SEQ ID NO: 16, SEQ ID NO: 20, SEQ ID NO: 24, or SEQ ID NO: 28, or an antigen-binding or an immunologically functional immunoglobulin fragment thereof.

In other aspects, the invention provides a light chain comprising an amino acid sequence as set forth in any of SEQ ID NO: 32, SEQ ID NO: 36, SEQ ID NO: 40, SEQ ID NO: 44, SEQ ID NO: 48, or SEQ ID NO: 52, or an antigen-binding or an immunologically functional immunoglobulin fragment thereof.

The invention also relates to isolated human antibodies that specifically bind OPGL, wherein the antibody comprises: (a) human heavy chain framework regions, a human heavy chain CDR1 region, a human heavy chain CDR2 region, and a human heavy chain CDR3 region; and (b) human light chain framework regions, a human light chain CDR1 region, a human light chain CDR2 region, and a human light chain CDR3 region. In certain aspects, the human heavy chain CDR1 region can be the heavy chain CDR1 region of 16E1, 2D8, 22B3, or 9H7 as shown in FIG. 15 and the human light chain CDR1 region can be the light chain CDR1 region of 16E1, 2D8, 22B3, or 9H7 as shown in FIG. 16. In other aspects, the human heavy chain CDR2 region can be the heavy chain CDR2 region of 16E1, 2D8, 22B3, or 9H7 as shown in FIG. 15 and the human light chain CDR2 region can be the light chain CDR2 region of 16E1, 2D8, 22B3, or 9H7 as shown in FIG. 16. In still other aspects, the human heavy chain CDR3 region is the heavy chain CDR3 region of 16E1, 2D8, 22B3, or 9H7 as shown in FIG. 15, and the human light chain CDR3 region is the light chain CDR3 region of 16E1, 2D8, 22B3, or 9H7 as shown in FIG. 16.

The invention also relates to isolated human antibodies that specifically bind OPGL, wherein the antibody comprises: (a) human heavy chain framework regions, a human heavy chain CDR1 region, a human heavy chain CDR2 region, and a human heavy chain CDR3 region; and (b) human light chain framework regions, a human light chain CDR1 region, a human light chain CDR2 region, and a human light chain CDR3 region. In certain aspects, the human heavy chain CDR1 region can be the heavy chain CDR1 region of 2E11 or 18B2 as shown in FIG. 15 and the human light chain CDR1 region can be the light chain CDR1 region of 2E11 or 18B2 as shown in FIG. 16. In other aspects, the human heavy chain CDR2 region can be the heavy chain CDR2 region of 2E11 or 18B2 as shown in FIG. 15 and the human light chain CDR2 region can be the light chain CDR2 region of 2E11 or 18B2 as shown in FIG. 16. In still other aspects, the human heavy chain CDR3 region is the heavy chain CDR3 region of 2E11 or 18B2 as shown in FIG. 15, and the human light chain CDR3 region is the light chain CDR3 region of 2E11 or 18B2 as shown in FIG. 16.

In addition, the invention provides methods for treating an osteopenic disorder, comprising the step of administering a pharmaceutically effective amount of a monoclonal antibody of the invention or antigen-binding fragment thereof to an individual in need thereof.

The invention further relates to fusion proteins and other molecules capable of binding to a region of osteoprotegerin ligand (OPGL) that is outside the D-E loop region, or both a region of OPGL that is outside the D-E loop region and all or a portion of the D-E loop region, wherein binding is consecutive or simultaneous (together with the aformentioned antibodies, collectively referred to herein as "specific binding partners"), such as may be prepared using methods as described, for example, in WO 00/24782, which is incorporated by reference. Such molecules can be expressed, for example, in mammalian cells (e.g. Chinese Hamster Ovary cells) or bacterial cells (e.g. *E. coli* cells).

The invention also provides methods for detecting the level of OPGL in a biological sample, comprising the step of contacting the sample with a monoclonal antibody of the invention or antigen-binding fragment thereof. The anti-OPGL antibodies of the invention may be employed in any known assay method, such as competitive binding assays, direct and indirect sandwich assays, immunoprecipitation assays and enzyme-linked immunosorbent assays (ELISA) (See, Sola, 1987, *Monoclonal Antibodies: A Manual of Techniques*, pp. 147-158, CRC Press, Inc.) for the detection and quantitation of OPGL. The antibodies can bind OPGL with an affinity that is appropriate for the assay method being employed.

Specific preferred embodiments of the present invention will become evident from the following more detailed description of certain preferred embodiments and the claims.

BRIEF DESCRIPTION OF THE FIGURES

FIGS. 1A-1B depict a cDNA sequence (FIG. 1A) encoding the anti-OPGL antibody heavy chain constant region (SEQ ID NO: 1) and the amino acid sequence (FIG. 1B) of the anti-OPGL antibody heavy chain constant region (SEQ ID NO: 2).

FIGS. 2A-2B depict a cDNA sequence (FIG. 2A) encoding the anti-OPGL antibody kappa chain constant region (SEQ ID NO: 3) and the amino acid sequence (FIG. 2B) of the anti-OPGL antibody kappa chain constant region (SEQ ID NO: 4).

FIGS. 3A-3B depict a cDNA sequence (FIG. 3A) encoding the 22B3 anti-OPGL antibody heavy chain variable region (SEQ ID NO: 5) and the amino acid sequence (FIG. 3B) of the 22B3 anti-OPGL antibody heavy chain variable region (SEQ ID NO: 6).

FIGS. 4A-4B depict a cDNA sequence (FIG. 4A) encoding the 22B3 anti-OPGL antibody kappa chain variable region (SEQ ID NO: 7) and the amino acid sequence (FIG. 4B) of the 22B3 anti-OPGL antibody kappa chain variable region (SEQ ID NO: 8).

FIGS. 5A-5B depict a cDNA sequence (FIG. 5A) encoding the 2E11 anti-OPGL antibody heavy chain variable region (SEQ ID NO: 9) and the amino acid sequence (FIG. 5B) of the 2E11 anti-OPGL antibody heavy chain variable region (SEQ ID NO: 10).

FIGS. 6A-6 depict a cDNA sequence (FIG. 6A) encoding the 2E11 anti-OPGL antibody kappa chain variable region (SEQ ID NO: 11) and the amino acid sequence (FIG. 6B) of the 2E11 anti-OPGL antibody kappa chain variable region (SEQ ID NO: 12).

FIGS. 7A-7B depict a cDNA sequence (FIG. 7A) encoding the 2D8 anti-OPGL antibody heavy chain variable region (SEQ ID NO: 13) and the amino acid sequence (FIG. 7B) of the 2D8 anti-OPGL antibody heavy chain variable region (SEQ ID NO: 14).

FIGS. 8A-8B depict a cDNA sequence (FIG. 8A) encoding the 2D8 anti-OPGL antibody kappa chain variable region (SEQ ID NO: 15) and the amino acid sequence (FIG. 8B) of the 2D8 anti-OPGL antibody kappa chain variable region (SEQ ID NO: 16).

FIGS. 9A-9B depict a cDNA sequence (FIG. 9A) encoding the 18B2 anti-OPGL antibody heavy chain variable region (SEQ ID NO: 17) and the amino acid sequence (FIG. 9B) of the 18B2 anti-OPGL antibody heavy chain variable region (SEQ ID NO: 18).

FIGS. 10A-10B depict a cDNA sequence (FIG. 10A) encoding the 18B2 anti-OPGL antibody kappa chain variable region (SEQ ID NO: 19) and the amino acid sequence (FIG. 10B) of the 18B2 anti-OPGL antibody kappa chain variable region (SEQ ID NO: 20).

FIGS. 11A-11B depict a cDNA sequence (FIG. 11A) encoding the 16E1 anti-OPGL antibody heavy chain variable region (SEQ ID NO: 21) and the amino acid sequence (FIG. 11B) of the 16E1 anti-OPGL antibody heavy chain variable region (SEQ ID NO: 22).

FIGS. 12A-12B depict a cDNA sequence (FIG. 12A) encoding the 16E1 anti-OPGL antibody kappa chain variable region (SEQ ID NO: 23) and the amino acid sequence (FIG. 12B) of the 16E1 anti-OPGL antibody kappa chain variable region (SEQ ID NO: 24).

FIGS. 13A-13B depict a cDNA sequence (FIG. 13A) encoding the 9H7 anti-OPGL antibody heavy chain variable region (SEQ ID NO: 25) and the amino acid sequence (FIG. 13B) of the 9H7 anti-OPGL antibody heavy chain variable region (SEQ ID NO: 26).

FIGS. 14A-14B depict a cDNA sequence (FIG. 14A) encoding the 9H7 anti-OPGL antibody kappa chain variable region (SEQ ID NO: 27) and the amino acid sequence (FIG. 14B) of the 9H7 anti-OPGL antibody kappa chain variable region (SEQ ID NO: 28).

FIG. 15 depicts the heavy chain alignment for anti-OPGL antibodies designated 16E1 (SEQ ID NO: 22), 2E11 (SEQ ID NO: 10), 18B2 (SEQ ID NO: 18), 2D8 (SEQ ID NO:14), 22B3 (SEQ ID NO: 6), and 9H7 (SEQ ID NO: 26). CDRs are underlined, non-consensus amino acids are shaded and in bold type.

16E1: heavy chain CDR1 is SEQ ID NO: 77, CDR2 is SEQ ID NO: 78, CDR3 is SEQ ID NO: 79.

2E11: heavy chain CDR1 is SEQ ID NO: 80, CDR2 is SEQ ID NO: 81, CDR3 is SEQ ID NO: 82.

18B2: heavy chain CDR1 is SEQ ID NO: 83, CDR2 is SEQ ID NO: 84, CDR3 is SEQ ID NO: 82.

2D8: heavy chain CDR1 is SEQ ID NO: 85, CDR2 is SEQ ID NO: 86, CDR3 is SEQ ID NO: 87.

22B3: heavy chain CDR1 is SEQ ID NO: 88, CDR2 is SEQ ID NO: 89, CDR3 is SEQ ID NO: 90.

9H7: heavy chain CDR1 is SEQ ID NO: 88, CDR2 is SEQ ID NO: 89, CDR3 is SEQ ID NO: 91.

FIG. 16 depicts the light chain alignment for anti-OPGL antibodies designated 16E1 (SEQ ID NO: 24), 2E11 (SEQ ID NO: 12), 18B2 (SEQ ID NO: 20), 2D8 (SEQ ID NO: 16), 22B3 (SEQ ID NO: 8), and 9H7 (SEQ ID NO: 28). CDRs are underlined, non-consensus amino acids are shaded and in bold type.

16E1: light chain CDR1 is SEQ ID NO: 92, CDR 2 is SEQ ID NO: 93, CDR3 is SEQ ID NO: 94.

2E11: light chain CDR1 is SEQ ID NO: 95, CDR 2 is SEQ ID NO: 93, CDR3 is SEQ ID NO: 94.

18B2: light chain CDR1 is SEQ ID NO: 96, CDR 2 is SEQ ID NO: 97, CDR3 is SEQ ID NO: 98.

2D8: light chain CDR1 is SEQ ID NO: 96, CDR 2 is SEQ ID NO: 97, CDR3 is SEQ ID NO: 98.

22B3: light chain CDR1 is SEQ ID NO: 99, CDR 2 is SEQ ID NO: 97, CDR3 is SEQ ID NO: 100.

9H7: light chain CDR1 is SEQ ID NO: 101, CDR 2 is SEQ ID NO: 97, CDR3 is SEQ ID NO: 102.

Figure 17:
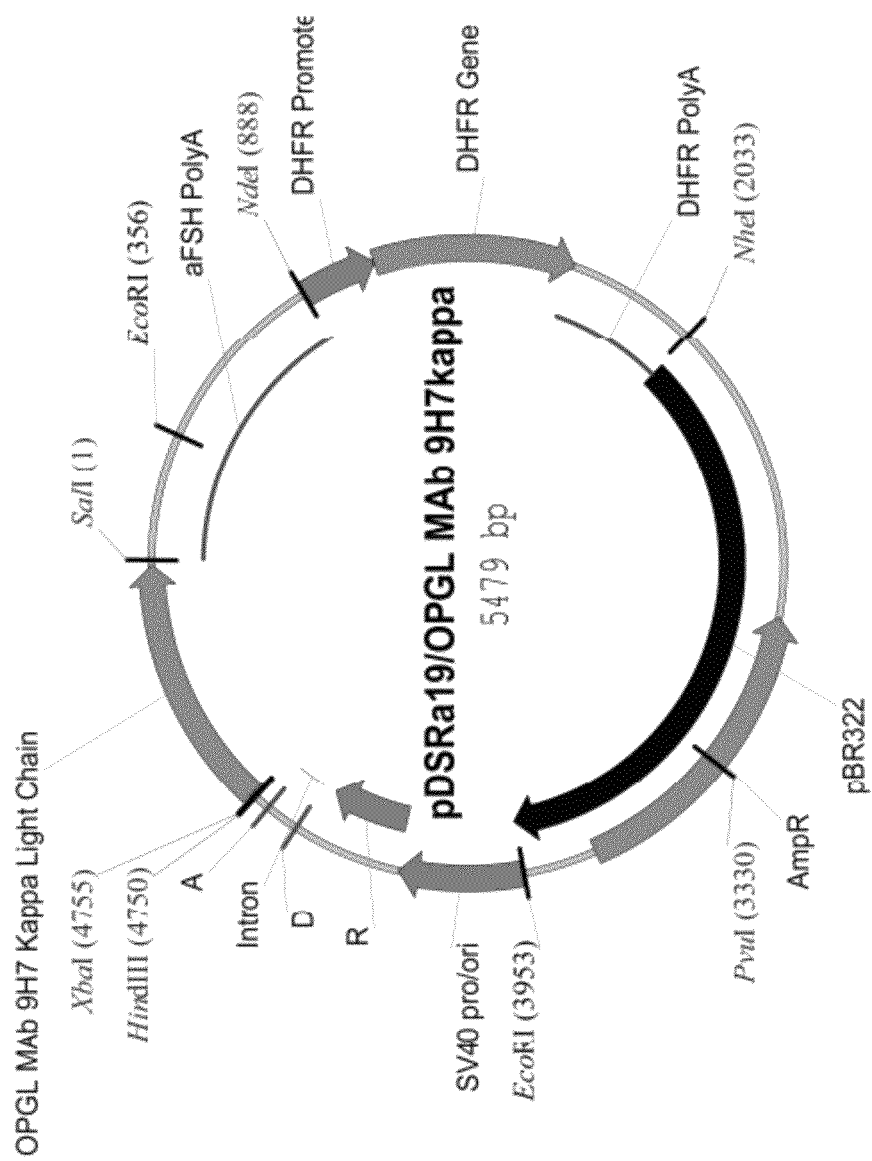

FIG. 17 depicts a circular plasmid map of the pDSRα19:9H7 kappa chain expression vector.

Figure 18:
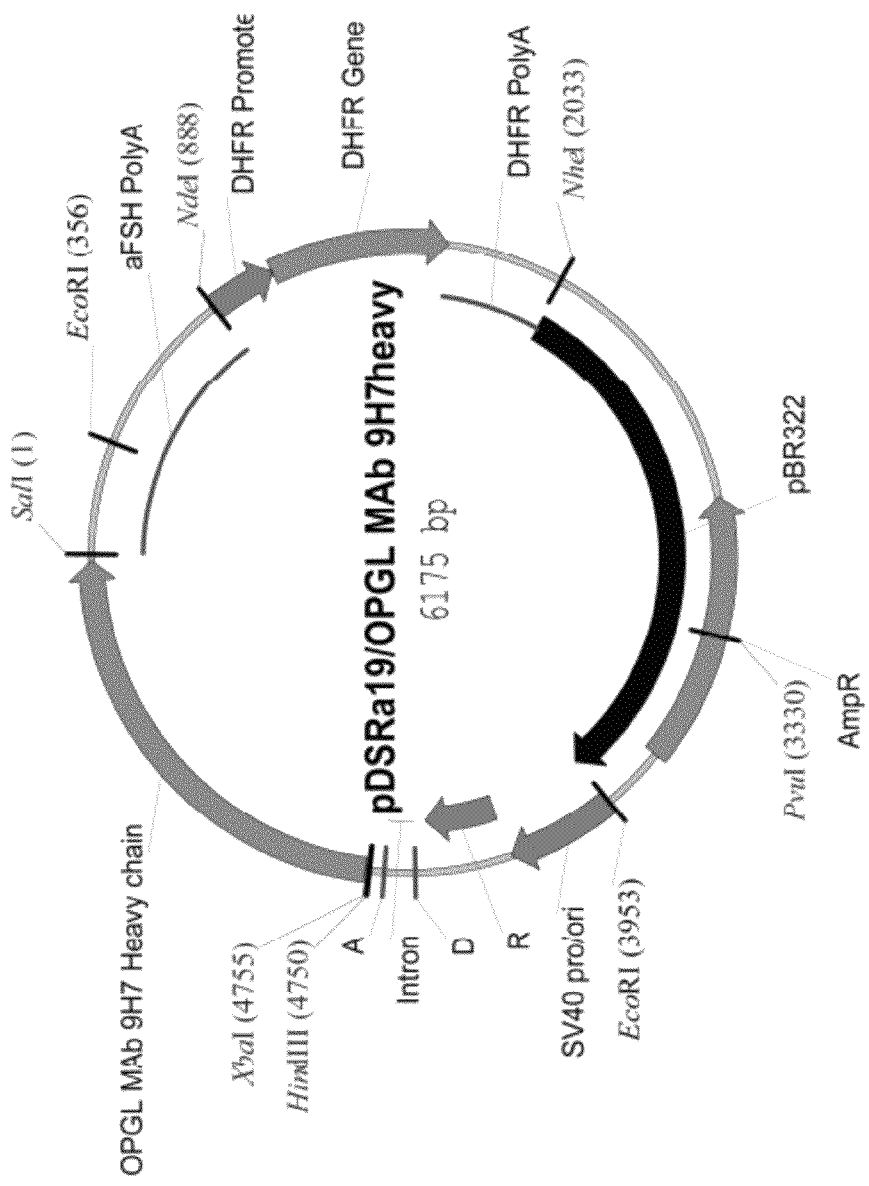

FIG. 18 shows a circular plasmid map of the pDSRα19:9H7 heavy chain expression vector.

Figure 19:
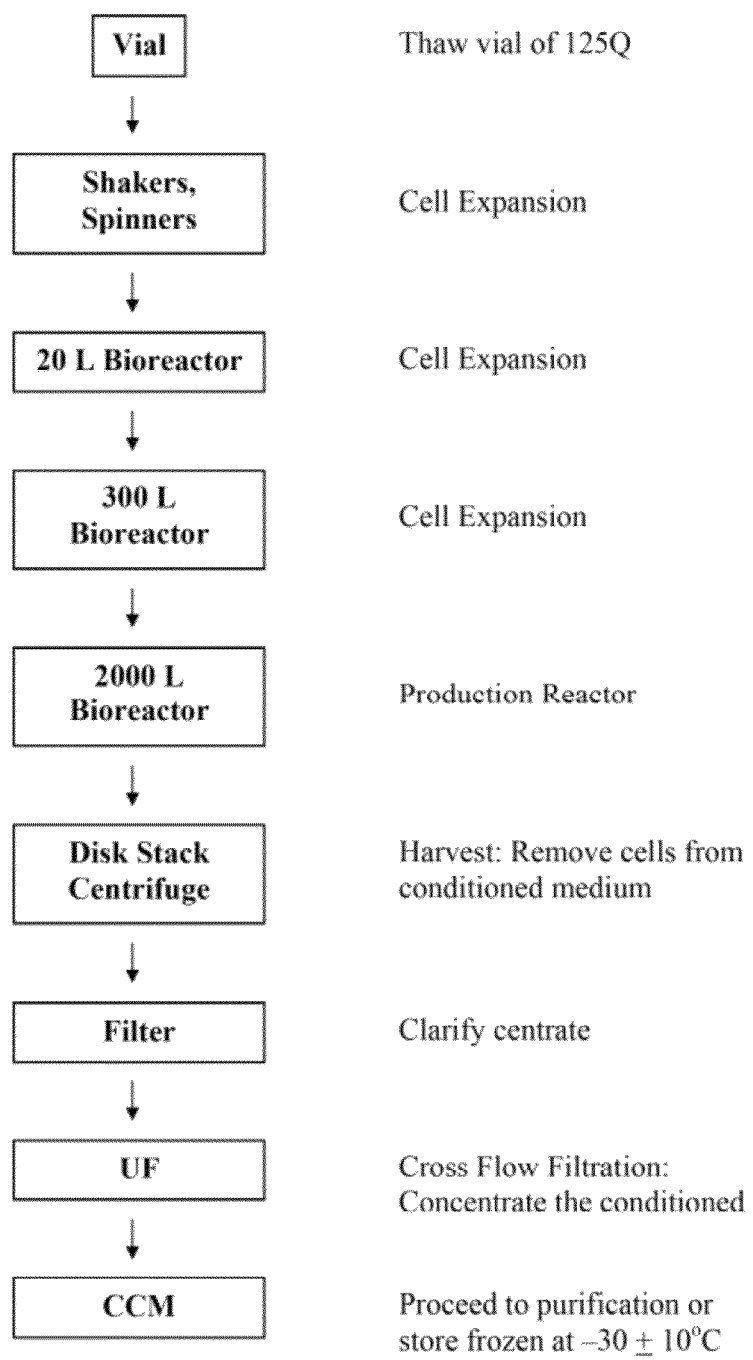

FIG. 19 depicts an exemplary cell culture process for producing anti-OPGL antibody.

Figure 20:
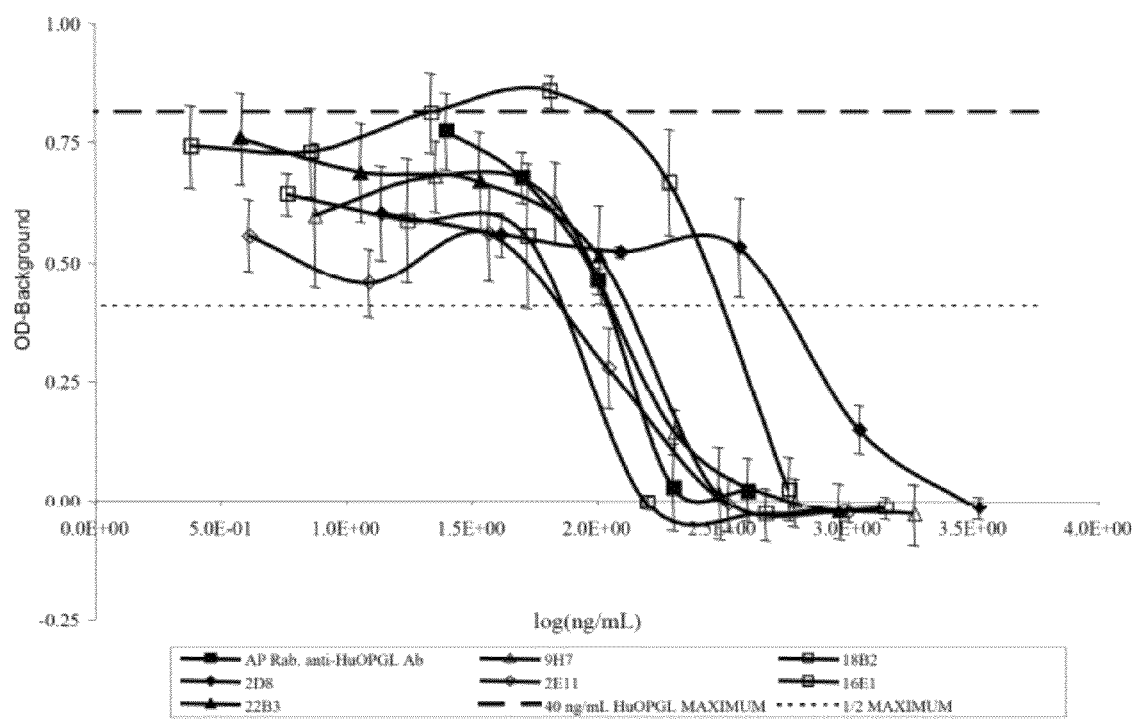

FIG. 20 is a graph showing optical density versus anti-OPGL antibody concentration demonstrating OPGL antibody mediated inhibition of osteoclast formation.

Figure 21:
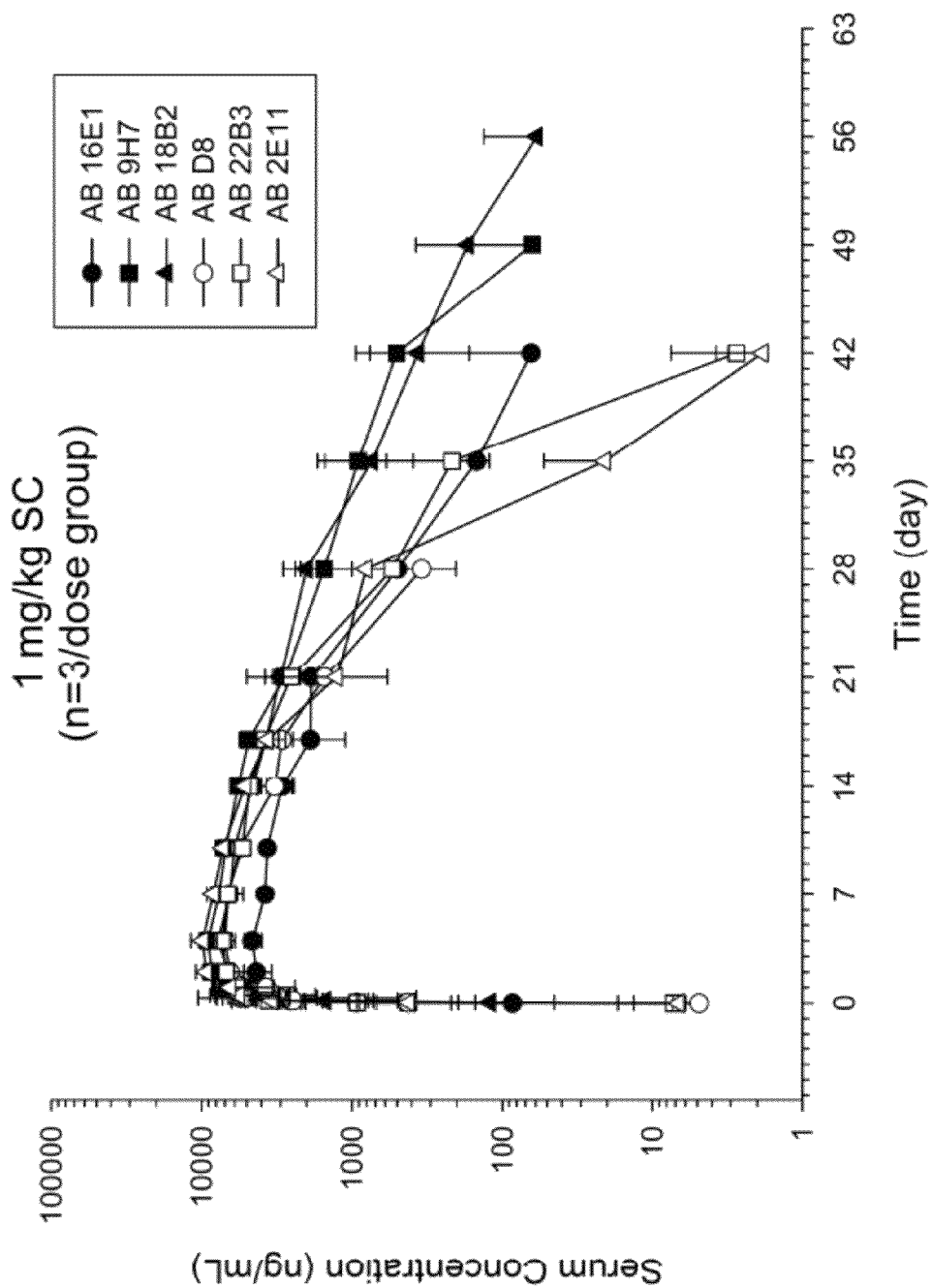

FIG. 21 depicts graphs of serum concentrations of anti-OPGL antibodies following subcutaneous administration at 1.0 mg/kg in Cynomolgus monkeys.

Figure 22:
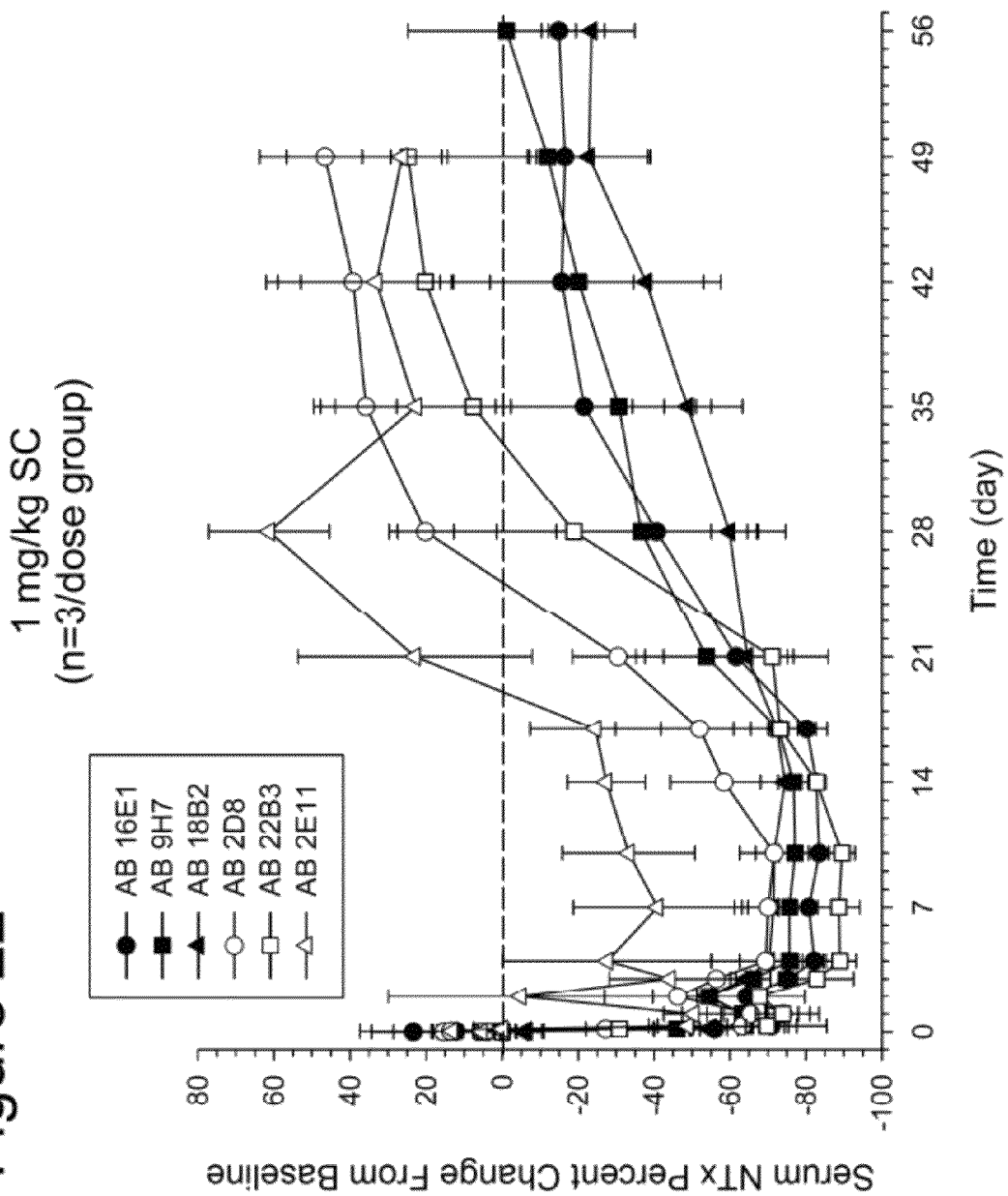

FIG. 22 depicts graphs representing the percentage change in serum NTx from baseline following subcutaneous administration at 1.0 mg/kg of anti-OPGL antibodies in Cynomolgus monkeys.

FIG. 23 shows a comparison of murine (SEQ ID NO: 70), human (SEQ ID NO: 71), and murine DE variant (SEQ ID NO: 72) amino acid sequences in a region of OPGL between the D and E regions.

Figure 24:
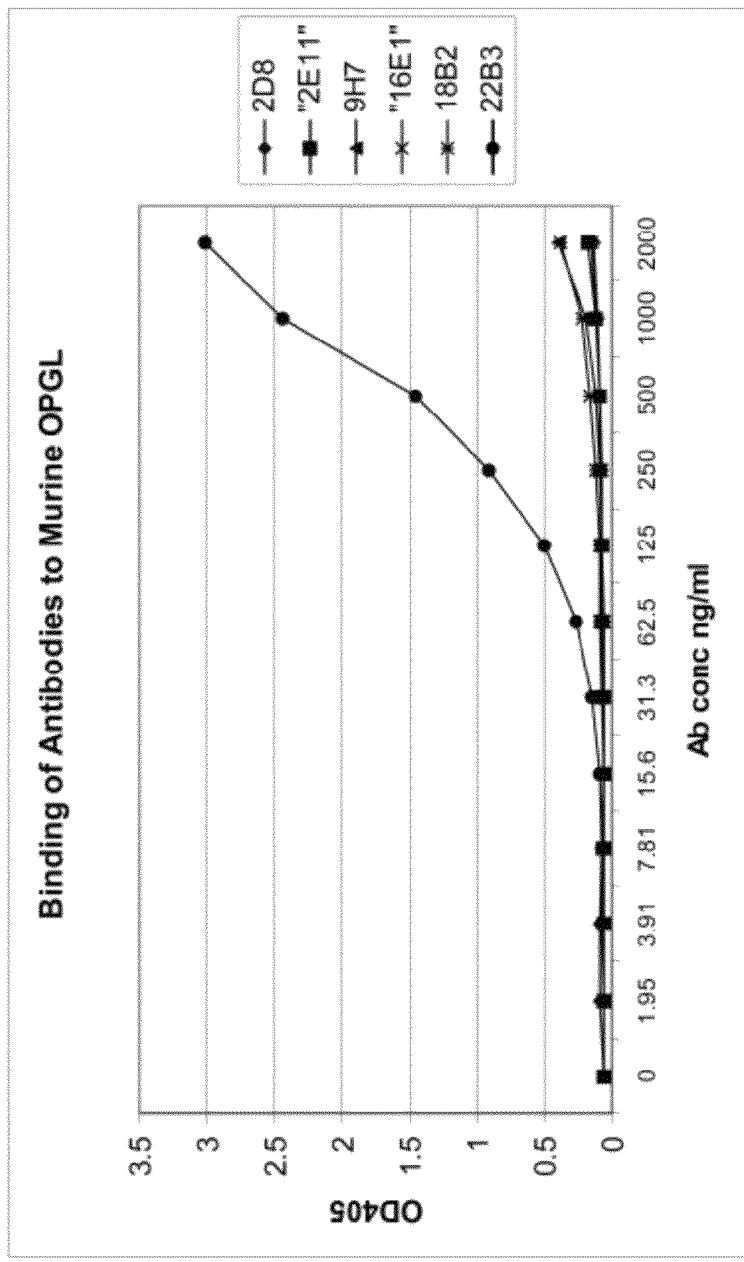

FIG. 24 depicts the results of an enzyme immunoassay showing six anti-OPGL antibodies of the invention binding murine OPGL (143-317).

Figure 25:
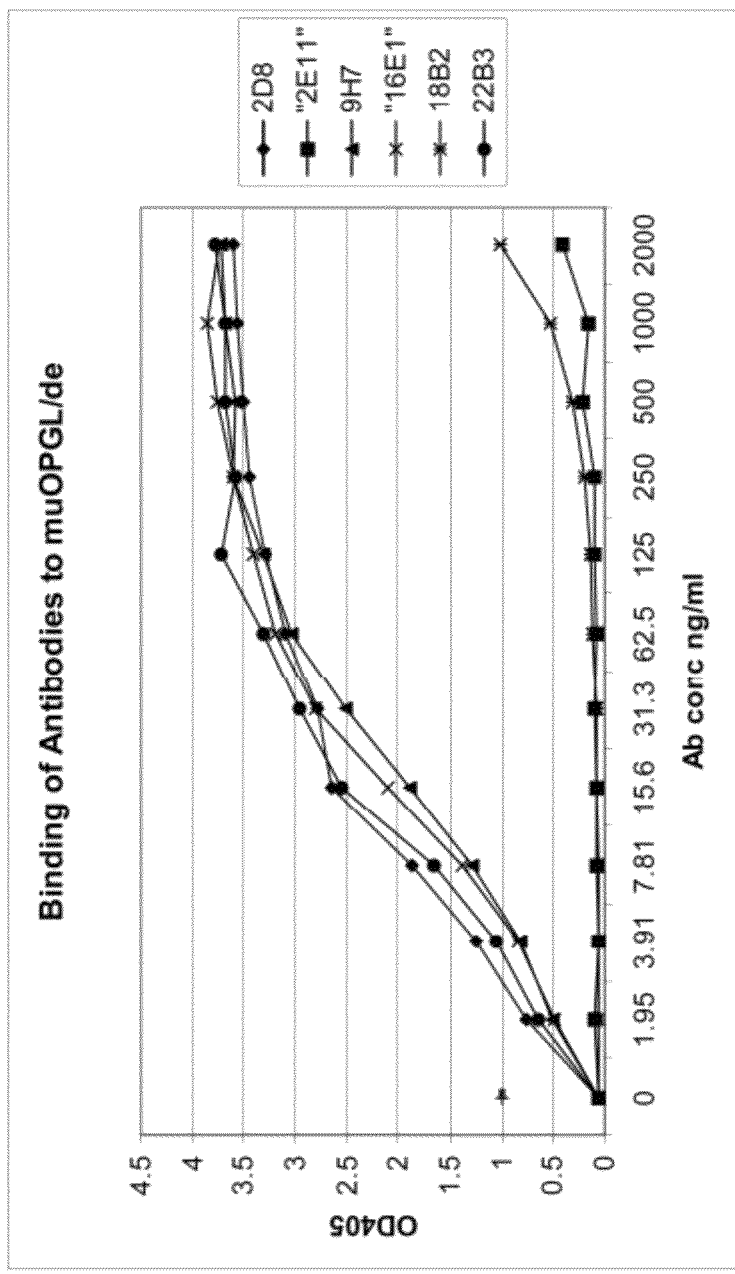

FIG. 25 depicts the results of an enzyme immunoassay showing four of the anti-OPGL antibodies of the invention bind FLAG-murine OPGL/DE (158-316).

DETAILED DESCRIPTION OF PREFERRED EMBODIMENTS

The section headings used herein are for organizational purposes only and are not to be construed as limiting the subject matter described. All references cited in this application are expressly incorporated by reference herein for any purpose.

Definitions

Standard techniques were used for recombinant DNA, oligonucleotide synthesis, and tissue culture and transformation (e.g., electroporation, lipofection). Enzymatic reactions and purification techniques were performed according to manufacturer's specifications or as commonly accomplished in the art or as described herein. The foregoing techniques and procedures were generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein means a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide which it is not linked to in nature, or (3) does not occur in nature as part of a larger sequence.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise).

The terms "polypeptide" or "protein" means molecules having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass anti-OPGL antibodies, or sequences that have deletions from, additions to, and/or substitutions of one or more amino acid of an anti-OPGL antibody.

The term "polypeptide fragment" refers to a polypeptide that has an amino-terminal deletion, a carboxyl-terminal deletion, and/or an internal deletion. In certain embodiments, fragments are at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains. In the case of an anti-OPGL antibody, useful fragments include but are not limited to a CDR region, a variable domain of a heavy or light chain, a portion of an antibody chain or just its variable region including two CDRs, and the like.

The term "immunologically functional immunoglobulin fragment" as used herein refers to a polypeptide fragment that contains at least the CDRs of the immunoglobulin heavy and light chains. An immunologically functional immunoglobulin fragment of the invention is capable of binding to an antigen. In preferred embodiments, the antigen is a ligand that specifically binds to a receptor. In these embodiments, binding of an immunologically functional immunoglobulin fragment of the invention prevents binding of the ligand to its receptor, interrupting the biological response resulting from ligand binding to the receptor. Preferably, an immunologically functional immunoglobulin fragment of the invention binds specifically to OPGL. Most preferably, the fragment binds specifically to human OPGL.

The term "naturally-occurring" as used herein and applied to an object refers to the fact that the object can be found in nature. For example, a polypeptide or polynucleotide sequence that is present in an organism (including viruses) that can be isolated from a source in nature and that has not been intentionally modified by man is naturally occurring.

The term "operably linked" means that the components to which the term is applied are in a relationship that allows them to carry out their inherent functions under suitable conditions. For example, a control sequence "operably linked" to a coding sequence is ligated thereto so that expression of the protein coding sequence is achieved under conditions compatible with the transcriptional activity of the control sequences.

The term "control sequence" as used herein refers to polynucleotide sequences that can effect expression, processing or intracellular localization of coding sequences to which they are ligated. The nature of such control sequences may differ depending upon the host organism. In particular embodiments, control sequences for prokaryotes may include promoter, ribosomal binding site, and transcription termination sequence. In other particular embodiments, control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phosoraniladate and phosphoroamidate. The term "polynucleotide" specifically includes single and double stranded forms of DNA.

The term "oligonucleotide" as used herein includes naturally occurring, and modified nucleotides linked together by naturally occurring, and/or non-naturally occurring oligonucleotide linkages. Oligonucleotides are a polynucleotide subset comprising members that are generally single-stranded and have a length of 200 bases or fewer. In certain embodiments, oligonucleotides are 10 to 60 nucleotides in length. In certain embodiments, oligonucleotides are 12, 13, 14, 15, 16, 17, 18, 19, or 20 to 40 nucleotides in length. Oligonucleotides may be single stranded or double stranded, e.g. for use in the construction of a gene mutant. Oligonucleotides of the invention may be sense or antisense oligonucleotides with reference to a protein-coding sequence.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.* 14: 9081; Stec et al., 1984, *J. Am. Chem. Soc.* 106: 6077; Stein et al., 1988, *Nucl. Acids Res.* 16: 3209; Zon et al., 1991, *Anti-Cancer Drug Design* 6: 539; Zon et al., 1991, OLIGONUCLEOTIDES AND ANALOGUES: A PRACTICAL APPROACH, (F. Eckstein, ed.), Oxford University Press, Oxford England, pp. 87-108; Stec et al., U.S. Pat. No. 5,151,510; Uhlmann and Peyman, 1990, *Chemical Reviews* 90: 543, the disclosures of each of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or that is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52: 456; Sambrook et al., 2001, ibid.; Davis et al., 1986, BASIC METHODS IN MOLECULAR BIOLOGY (Elsevier); and Chu et al., 1981, *Gene* 13: 197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "identity," as known in the art, refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is used in the art with regard to a related concept, but in contrast to "identity," "similarity" refers to a measure of relatedness, which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related and polypeptides can be readily calculated by known methods. Such methods include, but are not limited to, those described in COMPUTATIONAL MOLECULAR BIOLOGY, (Lesk, A. M., ed.), 1988, New York: Oxford University Press; BIOCOMPUTING: INFORMATICS AND GENOME PROJECTS, (Smith, D. W., ed.), 1993, New York: Academic Press; COMPUTER ANALYSIS OF SEQUENCE DATA, PART 1, (Griffin, A. M., and Griffin, H. G., eds.), 1994, New Jersey: Humana Press; von Heinje, G., 1987, SEQUENCE ANALYSIS IN MOLECULAR BIOLOGY, New York: Academic Press; SEQUENCE ANALYSIS PRIMER, (Gribskov, M. and Devereux, J., eds.), 1991, New York: M. Stockton Press; and Carillo et al., 1988, *SIAM J. Applied Math.* 48:1073; and Durbin et al., 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.* 12:387; Genetics Computer Group, University of Wisconsin, Madison, Wis., BLASTP, BLASTN, and FASTA, Altschul et al., 1990, *J. Mol. Biol.* 215: 403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as three times the average diagonal, wherein the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM 250 or BLOSUM 62 are used in conjunction with the algorithm. In certain embodiments, a standard comparison matrix (see Dayhoff et al., 1978, *Atlas of Protein Sequence and Structure* 5:345-352 for the PAM 250 comparison matrix; Henikoff et al., 1992, *Proc. Natl. Acad. Sci. USA* 89: 10915-10919 for the BLOSUM 62 comparison matrix) is also used by the algorithm.

In certain embodiments, the parameters for a polypeptide sequence comparison include the following:

Algorithm: Needleman et al., 1970, *J. Mol. Biol.* 48:443-453;

Comparison matrix: BLOSUM 62 from Henikoff et al., 1992, supra;

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See IMMUNOLOGY—A SYNTHESIS, 2nd Edition, (E. S. Golub and D. R. Gren, Eds.), 1991, Sinauer Associates, Sunderland, Mass., which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn, 1,4 Diamine-butyric Acid | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art can identify suitable areas of the molecule that can be changed without destroying activity by targeting regions not believed to be important for activity. In other embodiments, the skilled artisan can identify residues and portions of the molecules that are conserved among similar polypeptides. In further embodiments, even areas that are important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants can be used to gather information about suitable variants. For example, if it was discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Molt, 1996, *Curr. Op. in Biotech.* 7: 422-427; Chou et al., 1974, *Biochemistry* 13: 222-245; Chou et al., 1974, *Biochemistry* 113: 211-222; Chou et al., 1978, *Adv. Enzymol. Relat. Areas Mol. Biol.* 47: 45-148; Chou et al., 1978, *Ann. Rev. Biochem.* 47: 251-276 and Chou et al., 1979, *Biophys. J.* 26: 367-384. Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, *Nucl. Acid. Res.* 27: 244-247. It has been suggested (Brenner et al., 1997, *Curr. Op. Struct. Biol.* 7: 369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7: 377-87; Sippl et al., 1996, *Structure* 4: 15-19), "profile analysis" (Bowie et al., 1991, *Science* 253: 164-170; Gribskov et al., 1990, *Meth. Enzym.* 183: 146-159; Gribskov et al., 1987, *Proc. Nat. Acad. Sci. USA* 84: 4355-4358), and "evolutionary linkage" (See Holm, 1999, supra, and Brenner, 1997, supra).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. Also provided are rearrangements of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues in the parent or native amino acid sequence are deleted from or substituted for another amino acid (e.g., serine). Cysteine variants are useful, inter alia when antibodies must be refolded into a biologically active conformation, for example, after the isolation of insoluble inclusion bodies. Cysteine variants generally have fewer cysteine residues than the native protein, and typically have an even number to minimize interactions resulting from unpaired cysteines.

In additional embodiments, antibody variants can include antibodies comprising a modified Fc fragment or a modified heavy chain constant region. An Fc fragment, which stands for "fragment that crystallizes," or a heavy chain constant region can be modified by mutation to confer on an antibody altered binding characteristics. See, for example, Burton and Woof, 1992, *Advances in Immunology* 51: 1-84; Ravetch and Bolland, 2001, *Annu. Rev. Immunol.* 19: 275-90; Shields et al., 2001, *Journal of Biol. Chem* 276: 6591-6604; Telleman and Junghans, 2000, *Immunology* 100: 245-251; Medesan et al., 1998, *Eur. J. Immunol.* 28: 2092-2100; all of which are incorporated herein by reference). Such mutations can include substitutions, additions, deletions, or any combination thereof, and are typically produced by site-directed mutagenesis using one or more mutagenic oligonucleotide(s) according to methods described herein, as well as according to methods known in the art (see, for example, Maniatis et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

According to certain embodiments, amino acid substitutions are those that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES (Creighton, Ed.), 1984, W. H. New York: Freeman and Company; INTRODUCTION TO PROTEIN STRUCTURE (Branden and Tooze, eds.), 1991, New York: Garland Publishing; and Thornton et at., 1991, *Nature* 354: 105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". Fauchere, 1986, *Adv. Drug Res.* 15: 29; Veber and Freidinger, 1985, *TINS p.* 392; and Evans et al., 1987, *J. Med. Chem.* 30: 1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch, 1992, *Ann. Rev. Biochem.* 61: 387), incorporated herein by reference for any purpose); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. In certain embodiments, binding fragments are produced by recombinant DNA techniques. In certain embodiments, binding fragments are produced by enzymatic or chemical cleavage of intact antibodies. Binding fragments include, but are not limited to, Fab, Fab', F(ab')$_2$, Fv, and single-chain antibodies.

The term "heavy chain" includes any immunoglobulin polypeptide having a heavy chain constant region and sufficient variable region sequence to confer specificity for an OPGL. The term "light chain" includes any immunoglobulin polypeptide having a light chain constant region and sufficient variable region sequence to confer specificity for an OPGL. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. A F(ab) fragment is comprised of one light chain and the $C_H1$ and variable regions of one heavy chain. The heavy chain of a F(ab) molecule cannot form a disulfide bond with another heavy chain molecule. A F(ab') fragment contains one light chain and one heavy chain that contains more of the constant region, between the $C_H1$ and $C_H2$ domains, such that an interchain disulfide bond can be formed between two heavy chains to form a F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain that forms an antigen-binding region. Single chain antibodies are discussed in detail in WO 88/01649 and U.S. Pat. Nos. 4,946,778 and 5,260,203 incorporate by reference.

A bivalent antibody other than a "multispecific" or "multifunctional" antibody, in certain embodiments, is understood to comprise binding sites having identical antigenic specificity.

In assessing antibody binding and specificity according to the invention, an antibody substantially inhibits adhesion of a ligand to a receptor when an excess of antibody reduces the quantity of ligand bound to receptor by at least about 20%, 40%, 60%, 80%, 85%, or more (as measured in an in vitro competitive binding assay).

The term "epitope" includes any polypeptide determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In certain embodiments, an antibody is said to specifically bind an antigen when the dissociation constant is $\leq 10^{-8}$ M, in certain embodiments, when the dissociation constant is $\leq 10$ M, and in certain embodiments, when the dissociation constant is $\leq 10^{-10}$ M.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by labeled avidin (e.g., streptavidin preferably comprising a detectable marker such as a fluorescent marker, a chemiluminescent marker or an enzymatic activity that can be detected by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^3$H, $^{14}$C, $^{15}$N, $^{35}$S, $^{90}$Y, $^{99m}$Tc, $^{111}$In, $^{125}$I, $^{131}$I) fluorescent labels (e.g., fluorescein isothiocyanate or FITC, rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as (CH$_2$)$_n$, where n<about 20) of various lengths to reduce potential steric hindrance.

The term "biological sample", as used herein, includes, but is not limited to, any quantity of a substance from a living thing or formerly living thing. Such living things include, but are not limited to, m humans, mice, monkeys, rats, rabbits, and other animals. Such substances include, but are not limited to, blood, serum, urine, cells, organs, tissues, bone, bone marrow, lymph nodes, and skin.

The term "osteopenic disorder" includes, but is not limited to, osteoporosis, osteopenia, Paget's disease, lytic bone metastases, periodontitis, rheumatoid arthritis, and bone loss due to immobilization. In addition to these bone disorders, certain cancers are known to increase osteoclast activity and induce bone resorption, such as breast and prostate cancer and multiple myeloma. These cancers are now known to produce factors that result in the over-expression of OPGL in the bone, and lead to increased osteoclast numbers and activity.

The term "pharmaceutical agent or drug" as used herein refers to a chemical compound or composition capable of inducing a desired therapeutic effect when properly administered to a patient.

As used herein, "substantially pure" or "substantially purified" means a compound or species that is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The term "patient" includes human and animal subjects.

Unless otherwise required by context, singular terms shall include pluralities and plural terms shall include the singular.

The invention provides antibodies, preferably monoclonal antibodies and most preferably human antibodies, that are immunologically specific for osteoprotegerin ligand (OPGL), a member of the tumor necrosis factor (TNF) family of cytokines that is involved in the formation of osteoclasts. Increased osteoclast activity correlates with a number of osteopenic disorders, including post-menopausal osteoporosis, Paget's disease, lytic bone metastases, and rheumatoid arthritis. Thus, a reduction in OPGL activity may result in a decrease in osteoclast activity and may reduce the severity of osteopenic disorders. According to certain embodiments of the invention, antibodies directed to OPGL may be used detect, diagnose, prevent and treat osteopenic disorders, including by not limited to, those mentioned above.

In certain embodiments of the present invention, there is provided a fully human monoclonal antibody against human OPGL. In certain embodiments, nucleotide sequences encoding, and amino acid sequences comprising, heavy and light chain immunoglobulin molecules, particularly sequences corresponding to the variable regions, are provided. In certain embodiments, sequences corresponding to complementarity determining regions (CDR's), specifically from CDR1 through CDR3, are provided. According to certain embodiments, a hybridoma cell line expressing such an immunoglobulin molecule and monoclonal antibody is also provided. In certain embodiments, the invention provides purified human monoclonal antibody against human OPGL.

The ability to clone and reconstruct megabase-sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents provides unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study mechanisms underlying programmed expression and assembly of antibodies as well as their role in B-cell development. Furthermore, such a strategy provides a source for production of fully human monoclonal antibodies (MAbs). Fully human antibodies are expected to minimize the immunogenic and allergic responses intrinsic to mouse or mouse-derivatized MAbs, and to thereby increase the efficacy and safety of the administered antibodies. Fully human antibodies can be used in the treatment of chronic and recurring human diseases, such as osteoporosis, inflammation, autoimmunity, and cancer, the treatment thereof requiring repeated antibody administration. Thus, one particular advantage of the anti-OPGL antibodies of the invention is that the antibodies are fully human and can be administered to patients in a non-acute manner while minimizing adverse reactions commonly associated with human anti-mouse antibodies or other previously described non-fully human antibodies from non-human species.

One skilled in the art can engineer mouse strains deficient in mouse antibody production with large fragments of the human Ig loci so that the mice produce human but not mouse antibodies. Large human Ig fragments in mouse germline preserve variable gene diversity as well as the proper regulation of antibody production and expression. By exploiting the mouse machinery for antibody diversification and selection and the lack of immunological tolerance to human proteins, the reproduced human antibody repertoire in these mouse strains yield high affinity antibodies against any antigen of interest, including human antigens. Using hybridoma technology, antigen-specific human mAbs with the desired specificity can be produced and selected.

In certain embodiments, the skilled artisan can use constant regions from species other than human along with the human variable region(s) to produce chimeric antibodies.

Naturally Occurring Antibody Structure

Naturally occurring antibody structural units typically comprise a tetramer. Each such tetramer typically is composed of two identical pairs of polypeptide chains, each pair having one full-length "light" chain (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, $IgG_1$, $IgG_2$, $IgG_3$, and $IgG_4$. IgM has subclasses including, but not limited to, $IgM_1$ and $IgM_2$. IgA is similarly subdivided into subclasses including, but not limited to, $IgA_1$ and $IgA_2$. Within full-length light and heavy chains, typically, the variable and constant regions are joined by a "J" region of about 12 or more amino acids, with the heavy chain also including a "D" region of about 10 more amino acids. See, e.g., FUNDAMENTAL IMMUNOLOGY, 2nd ed., Ch. 7 (Paul, W., ed.) 1989, New York: Raven Press (incorporated by reference in its entirety for all purposes). The variable regions of each light/heavy chain pair typically form the antigen-binding site.

The variable regions typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (1987 and 1991, National Institutes of Health, Bethesda, Md.), or Chothia & Lesk, 1987, *J. Mol. Biol.* 196: 901-917; Chothia et al., 1989, *Nature* 342: 878-883.

Bispecific or Bifunctional Antibodies

A bispecific or bifunctional antibody typically is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, 1990, *Clin. Exp. Immunol.* 79: 315-321; Kostelny et al., 1992, *J. Immunol.* 148: 1547-1553.

Preparation of Antibodies

The invention provides antibodies that specifically bind to human OPGL. In certain embodiments, the antibodies can be produced by immunization with full-length OPGL or fragments thereof. The antibodies of the invention can be polyclonal or monoclonal, and/or may be recombinant antibodies. In preferred embodiments, antibodies of the invention are human antibodies prepared, for example, by immunization of transgenic animals capable of producing human antibodies (see, for example, PCT Published Application No. WO 93/12227).

The complementarity determining regions (CDRs) of the light and heavy chain variable regions of anti-OPGL antibody may be grafted to framework regions (FRs) from antibodies from the same, or another, species. In certain embodiments, the CDRs of the light and heavy chain variable regions of anti-OPGL antibody may be grafted to consensus human FRs. To create consensus human FRs, in certain embodiments, FRs from several human heavy chain or light chain amino acid sequences are aligned to identify a consensus amino acid sequence. In certain embodiments, the FRs of the anti-OPGL antibody heavy chain or light chain are replaced with the FRs from a different heavy chain or light chain. In certain embodiments, rare amino acids in the FRs of the heavy and light chains of anti-OPGL antibody are not replaced, while the rest of the FR amino acids are replaced. Rare amino acids are specific amino acids that are in positions in which they are not usually found in FRs. In certain embodiments, the grafted variable regions from anti-OPGL antibody may be used with a constant region that is different from the constant region of anti-OPGL antibody. In certain embodiments, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

Antibodies of the invention are prepared using transgenic mice that have a substantial portion of the human antibody producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the patents, applications, and references disclosed in the specification herein. In certain embodiments, the skilled worker may employ methods as disclosed in International Patent Application Publication No. WO 98/24893, which is hereby incorporated by reference for any purpose. See also Mendez et al., 1997, *Nature Genetics* 15: 146-156, which is hereby incorporated by reference for any purpose.

The monoclonal antibodies (mAbs) of the invention can be produced by a variety of techniques, including conventional monoclonal antibody methodology, e.g., the standard somatic cell hybridization technique of Kohler and Milstein, 1975, *Nature* 256: 495. Although somatic cell hybridization procedures are preferred, in principle, other techniques for producing monoclonal antibodies can be employed, e.g., viral or oncogenic transformation of B-lymphocytes.

The preferred animal system for preparing hybridomas is the mouse. Hybridoma production in the mouse is very well established, and immunization protocols and techniques for isolation of immunized splenocytes for fusion are well known in the art. Fusion partners (e.g., murine myeloma cells) and fusion procedures are also known.

In a preferred embodiment, human monoclonal antibodies directed against OPGL can be generated using transgenic mice carrying parts of the human immune system rather than the mouse system. These transgenic mice, referred to herein as "HuMab" mice, contain a human immunoglobulin gene minilocus that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg et al., 1994, *Nature* 368: 856-859). Accordingly, the mice exhibit reduced expression of mouse IgM or $\kappa$ and in response to immunization, the introduced human heavy and light chain transgenes, undergo class switching and somatic mutation to generate high affinity human IgG $\kappa$ monoclonal antibodies (Lonberg et al., supra.; Lonberg and Huszar, 1995, *Intern. Rev. Immunol.*, 13: 65-93; Harding and Lonberg, 1995, *Ann. N.Y. Acad. Sci* 764: 536-546). The preparation of HuMab mice is described in detail in Taylor et al., 1992, *Nucleic Acids Research,* 20: 6287-6295; Chen et al., 1993, *International Immunology* 5: 647-656; Tuaillon et al., 1994, *J. Immunol.* 152: 2912-2920; Lonberg et al., 1994, *Nature* 368: 856-859; Lonberg, 1994, *Handbook of Exp. Pharmacology* 113: 49-101; Taylor et al., 1994, *International Immunology* 6: 579-591; Lonberg and Huszar, 1995, *Intern. Rev. Immunol.* 13: 65-93; Harding and Lonberg, 1995, *Ann. N.Y. Acad. Sci.* 764: 536-546; Fishwild et al., 1996, *Nature Biotechnology* 14: 845-851, the contents of all of which are hereby incorporated by reference in their entirety. See further U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; International Publication Nos. WO 93/1227, published Jun. 24, 1993; WO 92/22646, published Dec. 23, 1992; WO 92/03918, published Mar. 19, 1992, the disclosures of all of which are hereby incorporated by reference in their entirety. Alternatively, the HCo7 and HCo12 transgenic mice strains described in the Examples below can be used to generate human anti-OPGL antibodies.

According to certain embodiments, fully human monoclonal antibodies specific for OPGL are produced as follows. Transgenic mice containing human immunoglobulin genes are immunized with the antigen of interest. Lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to OPGL is provided.

In certain embodiments of the invention, the antibodies bind to OPGL with a dissociation constant ($K_d$) of less than $10^{-8}$ M. In certain embodiments, the antibodies of the invention bind to OPGL with a $K_d$ of between approximately $10^{-8}$ M and $10^{-10}$ M.

In certain embodiments, the antibodies of the invention are of the $IgG_1$ isotype. In certain embodiments of the invention, the antibodies comprise a human kappa light chain and a human $IgG_1$ heavy chain. In certain embodiments, nucleic acid encoding the heavy and light chains comprising the antibodies of the invention were cloned for expression in mammalian cells. In certain embodiments, the variable regions of the antibodies are ligated to a constant region other than the constant region for the IgG$_1$ isotype.

In certain embodiments, conservative modifications to the heavy and light chains of anti-OPGL antibody (and corresponding modifications to the encoding nucleic acids) will produce anti-OPGL antibodies having functional and biochemical characteristics similar to those of anti-OPGL antibody. In contrast, substantial modifications in the functional and/or biochemical characteristics of anti-OPGL antibody may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain.

For example, a "conservative amino acid substitution" may involve a substitution of a native amino acid residue with a nonnative residue having little or no effect on the polarity or charge of the amino acid residue at that position. Furthermore, any native residue in the polypeptide may also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of anti-OPGL antibody, or to increase or decrease the affinity of the anti-OPGL antibodies described herein.

In alternative embodiments, antibodies of the present invention can be expressed in cell lines other than hybridoma cell lines. In these embodiments, sequences encoding particular antibodies can be used for transformation of a suitable mammalian host cell. According to these embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). Generally, the transformation procedure used may depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

A nucleic acid molecule encoding the amino acid sequence of a heavy chain constant region, a heavy chain variable region, a light chain constant region, or a light chain variable region of an OPGL antibody of the invention is inserted into an appropriate expression vector using standard ligation techniques. In a preferred embodiment, the anti-OPGL antibody heavy chain or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see METH. ENZ. 185 (Goeddel, ed.), 1990, Academic Press. Typically, expression vectors used in any of the host cells contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the OPGL polypeptide coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the OPGL antibody from the host cell. Affinity purification can be accomplished, for example, by column chromatography using antibodies against the tag as an affinity matrix. Optionally, the tag can subsequently be removed from the purified OPGL polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide-coding region and serves to terminate transcription. Usually, a transcription termination sequence in prokaryotic cells is a G—C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to OPGL polypeptide. As a result, increased quantities of a polypeptide such as an anti-OPGL antibody are synthesized from the amplified DNA. A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

The expression and cloning vectors of the present invention will typically contain a promoter that is recognized by the host organism and operably linked to nucleic acid encoding the anti-OPGL antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no experimental control over gene expression. A large number of promoters, recognized by a variety of potential host cells, are well known. A suitable promoter is operably linked to the DNA encoding anti-OPGL antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters that may be of interest include, but are not limited to: the SV40 early promoter region (Bernoist and Chambon, 1981, *Nature* 290: 304-10); the CMV promoter; the promoter contained in the 3' long terminal repeat of Rous sarcoma virus (Yamamoto, et al., 1980, *Cell* 22: 787-97); the herpes thymidine kinase promoter (Wagner et al., 1981, *Proc. Natl. Acad. Sci. U.S.A.* 78: 1444-45); the regulatory sequences of the metallothionine gene (Brinster et al., 1982, *Nature* 296: 39-42); prokaryotic expression vectors such as the beta-lactamase promoter (Villa-Kamaroff et al., 1978, *Proc. Natl. Acad. Sci. U.S.A.*, 75: 3727-31); or the tac promoter (DeBoer et al., 1983, *Proc. Natl. Acad. Sci. U.S.A.* 80: 21-25). Also of interest are the following animal transcriptional control regions, which exhibit tissue specificity and have been utilized in transgenic animals: the elastase I gene control region that is active in pancreatic acinar cells (Swift et al., 1984, *Cell* 38: 639-46; Ornitz et al., 1986, *Cold Spring Harbor Symp. Quant. Biol.* 50: 399-409; MacDonald, 1987, *Hepatology* 7: 425-515); the insulin gene control region that is active in pancreatic beta cells (Hanahan, 1985, *Nature* 315: 115-22); the mouse mammary tumor virus control region that is active in testicular, breast, lymphoid and mast cells (Leder et al., 1986, *Cell* 45: 485-95); the albumin gene control region that is active in liver (Pinkert et al., 1987, *Genes and Devel.* 1: 268-76); the alpha-feto-protein gene control region that is active in liver (Krumlauf et al., 1985, *Mol. Cell. Biol.* 5: 1639-48; Hammer et al., 1987, *Science* 235: 53-58); the alpha 1-antitrypsin gene control region that is active in the liver (Kelsey et al., 1987, *Genes and Devel.* 1: 161-71); the beta-globin gene control region that is active in myeloid cells (Mogram et al., 1985, *Nature* 315: 338-40; Kollias et al., 1986, *Cell* 46: 89-94); the myelin basic protein gene control region that is active in oligodendrocyte cells in the brain (Readhead et al., 1987, *Cell* 48: 703-12); the myosin light chain-2 gene control region that is active in skeletal muscle (Sani, 1985, *Nature* 314: 283-86); the gonadotropic releasing hormone gene control region that is active in the hypothalamus (Mason et al., 1986, *Science* 234: 1372-78); and most particularly the immunoglobulin gene control region that is active in lymphoid cells (Grosschedl et al., 1984, *Cell* 38: 647-58; Adames et al., 1985, *Nature* 318: 533-38; Alexander et al., 1987, *Mol. Cell Biol.* 7: 1436-44).

An enhancer sequence may be inserted into the vector to increase the transcription of a nucleic acid encoding an anti-OPGL antibody of the present invention by higher eukaryotes. Enhancers are cis-acting elements of DNA, usually about 10-300 by in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically located at a site 5' from the promoter.

Expression vectors of the invention may be constructed from a convenient starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding an anti-OPGL antibody has been inserted into the proper site of the vector, the completed vector may be inserted into a suitable host cell for amplification and/or polypeptide expression. The transformation of an expression vector for an anti-OPGL antibody into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

A host cell, when cultured under appropriate conditions, synthesizes an anti-OPGL antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and produce antibodies with constitutive OPGL binding properties. In another embodiment, a cell line from the B cell lineage that does not make its own antibody but has a capacity to make and secrete a heterologous antibody can be selected.

Antibodies of the invention are useful for detecting OPGL in biological samples and identification of cells or tissues that produce the protein. In certain embodiments, antibodies that bind to OPGL and block interaction with other binding compounds may have therapeutic use in modulating osteoclast differentiation and bone resorption. In certain embodiments, antibodies to OPGL may block OPGL binding to ODAR (RANK), which may result in a block in the signal transduction cascade and loss of NF-κB mediated transcription activation. Assays for measuring NF-κB-mediated transcription activation using, e.g., a luciferase reporter assay, are known to those skilled in the art.

In certain embodiments, antibodies to OPGL may be useful in treatment of bone diseases such as osteoporosis and Paget's disease. In certain embodiments, antibodies can be tested for binding to OPGL in the absence or presence of OPG and examined for their ability to inhibit OPGL-mediated osteoclastogenesis and/or bone resorption.

Anti-OPGL antibodies of the invention can be administered alone or in combination with other therapeutic agents, in particular, in combination with other cancer therapy agents. Such agents generally include radiation therapy or chemotherapy. Chemotherapy, for example, can involve treatment with one or more of the following: anthracyclines, taxol, tamoxifene, doxorubicin, 5-fluorouracil, and other drugs known to the skilled worker.

In addition, anti-OPGL antibodies can be administered to patients in combination with antibodies that bind to tumor cells and induce a cytotoxic and/or cytostatic effect on tumor growth. Examples of such antibodies include those that bind to cell surface proteins Her2, CDC20, CDC33, mucin-like glycoprotein and epidermal growth factor receptor (EGFR) present on tumor cells and induce a cytostatic and/or cytotoxic effect on tumor cells displaying these proteins. Examples of such antibodies include HERCEPTIN for treatment of breast cancer and RITUXAN for the treatment of non-Hodgkin's lymphoma. Also, combination therapy can include as cancer therapy agents polypeptides that selectively induce apoptosis in tumor cells, such as the TNF-related polypeptide TRAIL. Anti-OPGL or antigen binding fragments of the invention can be administered prior to, concurrent with, or subsequent to treatment with a cancer therapy agent. Anti-OPGL antibodies can be administered prophylactically to prevent or mitigate the onset of loss of bone mass by metastatic cancer or can be given for the treatment of an existing condition of loss of bone mass due to metastasis.

Anti-OPGL antibodies of the invention may be used to prevent and/or treat the growth of tumor cells in bone. Cancer that metastasizes to bone can spread readily as tumor cells stimulate osteoclasts to resorb the internal bone matrix. Treatment with an anti-OPGL antibody will maintain bone density by inhibiting resorption and decrease the likelihood of tumor cells spreading throughout the skeleton. Any cancer that metastasizes to bone may be prevented and/or treated with an anti-OPGL antibody.

In one embodiment, multiple myeloma may be prevented and/or treated with an anti-OPGL antibody or antigen binding fragment thereof. Multiple myeloma is localized to bone. Affected patients typically exhibit a loss of bone mass due to increased osteoclast activation in localized regions. Myeloma cells either directly or indirectly produce OPGL, which in turn activates osteoclasts resulting in local bone lysis surrounding the myeloma cells embedded in bone marrow spaces. The normal osteoclasts adjacent to the myeloma cell in turn produce IL-6, leading to growth and proliferation of myeloma cells. Myeloma cells expand in a clonal fashion and occupy bone spaces that are being created by inappropriate bone resorption. Treatment of an animal with an anti-OPGL antibody blocks activation of osteoclasts which in turn leads to a decrease in IL-6 production by osteoclasts, and a suppression of mycloma all growth and/or proliferation.

Anti-OPGL antibodies may be used alone for the treatment of the above referenced conditions resulting in loss of bone mass or in combination with a therapeutically effective amount of a bone growth promoting (anabolic) agent or a bone anti-resorptive agent including but not limited to bone morphogenic factors designated BMP-1 to BMP-12, transforming growth factor-$\beta$ and TGF-$\beta$ family members, fibroblast growth factors FGF-1 to FGF-10, interleukin-1 inhibitors, TNF$\alpha$ inhibitors, parathyroid hormone, E series prostaglandins, bisphosphonates and bone-enhancing minerals such as fluoride and calcium. Anabolic agents include parathyroid hormone and insulin-like growth factor (IGF), wherein the latter agent is preferably complexed with an IGF binding protein. Preferred embodiments also include the combination of an anti-OPGL antibody with an interluekin-1 (IL-1) receptor antagonist or an anti-OPGL antibody with a soluble TNF receptor, such as soluble TNF receptor-1 or soluble TNF receptor-2. An exemplary IL-1 receptor antagonist is described in WO89/11540 and an exemplary soluble TNF receptor-1 is described in WO98/01555.

In preferred embodiments, the invention provides pharmaceutical compositions comprising a therapeutically effective amount of the antibodies of the invention together with a pharmaceutically acceptable diluent, carrier, solubilizer, emulsifier, preservative and/or adjuvant. In certain embodiments, pharmaceutical compositions comprising a therapeutically effective amount of anti-OPGL antibodies are provided.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (REMINGTON'S PHARMACEUTICAL SCIENCES, 18$^{th}$ Edition, (A. R. Gennaro, ed.), 1990, Mack Publishing Company.

In certain embodiments, optimal pharmaceutical compositions will be determined by one skilled in the art depending upon, for example, the intended route of administration, delivery format and desired dosage. See, for example, REMINGTON'S PHARMACEUTICAL SCIENCES, ibid. Such compositions may influence the physical state, stability, rate of in vivo release and rate of in vivo clearance of the antibodies of the invention.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefor. Anti-OPGL antibody compositions may be prepared for storage by mixing the selected composition having the desired degree of purity with optional formulation agents (REMINGTON'S PHARMACEUTICAL SCIENCES, ibid.) in the form of a lyophilized cake or an aqueous solution. Further, the anti-OPGL antibody product may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical compositions of the invention can be delivered parenterally. When parenteral administration is contemplated, the therapeutic compositions for use in this invention may be in the form of a pyrogen-free, parenterally acceptable aqueous solution comprising the desired anti-OPGL antibody in a pharmaceutically acceptable vehicle. A particularly suitable vehicle for parenteral injection is sterile distilled water in which the anti-OPGL antibody is formulated as a sterile, isotonic solution, properly preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may be selected for inhalation. In these embodiments, an anti-OPGL antibody is formulated as a dry powder for inhalation, or anti-OPGL antibody inhalation solutions may also be formulated with a propellant for aerosol delivery, such as by nebulization. Pulmonary administration is further described in PCT Application No. PCT/US94/001875, which describes pulmonary delivery of chemically modified proteins.

The pharmaceutical compositions of the invention can be delivered through the digestive tract, such as orally. The preparation of such pharmaceutically acceptable compositions is within the skill of the art. Anti-OPGL antibodies that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption of the anti-OPGL antibody. Diluents, flavorings, low melting point waxes, vegetable oils, lubricants, suspending agents, tablet disintegrating agents, and binders may also be employed.

A pharmaceutical composition may involve an effective quantity of anti-OPGL antibodies in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving anti-OPGL antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, *Biopolymers* 22: 547-556), poly (2-hydroxyethyl-methacrylate) (Langer et al., 1981, *J. Biomed. Mater. Res.* 15: 167-277) and Langer, 1982, *Chem. Tech.* 12: 98-105), ethylene vinyl acetate (Langer et al., ibid.) or poly-D(−)-3-hydroxybutyric acid (EP 133,988). Sustained release compositions may also include liposomes, which can be prepared by any of several methods known in the art. See e.g., Eppstein et al., 1985, *Proc. Natl. Acad. Sci. USA* 82: 3688-3692; EP 036,676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation, including for example single and multi-chambered pre-filled syringes (e.g., liquid syringes, lyosyringes or needle-free syringes).

The effective amount of an anti-OPGL antibody pharmaceutical composition to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the anti-OPGL antibody is being used, the route of administration, and the size (body weight, body surface or organ size) and/or condition (the age and general health) of the patient. In certain embodiments, the clinician may titer the dosage and modify the route of administration to obtain the optimal therapeutic effect. Typical dosages range from about 0.1 µg/kg to up to about 30 mg/kg or more, depending on the factors mentioned above. In certain embodiments, the dosage may range from 0.1 µg/kg up to about 30 mg/kg; or 1 µg/kg up to about 30 mg/kg; or 5 µg/kg up to about 30 mg/kg.

Dosing frequency will depend upon the pharmacokinetic parameters of the anti-OPGL antibody in the formulation used. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Administration routes for the pharmaceutical compositions of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

It also may be desirable to use anti-OPGL antibody pharmaceutical compositions according to the invention ex vivo. In such instances, cells, tissues or organs that have been removed from the patient are exposed to anti-OPGL antibody pharmaceutical compositions after which the cells, tissues and/or organs are subsequently implanted back into the patient.

In particular, anti-OPGL antibody can be delivered by implanting certain cells that have been genetically engineered, using methods such as those described herein, to express and secrete the polypeptide. In certain embodiments, such cells may be animal or human cells, and may be autologous, heterologous, or xenogeneic, or may be immortalized. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the present invention.

Example 1

Production of Human Monoclonal Antibodies Against OPGL

Transgenic HuMab Mice

Fully human monoclonal antibodies to OPGL were prepared using HCo7, HCo12, and HCo7+HCo12 strains of transgenic mice, each of which expresses human antibody genes. In each of these mouse strains, the endogenous mouse kappa light chain gene has been homozygously disrupted (as described in Chen et al., 1993, *EMBO J.* 12: 811-820) and the endogenous mouse heavy chain gene has been homozygously disrupted as described in Example 1 of PCT Publication WO 01/09187 (incorporated by reference). Each of these mouse strains carries a human kappa light chain transgene, KCo5 (as described in Fishwild et al., 1996, *Nature Biotechnology* 14: 845-851). The HCo7 strain carries the HCo7 human heavy chain transgene as described in U.S. Pat. Nos. 5,545,806; 5,625,825; and 5,545,807 (incorporated by reference). The HCo12 strain carries the HCo12 human heavy chain transgene as described in Example 2 of PCT Publication WO 01/09187 (incorporated by reference). The HCo7+HCo12 strain carries both the HCo7 and the HCo12 heavy chain transgenes and is hemizygous for each transgene. All of these strains are referred to herein as HuMab mice.

HuMab Immunizations:

To generate fully human monoclonal antibodies to OPGL, HuMab mice were immunized with purified recombinant OPGL derived from *E. coli* or CHO cells as antigen. General immunization schemes for HuMab mice are described in Lonberg et al. 91994, *Nature* 368: 856-859, Fishwild et al., ibid., and PCT Publication WO 98/24884 (the teachings of each of which are incorporated by reference). Mice were 6-16 weeks of age upon the first infusion of antigen. A purified recombinant preparation (50-100 µg) of OPGL antigen (e.g., purified from transfected *E. coli* or CHO cells expressing OPGL) was used to immunize the HuMab mice intraperitoneally (IP) or subcutaneously (Sc).

Immunizations of HuMab transgenic mice were performed twice using antigen in complete Freund's adjuvant, followed by 2-4 weeks IP immunization (up to a total of 9 immunizations) with the antigen in incomplete Freund's adjuvant. Several dozen mice were immunized for each antigen. A total of 136 HuMab mice of the HCo7, HCo12, and HCo7+HCo12 strains were immunized with OPGL. The immune response was monitored by retroorbital bleeds.

To select HuMab mice producing antibodies that bound OPGL, sera from immunized mice was tested by ELISA as described by Fishwild et al. supra. Briefly, microtiter plates were coated with purified recombinant OPGL from CHO cells or *E. coli* at 1-2 µL/mL in PBS and 50 µL/well incubated at 4° C. overnight, then blocked with 200 µL/well with 5% chicken serum in PBS/Tween (0.05%). Dilutions of plasma from OPGL-immunized mice were added to each well and incubated for 1-2 hours at ambient temperature. The plates were washed with PBS/Tween and then incubated with a goat anti-human IgG Fc-specific polyclonal reagent conjugated to horseradish peroxidase (HRP) for 1 hour at room temperature. After washing, the plates were developed with ABTS substrate (Sigma, A-1888, 0.22 mg/mL) and analyzed at OD of 415-495. Mice with sufficient titers of anti-OPGL human immunoglobulin were used to produce monoclonal antibodies as described below.

Generation of Hybridomas Producing Human Monoclonal Antibodies to OPGL

Mice were prepared for monoclonal antibody production by boosting with antigen intravenously 2 days before sacrifice, and spleens were removed thereafter. The mouse splenocytes were isolated from the HuMab mice and fused with PEG to a mouse myeloma cell line based upon standard protocols. Typically, 10-20 fusions for each antigen were performed.

Briefly, single cell suspensions of splenic lymphocytes from immunized mice were fused to one-quarter the number of P3X63-Ag8.653 nonsecreting mouse myeloma cells (ATCC, CRL 1580) using 50% PEG (Sigma Chemical Co., St. Louis, Mo.). Cells were plated at approximately $1 \times 10^5$ cells/well in flat bottom microtitre plates, followed by about two week incubation in selective medium containing 10% fetal bovine serum, 10% P388D1 (ATCC, CRL TIB-63) conditioned medium and 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/mL gentamycin and 1×HAT (Sigma, CRL P-7185). After 1-2 weeks, cells were cultured in medium in which the HAT was replaced with HT.

The resulting hybridomas were screened for the production of antigen-specific antibodies. Individual wells were screened by ELISA (described above) for human anti-OPGL monoclonal IgG antibodies. Once extensive hybridoma growth occurred, medium was monitored usually after 10-14 days. Antibody secreting hybridomas were replated, screened again and, if still positive by ELISA for human IgG, anti-OPGL monoclonal antibodies were subcloned at least twice by limiting dilution. The stable subclones were then cultured in vitro to generate small amounts of antibody in tissue culture medium for characterization.

Selection of Human Monoclonal Antibodies that Bind to OPGL

An ELISA assay as described above was used to screen for hybridomas that showed positive reactivity with OPGL immunogen. Hybridomas secreting a monoclonal antibody that bound with high avidity to OPGL were subcloned and further characterized. One clone from each hybridoma, which retained the reactivity of parent cells (as determined by ELISA), was chosen for making a 5-10 vial cell bank stored in liquid nitrogen.

An isotype-specific ELISA was performed to determine the isotype of the monoclonal antibodies produced as disclosed herein. In these experiments, microtitre plate wells were coated with 50 µL/well of a solution of 1 µg/mL mouse anti-human kappa light chain in PBS and incubated at 4° C. overnight. After blocking with 5% chicken serum, the plates were reacted with supernatant from each tested monoclonal antibody and a purified isotype control. Plates were incubated at ambient temperature for 1-2 hours. The wells were then reacted with either human $IgG_1$ or $IgG_3$-specific horseradish peroxidase-conjugated goat anti-human polyclonal antisera and plates developed and analyzed as described above.

Monoclonal antibodies purified from six hybridoma supernatants that showed significant binding to OPGL as detected by ELISA were further tested for biological activity using in vitro receptor binding assays and human OPGL-dependent in vitro osteoclast forming assays (described in Example 6 below). The antibodies selected were designated 16E1, 2E11, 18B2, 2D8, 22B3, and 9H7. The heavy chain alignment for these anti-OPGL antibodies is shown in FIG. 15. The light chain alignment for the anti-OPGL antibodies is shown in FIG. 16. Non-consensus sequences are shown in bold and are shaded, and complementarity-determining regions (CDRs) are underlined.

Example 2

Cloning the 9H7 Anti-OPGL Heavy and Light Chains

Cloning of the 9H7 Anti-OPGL MAb Light Chain

Three anti-OPGL hybridoma light chain cDNAs (9H7, 16E1 and 18B2) were cloned into pDSR19 mammalian cell expression vector. The construction of a plasmid encoding the 9H7 kappa light chain is explicitly described; cloning of the other light chain species was performed using similar procedures. The anti-OPGL-9H7 kappa light chain variable region was obtained using polymerase chain reaction (PCR) amplification methods from first strand cDNA prepared from hybridoma 9H7 total RNA. First strand cDNA was prepared from 9H7 total RNA using a random primer with an extended 5'-adapter (5'-GGCCGGATAGGCCTCACNNNNNNT-3', SEQ ID NO: 53) and the materials and methods provided by the Gibco SuperScript II ™ Preamplification System for First Strand cDNA Synthesis kit (Catalogue No. 18089-011). The oligonucleotides below were used for the PCR:

```
5' GeneRacer ™ (Invitrogen) primer (SEQ ID NO: 54):
5' - GGA CAC TGA CAT GGA CTG AAG GAG TA - 3';

3' kappa RACE primer, 2310-03 (SEQ ID NO: 55):
5' - GGG GTC AGG CTG GAA CTG AGG- 3'.
```

The amplified DNAs were cloned into pCRII-TOPO (Invitrogen) and the resulting plasmids were sequenced. The kappa chain consensus sequence was used to design primers for PCR amplification of the variable region of the 9H7 kappa chain. To generate the signal sequence, a three-step PCR was performed. First, primers 2669-73 and 2708-53 (set forth below) were used with a 9H7 cDNA light chain clone template. Conditions used for the reaction were: 94° C. for 1 minute; 94° C. for 20 seconds, 42° C. for 30 seconds, 74° C. for 150 seconds for 2 cycles; 94° C. for 20 seconds, 56° C. for 30 seconds, 74° C. for 150 seconds for 25 cycles; and 74° C. for 7 minutes with Pfu polymerase and the appropriate buffer and nucleotides. The PCR product was then amplified with primers 2663-07 and 2708-53 followed by amplification with primers 2663-08 and 2708-53. These primers are shown below.

```
2663-08
                                          (SEQ ID NO: 56)
             HindIII XbaI Kozak
5'-C AGC AG AAGCTTCTAGA CCACC ATG GAC ATG AGG

GTG CCC GCT CAG CTC CTG GG-3';

2663-07
                                          (SEQ ID NO: 57)
5'-CC GCT CAG CTC CTG GGG CTC CTG CTG CTG TGG

CTG AGA GGT GCC AGA T-3';

2669-73
                                          (SEQ ID NO: 58)
5'-G TGG TTG AGA GGT GCC AGA TGT GAA ATT GTG

CTG ACC CAG TCT CCA GCC ACC CTG TCT TTG TCT C-3';

2708-53
                                          (SEQ ID NO: 59)
      SalI
5'-CTT GTC GAC TCA ACA CTC TCC CCT GTT GAA GCT

C-3'.
```

The PCR reactions generated a 741 by fragment encoding 238 amino acid residues (including the 22 amino acid signal sequence) that was purified using a QIAquick PCR Purification kit (Qiagen Cat. No. 28104), cut with XbaI and SalI, and Qiagen purified again. This fragment, containing the complete light chain with a 5' Kozak (translational initiation) site and the following signal sequence for mammalian expression:

(SEQ ID NO: 60)
MDMRVPAQLLGLLLLWLRGARC, was ligated into pDSRα19 to generate plasmid pDSRα19: 9H7 kappa (FIG. 17). pDSRα19 has been described previously (see International Application, Publication No. WO 90/14363, which is herein incorporated by reference for any purpose). Briefly, to make pDSRα19, pDSRα2 was modified in the following ways: the sequence containing the transcription termination/polyadenylation signal from the alpha subunit of the bovine pituitary glycoprotein hormome alpha-FSH (follicle-stimulating hormone) was shortened by approximately 1400 base pairs, to 885 base pairs, and ends at the NdeI site after modification; the dihydrofolate reductase (DHFR) promoter contained 209 base pairs, having been shortened from the 5' end by approximately 1 kilobase; and an approximately 550 base pair Bg/II fragment from the DHFR polyA sequence was deleted.

The 9H7 kappa light chain expression clone was sequenced to confirm that it encoded the same peptide that was identified in the 9H7 hybridoma. The final expression vector, pDSRα19:9H7 kappa is 5479 by and contains the 7 functional regions described in Table 2.

TABLE 2

| Plasmid Base Pair Number: | |
|---|---|
| 2 to 881 | A transcription termination/polyadenylation signal from the α-subunit of the bovine pituitary glycoprotein hormone (α-FSH) (Goodwin, et al., 1983, *Nucleic Acids Res.* 11:6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci. U.S.A.* 79:6522-6; Nunberg et al., 1980, Cell 19:355-64; Setzer et al., 1982, *J. Biol. Chem.* 257:5143-7; McGrogan et al., 1985, *J. Biol. Chem.* 260:2307-14) |
| 2031 to 3947 | pBR322 sequences containing the ampicillin resistance marker gene and the origin for replication of the plasmid in *E. coli* (Genbank Accession Number J01749) |

TABLE 2-continued

| Plasmid Base Pair Number: | |
|---|---|
| 3949 to 4292 | An SV40 early promoter, enhancer and origin of replication (Takebe et al., 1988, *Mol. Cell Biol.* 8:466-72, Genbank Accession Number J02400) |
| 4299 to 4565 | A translational enhancer element from the HTLV-1 LTR domain (Seiki et al., 1983, *Proc. Natl. Acad. Sci. U.S.A.* 80:3618-22, Genbank Accession Number J02029) |
| 4574 to 4730 | An intron from the SV40 16S, 19S splice donor/acceptor signals (Okayama and Berg, 1983. *Mol. Cell Biol.* 3:280-9, Genbank Accession Number J02400) |
| 4755 to 5479 | The 9H7D4 kappa light chain cDNA between the Xba1 and Sal1 sites |

Construction of pDSR19:hIgG1 $C_H$

A pDSR19: rat variable region/human constant region IgG$_1$ plasmid was constructed using a three-piece ligation of a rat variable region sequence, the human constant region (CH1, hinge, CH2, and CH3 domains) and pDSR19. The linear pDSRα19:hIgG1 $C_H$ plasmid was prepared by digesting the pDSR19:rat variable region/human constant region IgG$_1$ plasmid with restriction enzymes XbaI and BsmBI to remove the coding portion of the rat variable region. The resulting linear plasmid containing the 1.0 kbp human IgG$_1$ constant region domain ($C_H$1, hinge, $C_H$2 and $C_H$3 domains) was gel isolated and used to accept hybridoma derived αOPGL variable regions.

Cloning of the 9H7 Anti-OPGL MAb Heavy Chain

Three anti-OPGL hybridoma IgG$_1$ heavy chain cDNAs; 9H7, 16E1 and 18B2, were cloned into pDSR19 mammalian cell expression vector. The construction of a plasmid encoding the 9H7 IgG$_1$ heavy chain is explicitly described here; the other hybridoma heavy chains were cloned using similar procedures. The anti-OPGL-9H7 heavy chain variable region was obtained using PCR amplification methods from first strand cDNA prepared from hybridoma 9H7 total RNA. First strand cDNA was prepared from 9H7 total RNA using a random primer with an extended 5'-adapter (5'-GGCCGGAT-AGGCCTCACNNNNNNT-3', SEQ ID NO: 53) and the materials and methods provided by the Gibco SuperScript II ™ Preamplification System for First Strand cDNA Synthesis kit (Cat. No. 18089-011). The oligonucleotides below were used for the PCR:

```
5' heavy chain RACE primer, 2508-02
(SEQ ID NO: 61):
5' - (CG)AG GT(CG) CAG (CT)T(GT) GTG (CG)AG TC- 3;

3' heavy chain RACE primer, 2420-54
(SEQ ID NO: 62):
5' -CTG AGT TCC ACG ACA CC - 3'.
```

Amplified DNA was cloned into pCRII-TOPO (Invitrogen) and the resulting plasmids were sequenced. The heavy chain consensus sequence was used to design primers for PCR amplification of the variable region of the 9H7 heavy chain. To generate the signal sequence, a three-step PCR was performed. First, primers 2512-98 and 2673-14 were used with a 9H7 heavy chain cDNA clone template. Conditions used for the reaction were: 94° C. for 1 minute; 94° C. for 20 seconds, 42° C. for 30 seconds, 74° C. for 150 seconds for 2 cycles; 94° C. for 20 seconds, 56° C. for 30 seconds, 74° C. for 150 seconds for 25 cycles; and 74° C. for 7 minutes with Pfu polymerase and the appropriate buffer and nucleotides. The PCR product was then amplified with primers 2663-07 and 2673-14 followed by amplification with primers 2663-08 and 2673-14. The primers are shown below.

```
2663-08
                                      (SEQ ID NO: 63)
             HindIII XbaI Kozak
5'-C AGC AG AAGCTTCTAGA CCACC ATG GAC ATG AGG

GTG CCC GCT CAG CTC CTG GG-3';

2663-07
                                      (SEQ ID NO: 64)
5'-CC GCT CAG CTC CTG GGG CTC CTG CTG CTG TGG

CTG AGA GGT GCC AGA T-3';

2512-98
                                      (SEQ ID NO: 65)
5'-G TGG TTG AGA GGT GCC AGA TGT GAG GTG CAG

CTG GTG CAG TCT -3';

2673-14
                                      (SEQ ID NO: 66)
                BsmBI
5'-GT GGA GGC ACT AGA GAC GGT GAC CAG GGC TCC

CTG GCC CCA GGG GTC GAA -3'.
```

The PCR reactions generated a 443 by fragment encoding 138 amino acid residues (including the 22 amino acid signal sequence) that was purified using a QIAquick PCR Purification kit (Qiagen Cat. No. 28104), cut with XbaI and BsmBI, and Qiagen purified again. This fragment, containing the heavy chain with a 5' Kozak (translational initiation) site and the following signal sequence for mammalian expression:

(SEQ ID NO: 60)
MDMRVPAQLLGLLLLWLRGARC, was ligated into pDSRα19:hIgG1$C_H$ to generate plasmid pDSRα19:9H7 IgG1 (FIG. 18).

The 9H7 IgG$_1$ heavy chain expression clone was sequenced to confirm that it encoded the same peptide that was identified in the 9H7 hybridoma. The final expression vector, pDSRα19:rat variable region/human constant region IgG$_1$ is 6158 by and contains the 7 functional regions described in Table 3.

TABLE 3

| Plasmid Base Pair Number: | |
|---|---|
| 2 to 881 | A transcription termination/polyadenylation signal from the α-subunit of the bovine pituitary glycoprotein hormone (α-FSH) (Goodwin, et al., 1983, *Nucleic Acids Res.* 11: 6873-82; Genbank Accession Number X00004) |

TABLE 3-continued

Plasmid Base

| Pair Number: | |
|---|---|
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, *Proc. Natl. Acad. Sci. U. S. A.* 79:6522-6; Nunberg et al., 1980, *Cell* 19: 355-64; Setzer et al., 1982, *J Biol. Chem.* 257:5143-7; McGrogan et al., 1985, *J. Biol. Chem.* 260: 2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, *Mol. Cell Biol.* 8:466-72, Genbank Accession Number J02400) |
| 4299 to 4565 | A translational enhancer element from the HTLV-1 LTR domain (Seiki et al., 1983, *Proc. Natl. Acad. Sci. U. S. A.* 80: 3618-22, Genbank Accession Number J02029) |
| 4574 to 4730 | An intron from the SV40 16S, 19S splice donor/acceptor signals (Okayama and Berg, 1983. *Mol. Cell Biol.* 3:280-9, Genbank Accession Number J02400) |
| 4755 to 6158 | The rVh/hCh1 heavy chain cDNA between the XbaI and SalI sites. The sequences of which follows (SEQ ID NO: 67):<br>XbaI<br>TCTAG ACCACCATGG ACATCAGGCT CAGCTTAGTT TTCCTTGTCC<br>TTTTCATAAA AGGTGTCCAG TGTGAGGTAG AACTGGTGGA<br>GTCTGGGGGC GGCTTAGTAC AACCTGGAAG GTCCATGACA<br>CTCTCCTGTG CAGCCTCGGG ATTCACTTTC AGAACCTATG<br>GCATGGCCTG GGTCCGCCAG GCCCCAACGA AGGGTCTGGA<br>GTGGGTCTCA TCAATTACTG CTAGTGGTGG TACCACCTAC<br>TATCGAGACT CCGTGAAGGG CCGCTTCACT ATTTTTAGGG<br>ATAATGCAAA AAGTACCCTA TACCTGCAGA TGGACAGTCC<br>GAGGTCTGAG GACACGGCCA CTTATTTCTG TACATCAATT<br>                                                      BsmBI<br>TCGGAATACT GGGGCCACGG AGTCATGGTC ACCGTCTCTA<br>GTGCCTCCACCAAGGGCCCA TCGGTCTTCC CCCTGGCACC<br>CTCCTCCAAG AGCACCTCTG GGGGCACAGC GGCCCTGGGC<br>TGCCTGGTCA AGGACTACTT CCCCGAACCG GTGACGGTGT<br>CGTGGAACTC AGGCGCCCTG ACCAGCGGCG TGCACACCTT<br>CCCGGCTGTC CTACAGTCCT CAGGACTCTA CTCCCTCAGC<br>AGCGTGGTGACCGTGCCCTC CAGCAGCTTG GGCACCCAGA<br>CCTACATCTG CAACGTGAATCACAAGCCCA GCAACACCAA<br>GGTGGACAAG AAAGTTGAGC CCAAATCTTG TGACAAAACT<br>CACACATGCC CACCGTGCCC AGCACCTGAA CTCCTGGGGG<br>GACCGTCAGT CTTCCTCTTC CCCCCAAAAC CCAAGGACAC<br>CCTCATGATC TCCCGGACCC CTGAGGTCAC ATGCGTGGTG<br>GTGGACGTGA GCCACGAAGACCCTGAGGTC AAGTTCAACT<br>GGTACGTGGA CGGCGTGGAG GTGCATAATG CCAAGACAAA<br>GCCGCGGGAG GAGCAGTACA ACAGCACGTA CCGTGTGGTC<br>AGCGTCCTCA CCGTCCTGCA CCAGGACTGG CTGAATGGCA<br>AGGAGTACAAGTGCAAGGTC TCCAACAAAG CCCTCCCAGC<br>CCCCATCGAG AAAACCATCTCCAAAGCCAA AGGGCAGCCC<br>CGAGAACCAC AGGTGTACAC CCTGCCCCCA TCCCGGGATG<br>AGCTGACCAA GAACCAGGTC AGCCTGACCT GCCTGGTCAA<br>AGGCTTCTAT CCCAGCGACA TCGCCGTGGA GTGGGAGAGC<br>AATGGGCAGCCGGAGAACAA CTACAAGACC ACGCCTCCCG<br>TGCTGGACTC CGACGGCTCC TTCTTCCTCT ATAGCAAGCT<br>CACCGTGGAC AAGAGCAGGT GGCAGCAGGG GAACGTCTTC<br>TCATGCTCCG TGATGCATGA GGCTCTGCAC AACCACTACA<br>CGCAGAAGAG CCTCTCCCTG TCTCCGGGTA<br>            SalI<br>AATGATAAGT CGAC |

Example 3

9H7 Anti-OPGL MAb Expression in CHO Cells

Recombinant anti-OPGL antibodies are produced by Chinese hamster ovary cells, specifically CHO AM-1/D, as disclosed in U.S. Pat. No. 6,210,924 (incorporated by reference). DNA sequences encoding the complete heavy or light chains of each anti-OPGL antibody of the invention are cloned into expression vectors such as those described above. CHO AM-1/D cells are co-transfected with an expression vector capable of expressing a complete heavy chain and an expression vector expressing the complete light chain of the appropriate anti-OPGL antibody. For example, to generate the 22B3 antibody, cells are co-transfected with a vector capable of expressing a complete heavy chain comprising the amino acid sequence as set forth in SEQ ID NO: 30 and a vector capable of expressing a complete light chain comprising the amino acid sequence set forth in SEQ ID NO: 32. To generate the 2E11 antibody, cells are co-transfected with a vector capable of expressing a complete heavy chain comprising the amino acid sequence as set forth in SEQ ID NO: 34 and a vector capable of expressing a complete light chain comprising the amino acid sequence set forth in SEQ ID NO: 36. To generate the 2D8 antibody, cells are co-transfected with a vector capable of expressing a complete heavy chain comprising the amino acid sequence as set forth in SEQ ID NO: 38 and a vector capable of expressing a complete light chain comprising the amino acid sequence set forth in SEQ ID NO: 40. To generate the 18B2 antibody, cells are co-transfected with a vector capable of expressing a complete heavy chain comprising the amino acid sequence as set forth in SEQ ID NO: 42 and a vector capable of expressing a complete light chain comprising the amino acid sequence set forth in SEQ ID NO: 44. To generate the 16E1 antibody, cells are co-transfected with a vector capable of expressing a complete heavy chain comprising the amino acid sequence as set forth in SEQ ID NO: 46 and a vector capable of expressing a complete light chain comprising the amino acid sequence set forth in SEQ ID NO: 48. To generate the 9H7 antibody, cells are co-transfected with a vector capable of expressing a complete heavy chain comprising the amino acid sequence as set forth in SEQ ID NO: 50 and a vector capable of expressing a complete light chain comprising the amino acid sequence set forth in SEQ ID NO: 52. Table 4 summarizes the complete heavy and complete light chains for the various OPGL antibodies.

TABLE 4

| Antibody | Heavy Chain Variable Region + Heavy Chain Constant Region | Complete Heavy Chain |
|---|---|---|
| 22B3 | SEQ ID NO: 6 + SEQ ID NO: 2 | SEQ ID NO: 30 |
| 2E11 | SEQ ID NO: 10 + SEQ ID NO: 2 | SEQ ID NO: 34 |
| 2D8 | SEQ ID NO: 14 + SEQ ID NO: 2 | SEQ ID NO: 38 |
| 18B2 | SEQ ID NO: 18 + SEQ ID NO: 2 | SEQ ID NO: 42 |
| 16E1 | SEQ ID NO: 22 + SEQ ID NO: 2 | SEQ ID NO: 46 |
| 9H7 | SEQ ID NO: 26 + SEQ ID NO: 2 | SEQ ID NO: 50 |

| Antibody | Light Chain Variable Region + Light Chain Constant Region | Complete Light Chain |
|---|---|---|
| 22B3 | SEQ ID NO: 8 + SEQ ID NO: 4 | SEQ ID NO: 32 |
| 2E11 | SEQ ID NO: 12 + SEQ ID NO: 4 | SEQ ID NO: 36 |
| 2D8 | SEQ ID NO: 16 + SEQ ID NO: 4 | SEQ ID NO: 40 |
| 18B2 | SEQ ID NO: 20 + SEQ ID NO: 4 | SEQ ID NO: 44 |
| 16E1 | SEQ ID NO: 24 + SEQ ID NO: 4 | SEQ ID NO: 48 |
| 9H7 | SEQ ID NO: 28 + SEQ ID NO: 4 | SEQ ID NO: 52 |

Stable expression of the 9H7 anti-OPGL MAb was achieved by co-transfection of pDSRα19:9H7 IgG$_1$ and pDSRα19:9H7 kappa plasmids into dihydrofolate reductase deficient (DHFR$^-$) serum-free adapted Chinese hamster ovary cells (CHO AM-1/D, U.S. Pat. No. 6,210,924) using the art-recognized calcium phosphate method. Transfected cells were selected in 96 well plates in medium containing dialyzed serum but not containing hypoxanthine-thymidine to ensure the growth of cells expressing the DHFR enzyme. Over 5000 transfected clones were screened using assays such as HTRF (homogeneous time resolved fluorescence) and ELISA in order to detect expression of 9H7 anti-OPGL MAb in the conditioned medium. The highest expressing clones were selected for single cell cloning and creation of cell banks.

Example 4

Production of Anti-OPGL Antibodies

Anti-OPGL antibodies are produced by expression in a clonal line of CHO cells. For each production run, cells from a single vial are thawed into serum-free cell culture media. The cells are grown initially in a T-flask and are serially expanded through a series of spinner flasks until sufficient inoculum has been generated to seed a 20L bioreactor. Following growth for 5-10 days, the culture is then used to inoculate a 300L bioreactor. Following growth for an additional 5-10 days, the culture is used to inoculate a 2000L bioreactor. Production is carried out in a 2000L bioreactor using a fed batch culture, in which a nutrient feed containing concentrated media components is added to maintain cell growth and culture viability. Production lasts for approximately two weeks during which time anti-OPGL antibody is constitutively produced by the cells and secreted into the cell culture medium.

The production reactor is controlled at set pH, temperature, and dissolved oxygen level: pH is controlled by carbon dioxide gas and sodium carbonate addition; dissolved oxygen is controlled by air, nitrogen, and oxygen gas flows.

At the end of production, the cell broth is fed into a disk stack centrifuge and the culture supernatant is separated from the cells. The concentrate is further clarified through a depth filter followed by a 0.2 μm filter. The clarified conditioned media is then concentrated by tangential flow ultrafiltration. The conditioned media is concentrated 15- to 30-fold. The resulting concentrated conditioned medium is then either processed through purification or frozen for purification at a later date. FIG. 19 depicts an exemplary cell culture process for producing an anti-OPGL antibody.

Example 5

Screening of Antibodies for binding to OPGL by BIAcore

All experiments were performed on a BIAcore 2000 according to the manufacturer's instructions, with the following modifications. Experiments were performed at room temperature using a running buffer containing 10 mM Hepes (pH 7.4), 0.15M NaCl, 3 mM EDTA, and 0.005% Tween 20. Protein G at 50 μg/mL in 10 mM acetate pH 4.5 was immobilized to a level of 1,600 response units (RU) onto a CM5 Research grade sensor chip (BIAcore, Inc.). Antibodies (8-20 μg/mL) were captured onto the Protein G chip at a level of 300-400 RUs. CHO human OPGL (hOPGL) 140 or *E. coli* mouse OPGL (mOPGL) 158 were passed over the immobilized antibodies at concentrations of 0.25-62 nM. Langmuir 1:1 model was used to determine binding kinetics. Protein G immobilized to 1600 RUs was used as a blank surface. A mouse monoclonal antibody was used as a positive control to show binding to hOPGL 140 and to monitor surface stability.

All anti-OPGL antibodies showed strong binding to CHO hOPGL 140. 22B3 appears to have a slower off rate than the other antibodies tested. No binding of *E. coli* mOPGL 158 was detected. The results are summarized in Table 5.

TABLE 5

| | hOPGL 140 | | | | | |
|---|---|---|---|---|---|---|
| Ab | ka (1/Ms) | kd (1/s) | KD (1/M) | KD | off rate half life t½ (s) | mOPGL 158 |
| 9H7 | 1.27E+06 | 2.26E−04 | 1.93E−10 | 190 pm | 3067 | no binding |
| 18B2 | 8.78E+05 | 1.86E−04 | 2.11E−10 | 210 pm | 3726 | no binding |
| 2D8 | 1.97E+06 | 1.81E−04 | 9.20E−11 | 92 pm | 3829 | no binding |
| 2E11 | 4.53E+05 | 1.32E−04 | 2.92E−10 | 290 pm | 5251 | no binding |
| 16E1 | 2.16E+06 | 1.37E−04 | 6.33E−11 | 63 pm | 5059 | no binding |
| 22B3 | 1.90E+06 | 6.39E−05 | 3.37E−11 | 34 pm | 10847 | no binding |

Example 6

Anti-OPGL Antibody Neutralizing Activity

Inhibition of Osteoclast Formation

RAW 264.7 (Accession No. TIB-71, American Type Culture Collection, Manassas, Va.) is a murine macrophage cell line that was derived from an Abelson murine leukemia virus-induced tumor. RAW 264.7 cells will differentiate to osteoclast-like cells in the presence of OPGL. An assay for generation of osteoclasts in culture from RAW cells in the presence of OPGL has been described in detail by Hsu et al., 1999, *Proc. Natl. Acad. Sci. U.S.A.* 96:3540-3545, which is incorporated by reference herein.

RAW cells can be stimulated by OPGL ligand to differentiate into osteoclast-like cells, and the differentiation can be measured by tartrate-resistant acid phosphatase (TRAP) activity, a property of osteoclasts. This activity provides the basis for characterizing anti-OPGL antibodies produced according to the invention, by assaying the effect of said antibodies on osteoclastogenesis.

RAW cells were incubated for 4 days in the presence of a constant amount of OPGL (40 ng/mL) and varying amounts of anti-OPGL antibody (6.3 ng/mL to 200 ng/mL) in cell culture medium (DMEM, 10% FBS, 0.3 mg/mL L-glutamine, 100 units/mL penicillin G, 100 μg/mL streptomycin sulfate). At the end of 4 days, the cells were stained for tartrate-resistant acid phosphatase (TRAP) activity by permeabilization and acidification, followed by treatment with p-nitrophenylphosphate (PNPP) for 5 minutes. Briefly, the media was aspirated from the cells, and 100 μL of citrate buffer (having a formula of 410 mL 0.1M citric acid, 590 mL 0.1 M citrate, trisodium salt and 1 mL Triton X-100) was added to each well and the plates incubated for 3 to 5 minutes at room temperature. One hundred microliters of PNPP solution (having a formula of 157.8 mg acid phosphatase reagent (Sigma 104-100), 7.2 mL tartrate solution (Sigma Cat. No. 387-3), and 22.8 mL citrate buffer) was then added, and plates were incubated for 3 to 5 minutes at room temperature. The reaction was terminated by addition of 50 μL 0.5 M NaOH solution.

TRAP converts p-nitrophenylphosphate to para-nitrophenol, which can be quantitated by optical density measurement at 405 nm. The TRAP activity, which is a surrogate marker for osteoclast development, therefore correlates with the optical density at 405 nm. A plot of optical density versus anti-OPGL antibody concentration is shown in FIG. 20, and demonstrates that anti-OPGL antibody inhibited osteoclast formation in this assay in a dose-dependent manner. $IC_{50}$ values were calculated using the forecast function, and are shown in Table 6. An alkaline phosphatase-linked rat polyclonal anti-human OPGL antibody (AP Ra-anti-HuOPGL Ab) with OPGL neutralizing activity was used as a positive control for the anti-huOPGL antibody neutralizing activity assay.

TABLE 6

| Sample | $IC_{50}$ (ng/mL) |
|---|---|
| AP Ra-anti-HuOPGL Ab | 112 |
| 9H7 | 129 |
| 18B2 | 80 |
| 2D8 | 611 |
| 2E11 | 77 |
| 16E1 | 352 |
| 22B3 | 146 |

TABLE 6-continued

| | $IC_{50}$ (ng/mL) Running Average AP Ra-anti-HuOPGL Ab |
|---|---|
| Average | 140 |
| Stdev | 35.8 |
| CV | 26% |
| Count | 25 |

Example 7

Pharmacokinetics in Cynomolgus Monkeys

The in vivo activity and pharmacokinetics of the anti-OPGL antibodies of the invention were assayed using cynomolgus monkeys. Three female cynomolgus monkeys, not greater than 5 years of age and weighing 2 to 5 kg each received single subcutaneous (SC) doses of 1 mg/kg anti-OPGL antibody.

Animals were dosed with anti-OPGL antibody expressed from transfected Chinese hamster ovary (CHO) cells and serum samples were taken for determination of anti-OPGL antibody levels, anti-therapeutic antibody analysis, and analysis of the bone turnover marker serum N-telopeptide (serum N-Tx), alkaline phosphatase (ALP), and serum calcium (serum Ca).

The serum concentration-time profiles following SC administration are shown in FIG. 21. The serum N-Tx concentration-time profiles following SC administration are shown in FIG. 22.

Example 8

Identification of an Epitope for Antibodies on OPGL

Production of Variant Murine OPGL

Human OPGL [143-317] was produced as described in Example 1 of WO 01/62932, published August 30, 2001, which is hereby incorporated by reference in its entirety. Murine OPGL [158-316] containing amino acid residues 158 through 316 of murine OPGL (as shown in FIG. 1 of International Application, Publication No. WO98/46751, incorporated by reference) preceded by an introduced N-terminal methionine residue was produced in *E. coli*. Murine OPGL [158-316] was purified from the soluble fraction of bacteria as described previously (Lacey et al., 1998, *Cell* 93:165-176). FLAG-tagged murine OPGL [158-316] was produced by introducing a nucleic acid encoding an N-terminal methionine followed by a FLAG-tag sequence fused to the N-terminus of residues 158-316 as shown in FIG. 1 of International Application, Publication No. WO98/46751 using conventional genetic engineering techniques. The FLAG-tagged OPGL [158-316] molecule was cloned into bacterial expression vector pAMG21 (pAMG21 was deposited with the American Type Culture Collection and having Accession No. 98113).

A FLAG-tagged murine OPGL [158-316] polypeptide variant was constructed in which amino acid residues SVPTD (SEQ ID NO: 68) at positions 229-233 (as shown in FIG. 1 of International Application, Publication No. WO98/46751) were substituted with corresponding amino acid residues DLATE (SEQ ID NO: 69) at positions 230-234 (as shown in FIG. 4 of International Application, Publication No. WO98/46751). The resulting construct referred to as "FLAG-murine OPGL [158-316]/DE" has the nucleic acid and protein sequence as shown in FIG. 23 (SEQ ID NO: 72) (which shows only where the mutations are located). The amino acid sequence changes are located in a region of OPGL between the D and E regions. FIG. 23 shows a comparison of murine (SEQ ID NO: 70), human (SEQ ID NO: 71), and murine DE variant (SEQ ID NO: 72) amino acid sequences in this region. The sequence changes in the murine variant are S231D, V232L, P233A and D235E with the T at position 234 unchanged. Flanking sequences in this region are virtually identical between murine and human OPGL.

This molecule was constructed using a two-step PCR reaction where the first step contained two separate PCR reactions, designated reaction A and reaction B. For both reaction A and reaction B, pAMG21-FLAG-murine OPGL [158-316] DNA was used as a template for PCR. Reaction A employed oligonucleotides #2640-90 and #2640-91 for PCR, whereas reaction B employed oligonucleotides #2640-92 and #2640-93.

```
#2640-90 (SEQ ID NO: 73):
CCTCTCATATGGACTACAAGGAC;

#2640-91 (SEQ ID NO 74):
AGTAGCCAGGTCTCCCGATGTTTCATGATG;

#2640-92 (SEQ ID NO: 75):
CTGGCTACTGAATATCTTCAGCTGATGGTG;

#2640-93 (SEQ ID NO: 76):
CCTCTCCTCGAGTTAGTCTATGTCC.
```

Conditions for reactions A and B were: 95° C. for 1 min; 95° C. for 20 seconds, 44° C. for 30 seconds, 72° C. for 45 seconds for 5 cycles; 95° C. for 20 seconds, 60° C. for 30 seconds, 72° C. for 45 seconds for 25 cycles; and 72° C. for 10 minutes with Pfu Turbo polymerase (Stratagene) and the appropriate buffer and nucleotides. After thermocycling was performed, PCR products from reactions A and B were purified from an agarose gel using conventional methods. The second step PCR reaction, designated reaction C, utilized purified reaction A and reaction B PCR products as a template and oligonucleotides #2640-90 and #2640-93 as primers. Conditions for reaction C were: 95° C. for 1 minute; 95° C. for 20 seconds, 37° C. for 30 seconds, 72° C. for 1 minute for 25 cycles; and 72° C. for 10 minutes with Pfu Turbo polymerase and the appropriate buffer and nucleotides. Following thermocycling, the product from reaction C was cloned into the pCRII-TOPO cloning vector (Invitrogen) and electroporated into DH10b (Gibco) cells using methods provided by the manufacturer. Clones were selected and sequenced to confirm the amino acid sequence SVPTD (SEQ ID NO: 68) in murine OPGL [158-316] was changed to DLATE (SEQ ID NO: 69). The sequence-verified DNA was then digested with NdeI and XhoI, purified, and subcloned into bacterial expression vector pAMG21 giving rise to plasmid pAMG21-FLAG-murine OPGL[158-316]/DE.

E. coli host GM94 (deposited with the American Type Culture Collection under Accession No. 202173) containing plasmid pAMG21-FLAG-murine OPGL[158-316]/DE was grown in 2XYT media to an exponential growth phase and induced to express the FLAG-tagged murine OPGL[158-316]/DE protein by addition of V. fischeri synthetic autoinducer to 100 ng/mL. Approximately 3-6 hours after induction, the cells were pelleted and recombinant FLAG-murine OPGL[158-316]/DE protein was purified from the soluble fraction of E. coli using methods described in Lacey et al., ibid.

Binding of Anti-Human OPGL Antibodies to Human OPGL [143-317], Murine OPGL[158-316], and FLAG-Murine OPGL[158-316]/DE Costar E.I.A./R.I.A. Plates (Flat Bottom High Binding, Cat# 3590) were coated with 100 μL/well of either human OPGL[143-317] protein, murine OPGL[158-316] protein, or FLAG-tagged murine OPGL[158-316]/DE protein at 3 μg/mL in PBS, overnight at 4° C. with agitation. After overnight incubation, the protein solutions were removed from the plate and 200 μL of 5% Chicken Serum (Gibco/BRL Cat# 16110-082) in PBST (PBS plus 0.05% Tween 20) was added to each well of the plate and plates were incubated at room temperature (RT) for 3 hours with agitation. After incubation and blocking, plates were washed 4 times with 1×K-P wash solution in dH$_2$O (Cat# 50-63-00, Kirkegaard & Perry Laboratories) and dried. Purified anti-OPGL antibody or human OPGL [22-194]-Fc protein was serially diluted 1:1 from 2 μg/mL to 1.953 ng/mL in 5% Chicken Serum in PBST and 100 μL/well was added to appropriate wells of the microtiter plate coated with either human OPGL[143-317], murine OPGL[158-316], or FLAG-tagged murine OPGL[158-316]/DE protein. Plates were incubated for 2.25 hours at room temperature with agitation, washed four times with 1×K-P wash solution and dried. Goat anti-human IgG (Fc) (Jackson ImmunoResearch, Cat# 109-036-098) was diluted 1:3000 in 5% Chicken Serum in PBST and 100 μL was added to each well. Plates were incubated for 1.25 hours at room temperature with agitation, washed six times with 1×K-P wash solution, and dried. 100 μL of undiluted ABTS substrate (Kirkegaard & Perry; Cat# 50-66-00) was added to each well and the dish was incubated at room temperature until sufficient blue-green color developed. Color development was stopped by addition of 100 μL 1% SDS. Quantitation of color development was performed using a microtiter plate reader with detection at 405 nm.

The results of the enzyme immunoassay are shown in FIGS. 24 and 25. All six anti-OPGL antibodies of the invention bind to human OPGL[143-317]. However, only 22B3 antibody shows detectable binding to murine OPGL[158-316] over the concentration range tested (FIG. 24). While binding of 22B3 antibody to murine OPGL[158-316] occurs with a much lower affinity than to human OPGL[143-317], the 2D8, 9H7, 16E1, and 22B3 antibodies bind to FLAG-tagged murine OPGL[158-316]/DE (FIG. 25) almost as well as to human OPGL[143-317] under the assay conditions above. Thus, the amino acid changes in murine OPGL[158-316]/DE compared to murine OPGL[158-316] are important to the binding activity of antibodies 2D8, 9H7, 16E1, and 22B3. Antibodies 2E11 and 18B2 show no detectable binding to either murine OPGL[158-316] or murine OPGL[158-316]/DE.

The FLAG-murine OPGL[158-316]/DE was assayed for activity in a RAW cell assay as described in Example 6 and observed to have a similar ED50 for osteoclast formation as human OPGL[143-317], indicating that the DE variant is active in promoting osteoclast activity in vitro. Therefore, the binding of the anti-OPGL antibodies to murine OPGL[158-316]/DE is likely to inhibit osteoclast formation.

The epitope of the 2D8, 9H7, 16E1, and 22B3 anti-human OPGL antibodies is located to a region of human OPGL that includes at least amino acid residues DLATE (SEQ ID NO: 103) (residues 230 through 234 of human OPGL as shown in FIG. 4 of International Application, Publication No. WO98/46751) termed the D-E loop. The 2E11 and 18B2 anti-human OPGL antibodies do not bind to peptide fragments corre sponding to the D-E loop region by itself. However, it will be recognized that in the native molecule these antibodies may bind to an epitope outside the D-E loop region or they may bind to all or a portion of the D-E loop region on combination with other portions of the molecule.

It should be understood that the foregoing disclosure emphasizes certain specific embodiments of the invention and that all modifications or alternatives equivalent thereto are within the spirit and scope of the invention as set forth in the appended claims.

We claim:

1. An isolated nucleic acid molecule or a combination of isolated nucleic acid molecules that encodes an antibody or an antigen-binding fragment thereof that specifically binds human osteoprotegerin ligand (OPGL), wherein the antibody or an antigen-binding fragment thereof comprise a heavy chain variable region and a light chain variable region, wherein the heavy chain variable region comprises any of SEQ ID NO: 6, SEQ ID NO: 10, SEQ ID NO: 14, SEQ ID NO: 18, SEQ ID NO: 22, or SEQ ID NO: 26.

2. An isolated nucleic acid molecule or a combination of isolated nucleic acid molecules that encodes an antibody or an antigen-binding fragment thereof that specifically binds human osteoprotegerin ligand (OPGL), wherein the antibody or an antigen-binding fragment thereof comprises a heavy chain variable region and a light chain variable region, wherein the light chain variable region comprises any of SEQ ID NO: 8, SEQ ID NO: 12, SEQ ID NO: 16, SEQ ID NO: 20, SEQ ID NO: 24, or SEQ ID NO: 28.

3. An isolated nucleic acid molecule or a combination of isolated nucleic acid molecules that encodes an antibody or an antigen-binding fragment thereof that specifically binds human osteoprotegerin ligand (OPGL), wherein the antibody or an antigen-binding fragment thereof comprises a heavy chain and a light chain, wherein the heavy chain comprises SEQ ID NO: 30, SEQ ID NO: 34, SEQ ID NO: 38, SEQ ID NO: 42, SEQ ID NO: 46, or SEQ ID NO: 50.

4. An isolated nucleic acid molecule or a combination of isolated nucleic acid molecules that encodes an antibody or an antigen-binding fragment thereof that specifically binds human osteoprotegerin ligand (OPGL), wherein the antibody or an antigen-binding fragment thereof comprises a heavy chain and a light chain, wherein the light chain comprises SEQ ID NO: 32, SEQ ID NO: 36, SEQ ID NO: 40, SEQ ID NO: 44, SEQ ID NO: 48, or SEQ ID NO: 52.

5. The isolated nucleic acid molecule or a combination of isolated nucleic acid molecules of claim 1 or 2, wherein:
  (a) the antibody comprises a heavy chain variable region comprising SEQ ID NO: 6 and a light chain variable region comprising SEQ ID NO: 8;
  (b) the antibody comprises a heavy chain variable region comprising SEQ ID NO: 10 and a light chain variable region comprising SEQ ID NO: 12;
  (c) the antibody comprises a heavy chain variable region comprising SEQ ID NO: 14 and a light chain variable region comprising SEQ ID NO: 16;
  (d) the antibody comprises a heavy chain variable region comprising SEQ ID NO: 18 and a light chain variable region comprising SEQ ID NO: 20;
  (e) the antibody comprises a heavy chain variable region comprising SEQ ID NO: 22 and a light chain variable region comprising SEQ ID NO: 24; or
  (f) the antibody comprises a heavy chain variable region comprising SEQ ID NO: 26 and a light chain variable region comprising SEQ ID NO: 28.

6. The isolated nucleic acid molecule or a combination of isolated nucleic acid molecules of claim 3 or 4, wherein:
  (a) the antibody comprises a heavy chain and a light chain, wherein the heavy chain comprises SEQ ID NO: 30 and the light chain comprises SEQ ID NO: 32;
  (b) the antibody comprises a heavy chain and a light chain, wherein the heavy chain comprises SEQ ID NO: 34 and the light chain comprises SEQ ID NO: 36;
  (c) the antibody comprises a heavy chain and a light chain, wherein the heavy chain comprises SEQ ID NO: 38 and the light chain comprises SEQ ID NO: 40;
  (d) the antibody comprises a heavy chain and a light chain, wherein the heavy chain comprises SEQ ID NO: 42 and the light chain comprises SEQ ID NO: 44;
  (e) the antibody comprises a heavy chain and a light chain, wherein the heavy chain comprises SEQ ID NO: 46 and the light chain comprises SEQ ID NO: 48; or
  (f) the antibody comprises a heavy chain and a light chain, wherein the heavy chain comprises SEQ ID NO: 50 and the light chain comprises SEQ ID NO: 52.

7. An isolated nucleic acid molecule or a combination of isolated nucleic acid molecules that encodes an antibody or an antigen-binding fragment thereof that specifically binds human osteoprotegerin ligand (OPGL) wherein the antibody or an antigen-binding fragment thereof comprises:
  (a) CDR1, CDR2, and CDR3 of SEQ ID NO: 6, and CDR1, CDR2, and CDR3 of SEQ ID NO: 8;
  (b) CDR1, CDR2, and CDR3 of SEQ ID NO: 10, and CDR1, CDR2, and CDR3 of SEQ ID NO: 12;
  (c) CDR1, CDR2, and CDR3 of SEQ ID NO: 14, and CDR1, CDR2, and CDR3 of SEQ ID NO: 16;
  (d) CDR1, CDR2, and CDR3 of SEQ ID NO: 18, and CDR1, CDR2, and CDR3 of SEQ ID NO: 20;
  (e) CDR1, CDR2, and CDR3 of SEQ ID NO: 22, and CDR1, CDR2, and CDR3 of SEQ ID NO: 24; or
  (f) CDR1, CDR2, and CDR3 of SEQ ID NO: 26, and CDR1, CDR2, and CDR3 of SEQ ID NO: 28.

8. The isolated nucleic acid molecule or combination of nucleic acid molecules of claim 1, 2 or 7 wherein the antibody or antigen-binding fragment thereof specifically binds the D-E loop region of human osteoprotegerin ligand (OPGL).

9. The isolated nucleic acid molecule or combination of nucleic acid molecules of claim 1, 2 or 7 wherein the antibody or antigen-binding fragment thereof specifically binds to:
  (a) a region of human OPGL that is outside the D-E loop region; or
  (b) both a region of human OPGL that is outside the D-E loop region and all or a portion of the D-E loop region.

10. The isolated nucleic acid molecule or combination of nucleic acid molecules of claim 1, 2 or 7 wherein the antibody or antigen-binding fragment thereof inhibits binding of OPGL to an osteoclast differentiation and activation receptor (ODAR).

11. The isolated nucleic acid molecule or combination of nucleic acid molecules of claim 1, 2 or 7 wherein the antibody or antigen-binding fragment thereof is a single chain antibody or antigen-binding fragment thereof.

12. The isolated nucleic acid molecule or combination of nucleic acid molecules of claim 11 wherein the antibody or antigen-binding fragment thereof is a single-chain Fv antibody or antigen-binding fragment thereof.

13. The isolated nucleic acid molecule or combination of nucleic acid molecules of claim 1, 2 or 7 wherein the antigen-binding fragment is a Fab, Fab' or (Fab')$_2$ antibody fragment.

14. An expression vector comprising the isolated nucleic acid molecule or combination of isolated nucleic acid molecules of claim 1, 2, 3, 4 or 7.

15. An isolated host cell comprising the expression vector of claim 14.

16. The host cell of claim 15 wherein the host cell is a eukaryotic cell.

17. The host cell of claim 16 wherein the eukaryotic cell is a CHO cell.

18. A process of producing an antibody or an antigen-binding fragment thereof, comprising culturing the host cell of claim 15 under suitable conditions to express the antibody or antigen-binding fragment thereof from the culture, and optionally isolating the antibody or antigen-binding fragment thereof.

* * * * *

SEQUENCE LISTING

```
<160> NUMBER OF SEQ ID NOS: 103

<210> SEQ ID NO 1
<211> LENGTH: 1066
<212> TYPE: DNA
<213> ORGANISM: Homo sapiens

<400> SEQUENCE: 1
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tgataagtcg acatgccctg aattctgcag    1020
atatccatca cactggcggc cgctcgagca tgcatctaga gggccc                   1066

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 321
<212> TYPE: DNA
<213> ORGANISM: Homo sapiens

<400> SEQUENCE: 3
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

```
Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 5
<211> LENGTH: 348
<212> TYPE: DNA
<213> ORGANISM: Homo sapiens

<400> SEQUENCE: 5
gaggtgcagc tggtgcagtc tgggggaggc ttggtacatc ctggggggtc cctgagactc      60
tcctgtgaag gctctggatt caccttcagt agcaatggta tgcactgggt gcgccagact     120
ccaggaaaag gtctggagtg ggtatcaggt attggtactg ctggtggcac atactatgca     180
gactccgtga agggccgatt caccatttcc agagacaatg tcaagaagtc cttgtatctt     240
caaatgaaca gcctgagagc cgaggacatg gctatttatt attgtgtaag aaaaaactgg     300
ggatggttcg acccctgggg ccagggagcc ctggtcaccg tctctagt                  348

<210> SEQ ID NO 6
<211> LENGTH: 116
<212> TYPE: PRT
<213> ORGANISM: Homo sapiens

<400> SEQUENCE: 6

Glu Val Gln Leu Val Gln Ser Gly Gly Gly Leu Val His Pro Gly Gly
  1               5                  10                  15

Ser Leu Arg Leu Ser Cys Glu Gly Ser Gly Phe Thr Phe Ser Ser Asn
             20                  25                  30

Gly Met His Trp Val Arg Gln Thr Pro Gly Lys Gly Leu Glu Trp Val
         35                  40                  45

Ser Gly Ile Gly Thr Ala Gly Gly Thr Tyr Tyr Ala Asp Ser Val Lys
 50                  55                  60

Gly Arg Phe Thr Ile Ser Arg Asp Asn Val Lys Lys Ser Leu Tyr Leu
 65                  70                  75                  80

Gln Met Asn Ser Leu Arg Ala Glu Asp Met Ala Ile Tyr Tyr Cys Val
                 85                  90                  95

Arg Lys Asn Trp Gly Trp Phe Asp Pro Trp Gly Gln Gly Ala Leu Val
            100                 105                 110

Thr Val Ser Ser
        115

<210> SEQ ID NO 7
<211> LENGTH: 327
<212> TYPE: DNA
<213> ORGANISM: Homo sapiens

<400> SEQUENCE: 7
gaaattgtgc tgacccagtc tccagccacc ctgtctttgt ctccagggga aagagccacc      60
ctctcctgca gggccagtca gagtgttaac agctacttag cctggttcca acagaaacct     120
ggccaggctc ccagactcct catctatgat gcatccaaca gggccactgg catcccagcc     180
```

```
aggttcagtg gcagtgggtc tgggacagac ttcactctca ccatcagcag ccttgagcct      240
gaagattttg caatttatta ctgtcagcag cgtagcaact ggcctccgtt cacttttggc      300
caggggacca agctggagat caaacga                                          327
```

```
<210> SEQ ID NO 8
<211> LENGTH: 109
<212> TYPE: PRT
<213> ORGANISM: Homo sapiens

<400> SEQUENCE: 8
```

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Asn Ser Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Ser Asn Trp Pro Pro
                85                  90                  95

Phe Thr Phe Gly Gln Gly Thr Lys Leu Glu Ile Lys Arg
            100                 105
```

```
<210> SEQ ID NO 9
<211> LENGTH: 345
<212> TYPE: DNA
<213> ORGANISM: Homo sapiens

<400> SEQUENCE: 9
```

```
gaggtgcagc tggtgcagtc ggggggagac ttggtacatc ctgggggtc cctgagactc       60 tcctgtgtcg gctctggatt caccttcagt cactatcctt tgcactgggt tcgccaggct     120
ccaggaaaag gtctggagtg gatatcaggt attcatactg tggtggcac atactataca      180 gactccgtga agggccggtt caccatctcc agcgacaatg ccaagaactc cttatatctt     240
caaatgaaca ccctgagagc cgaggacatg gctgtgtatt actgtgcaag agggcgaaac    300
tcctttgact actggggcca gggaaccctg gtcatcgtct ctagt                     345
```

```
<210> SEQ ID NO 10
<211> LENGTH: 115
<212> TYPE: PRT
<213> ORGANISM: Homo sapiens

<400> SEQUENCE: 10
```

```
Glu Val Gln Leu Val Gln Ser Gly Gly Asp Leu Val His Pro Gly Gly
1               5                  10                  15

Ser Leu Arg Leu Ser Cys Val Gly Ser Gly Phe Thr Phe Ser His Tyr
            20                  25                  30

Pro Leu His Trp Val Arg Gln Ala Pro Gly Lys Gly Leu Glu Trp Ile
        35                  40                  45

Ser Gly Ile His Thr Gly Gly Gly Thr Tyr Tyr Thr Asp Ser Val Lys
    50                  55                  60

Gly Arg Phe Thr Ile Ser Ser Asp Asn Ala Lys Asn Ser Leu Tyr Leu
65                  70                  75                  80

Gln Met Asn Thr Leu Arg Ala Glu Asp Met Ala Val Tyr Tyr Cys Ala
```

```
                        85                  90                  95
Arg Gly Arg Asn Ser Phe Asp Tyr Trp Gly Gln Gly Thr Leu Val Ile
            100                 105                 110

Val Ser Ser
        115

<210> SEQ ID NO 11
<211> LENGTH: 324
<212> TYPE: DNA
<213> ORGANISM: Homo sapiens

<400> SEQUENCE: 11
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagtct     240
gaagattttg caacttatta ctgccaacag tataatagtt accctcccac cttcggccaa     300
gggacacgac tggagattaa acga                                            324

<210> SEQ ID NO 12
<211> LENGTH: 108
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Arg Leu Glu Ile Lys Arg
            100                 105

<210> SEQ ID NO 13
<211> LENGTH: 348
<212> TYPE: DNA
<213> ORGANISM: Homo sapiens

<400> SEQUENCE: 13
gaggtgcagc tggtgcagtc tgggggaggc ttggtacatc ctgggggtc cctgagactc       60 tcctgtgcag gctctggatt caccttcagt agctatggga tgcactgggt tcgccaggct     120
ccaggaaaag gtctggagtg ggtatcaggt attggtactg gtggtggcac atactatgca     180
gactccgtga agggccgatt caccatctcc agagacaatg tcaagaactc cttgtatctt     240
caaatgaaca gcctgagagc cgaggacatg gctgtgtatt actgtgcaag aaaaaactgg     300
ggatggtttg actactgggg ccagggaacc ctggtcaccg tctctagt                  348

<210> SEQ ID NO 14
<211> LENGTH: 116
```

<212> TYPE: PRT
<213> ORGANISM: Homo sapiens

<400> SEQUENCE: 14

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Gly Ile Gly Thr Gly Gly Thr Tyr Tyr Ala Asp Ser Val Lys
        50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Lys Asn Trp Gly Trp Phe Asp Tyr Trp Gly Gln Gly Thr Leu Val
                100                 105                 110

Thr Val Ser Ser
        115

<210> SEQ ID NO 15
<211> LENGTH: 327
<212> TYPE: DNA
<213> ORGANISM: Homo sapiens

<400> SEQUENCE: 15
gaaattgtgc tgacccagtc tccagccacc ctgtctttgt ctccagggga aagagccacc      60
ctctcctgca gggccagtca gagtattagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaaat ggcctccgta cactttggc     300 caggggacca aactcgagat caaacga                                         327

<210> SEQ ID NO 16
<211> LENGTH: 109
<212> TYPE: PRT
<213> ORGANISM: Homo sapiens

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Tyr Thr Phe Gly Gln Gly Thr Lys Leu Glu Ile Lys Arg
                100                 105

<210> SEQ ID NO 17

<211> LENGTH: 345
<212> TYPE: DNA
<213> ORGANISM: Homo sapiens

<400> SEQUENCE: 17

```
gaggtgcagc tggtgcagtc tgggggaggc ttggtacatc ctgggggtc cctgagactc      60 tcctgtgtag gctctagatt caccttcagt gcctatccta tgcactgggt tcgccaggct    120
ccaggaaaag gtctggagtg gtatcaggt attggttctg gtggtggcac aaactatgca     180
gactccgtga agggccgatt caccatctcc agagacactg ccaagaactc cttgtatctt    240
caaatgaaca gcctgagagc cgaggacatg gctgtgtatt actgtgcaag agggaggaat    300
tcttttgact actggggcca gggaaccctg gtcaccgtct ctagt                    345
```

<210> SEQ ID NO 18
<211> LENGTH: 115
<212> TYPE: PRT
<213> ORGANISM: Homo sapiens

<400> SEQUENCE: 18

```
Glu Val Gln Leu Val Gln Ser Gly Gly Gly Leu Val His Pro Gly Gly
1               5                   10                  15

Ser Leu Arg Leu Ser Cys Val Gly Ser Arg Phe Thr Phe Ser Ala Tyr
            20                  25                  30

Pro Met His Trp Val Arg Gln Ala Pro Gly Lys Gly Leu Glu Trp Val
        35                  40                  45

Ser Gly Ile Gly Ser Gly Gly Gly Thr Asn Tyr Ala Asp Ser Val Lys
    50                  55                  60

Gly Arg Phe Thr Ile Ser Arg Asp Thr Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Asn Ser Phe Asp Tyr Trp Gly Gln Gly Thr Leu Val Thr
            100                 105                 110

Val Ser Ser
        115
```

<210> SEQ ID NO 19
<211> LENGTH: 324
<212> TYPE: DNA
<213> ORGANISM: Homo sapiens

<400> SEQUENCE: 19

```
gacatccaga tgacccagtc tccatcctca ctgtctgcat ctgtaggaga cagagtcacc     60
atcacttgtc gggcgagtca gggtattagc acctggttag cctggtatca gcagaaacca   120
gagaaagccc ctaagtccct gatctatgct gcatccagtt tgcagagtgg ggtcccatcg   180
aggttcagcg gcagtggatc tgggacagat ttcactctca ccatcagcag cctgcagcct   240
gaagattttg caacttatta ctgccaacag tataatagtt accctccgac gttcggccaa   300
gggaccaagg tggagatcaa acga                                            324
```

<210> SEQ ID NO 20
<211> LENGTH: 108
<212> TYPE: PRT
<213> ORGANISM: Homo sapiens

<400> SEQUENCE: 20

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Ser Thr Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys Arg
            100                 105

<210> SEQ ID NO 21
<211> LENGTH: 348
<212> TYPE: DNA
<213> ORGANISM: Homo sapiens

<400> SEQUENCE: 21
gaggtccagc tggtgcagtc tggggaggc ttggtacatc ctgggggtc cctgagactc        60 tcctgtgcag gctctggatt caccttcagt ggccatgctt tgcactgggt cgccaggct       120 ccaggaaaag gtctggagtg gatatcaggt attggtactc atggtggac atactatgca       180 gactccgtga agggccgatt caccatctcc agagacaatg ccaagaactc cttgtttctt      240
caaatgaaca gcctgagcgc cgaggacatg gctgtgtatt actgtacaag aagaaactgg      300
ggacaatttg actactgggg ccagggaacc ctggtcaccg tctctagt                   348

<210> SEQ ID NO 22
<211> LENGTH: 116
<212> TYPE: PRT
<213> ORGANISM: Homo sapiens

<400> SEQUENCE: 22

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Gly His
            20                  25                  30

Ala Leu His Trp Val Arg Gln Ala Pro Gly Lys Gly Leu Glu Trp Val
        35                  40                  45

Ser Gly Ile Gly Thr His Gly Gly Thr Tyr Tyr Ala Asp Ser Val Lys
    50                  55                  60

Gly Arg Phe Thr Ile Ser Arg Asp Asn Ala Lys Asn Ser Leu Phe Leu
65                  70                  75                  80

Gln Met Asn Ser Leu Ser Ala Glu Asp Met Ala Val Tyr Tyr Cys Thr
                85                  90                  95

Arg Arg Asn Trp Gly Gln Phe Asp Tyr Trp Gly Gln Gly Thr Leu Val
            100                 105                 110

Thr Val Ser Ser
        115

<210> SEQ ID NO 23
<211> LENGTH: 327
<212> TYPE: DNA
<213> ORGANISM: Homo sapiens

<400> SEQUENCE: 23
gaaattgtgc tgactcagtc tccagccacc ctgtctttgt ctccagggga aagagccacc       60

```
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgta cacttttggc    300
caggggacca agctggagat caaacga                                         327
```

<210> SEQ ID NO 24
<211> LENGTH: 109
<212> TYPE: PRT
<213> ORGANISM: Homo sapiens
<400> SEQUENCE: 24

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys Arg
            100                 105
```

<210> SEQ ID NO 25
<211> LENGTH: 348
<212> TYPE: DNA
<213> ORGANISM: Homo sapiens
<400> SEQUENCE: 25

```
gaggtgcagc tggtgcagtc tgggggaggc ttggtacatc ctggggggtc cctgagactc     60
tcctgtgaag ctctggatt caccttcagt agcaatggta tgcactgggt cgccagact     120 ccaggaaaag gtctggagtg ggtatcaggt attggtactg ctggtggcac atactatgca    180
gactccgtga agggccgatt caccatttcc agagacaatg tcaagaagtc cttgtatctt    240
caaatgaaca gcctgagagc cgaggacatg gctatttatt attgtgtaag aaaagactgg    300
ggatggttcg acccctgggg ccagggagcc ctggtcaccg tctctagt              348
```

<210> SEQ ID NO 26
<211> LENGTH: 116
<212> TYPE: PRT
<213> ORGANISM: Homo sapiens
<400> SEQUENCE: 26

```
Glu Val Gln Leu Val Gln Ser Gly Gly Gly Leu Val His Pro Gly Gly
1               5                   10                  15

Ser Leu Arg Leu Ser Cys Glu Gly Ser Gly Phe Thr Phe Ser Ser Asn
            20                  25                  30

Gly Met His Trp Val Arg Gln Thr Pro Gly Lys Gly Leu Glu Trp Val
        35                  40                  45

Ser Gly Ile Gly Thr Ala Gly Gly Thr Tyr Tyr Ala Asp Ser Val Lys
    50                  55                  60
```

Gly Arg Phe Thr Ile Ser Arg Asp Asn Val Lys Lys Ser Leu Tyr Leu
65                  70                  75                  80

Gln Met Asn Ser Leu Arg Ala Glu Asp Met Ala Ile Tyr Tyr Cys Val
                85                  90                  95

Arg Lys Asp Trp Gly Trp Phe Asp Pro Trp Gly Gln Gly Ala Leu Val
            100                 105                 110

Thr Val Ser Ser
        115

<210> SEQ ID NO 27
<211> LENGTH: 327
<212> TYPE: DNA
<213> ORGANISM: Homo sapiens

<400> SEQUENCE: 27
gaaattgtgc tgacccagtc tccagccacc ctgtctttgt ctccagggga aagagccacc      60
ctctcctgca gggccagtca gagtattagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaaat ggcctccgta cacttttggc    300
caggggacca agctggagat caaacga                                         327

<210> SEQ ID NO 28
<211> LENGTH: 109
<212> TYPE: PRT
<213> ORGANISM: Homo sapiens

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Tyr Thr Phe Gly Gln Gly Thr Lys Leu Glu Ile Lys Arg
            100                 105

<210> SEQ ID NO 29
<211> LENGTH: 1414
<212> TYPE: DNA
<213> ORGANISM: Homo Sapiens

<400> SEQUENCE: 29
gaggtgcagc tggtgcagtc tgggggaggc ttggtacatc ctgggggtc cctgagactc       60
tcctgtgaag ctctggatt caccttcagt agcaatggta tgcactgggt cgccagact      120
ccaggaaaag gtctggagtg ggtatcaggt attggtactg ctggtggcac atactatgca    180
gactccgtga agggccgatt caccatttcc agagacaatg tcaagaagtc cttgtatctt    240
caaatgaaca gcctgagagc cgaggacatg gctatttatt attgtgtaag aaaaaactgg    300
ggatggttcg acccctgggg ccagggagcc ctggtcaccg tctctagtgc ctccaccaag    360

```
ggcccatcgg tcttcccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca gcccagcaa caccaaggtg gacaagaaag ttgagcccaa atcttgtgac    660
aaaactcaca catgcccacc gtgcccagca cctgaactcc tgggggggacc gtcagtcttc    720 ctcttccccc caaaacccaa ggacaccctc atgatctccc ggaccccctga ggtcacatgc    780 gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaatg ataagtcgac atgccctgaa ttctgcagat atccatcaca   1380
ctggcggccg ctcgagcatg catctagagg gccc                                1414

<210> SEQ ID NO 30
<211> LENGTH: 446
<212> TYPE: PRT
<213> ORGANISM: Homo sapiens

<400> SEQUENCE: 30

Glu Val Gln Leu Val Gln Ser Gly Gly Gly Leu Val His Pro Gly Gly
1               5                   10                  15

Ser Leu Arg Leu Ser Cys Glu Gly Ser Gly Phe Thr Phe Ser Ser Asn
            20                  25                  30

Gly Met His Trp Val Arg Gln Thr Pro Gly Lys Gly Leu Glu Trp Val
        35                  40                  45

Ser Gly Ile Gly Thr Ala Gly Gly Thr Tyr Tyr Ala Asp Ser Val Lys
    50                  55                  60

Gly Arg Phe Thr Ile Ser Arg Asp Asn Val Lys Ser Leu Tyr Leu
65                  70                  75                  80

Gln Met Asn Ser Leu Arg Ala Glu Asp Met Ala Ile Tyr Tyr Cys Val
                85                  90                  95

Arg Lys Asn Trp Gly Trp Phe Asp Pro Trp Gly Gln Gly Ala Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
        210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 31
<211> LENGTH: 648
<212> TYPE: DNA
<213> ORGANISM: Homo Sapiens

<400> SEQUENCE: 31
gaaattgtgc tgacccagtc tccagccacc ctgtctttgt ctccagggga aagagccacc      60
ctctcctgca gggccagtca gagtgttaac agctacttag cctggttcca acagaaacct     120
ggccaggctc ccagactcct catctatgat gcatccaaca gggccactgg catcccagcc     180
aggttcagtg gcagtgggtc tgggacagac ttcactctca ccatcagcag ccttgagcct     240
gaagattttg caatttatta ctgtcagcag cgtagcaact ggcctccgtt cactttggc      300
caggggacca agctggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttag                 648
```

<210> SEQ ID NO 32
<211> LENGTH: 215
<212> TYPE: PRT
<213> ORGANISM: Homo sapiens

<400> SEQUENCE: 32

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Ser Asn Trp Pro Pro
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 33
<211> LENGTH: 1411
<212> TYPE: DNA
<213> ORGANISM: Homo Sapiens

<400> SEQUENCE: 33

```
gaggtgcagc tggtgcagtc ggggggagac ttggtacatc ctgggggtc cctgagactc      60 tcctgtgtcg gctctggatt caccttcagt cactatcctt tgcactgggt tcgccaggct    120
ccaggaaaag gtctggagtg gatatcaggt attcatactg gtggtggcac atactataca    180
gactccgtga agggccggtt caccatctcc agcgacaatg ccaagaactc cttatatctt    240
caaatgaaca ccctgagagc cgaggacatg gctgtgtatt actgtgcaag agggcgaaac    300
tcctttgact actggggcca gggaaccctg gtcatcgtct ctagtgcctc caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaactcctgg ggggaccgtc agtcttcctc    720
```

```
ttcccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac cacaggtgta caccctgccc ccatcccggg atgagctgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatgata agtcgacatg ccctgaattc tgcagatatc catcacactg   1380
gcggccgctc gagcatgcat ctagagggcc c                                 1411
```

<210> SEQ ID NO 34
<211> LENGTH: 445
<212> TYPE: PRT
<213> ORGANISM: Homo sapiens

<400> SEQUENCE: 34

```
Glu Val Gln Leu Val Gln Ser Gly Gly Asp Leu Val His Pro Gly Gly
1               5                   10                  15

Ser Leu Arg Leu Ser Cys Val Gly Ser Gly Phe Thr Phe Ser His Tyr
            20                  25                  30

Pro Leu His Trp Val Arg Gln Ala Pro Gly Lys Gly Leu Glu Trp Ile
        35                  40                  45

Ser Gly Ile His Thr Gly Gly Thr Tyr Tyr Thr Asp Ser Val Lys
    50                  55                  60

Gly Arg Phe Thr Ile Ser Ser Asp Asn Ala Lys Asn Ser Leu Tyr Leu
65                  70                  75                  80

Gln Met Asn Thr Leu Arg Ala Glu Asp Met Ala Val Tyr Tyr Cys Ala
                85                  90                  95

Arg Gly Arg Asn Ser Phe Asp Tyr Trp Gly Gln Gly Thr Leu Val Ile
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 35
<211> LENGTH: 645
<212> TYPE: DNA
<213> ORGANISM: Homo Sapiens

<400> SEQUENCE: 35
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagtct     240
gaagattttg caacttatta ctgccaacag tataatagtt accctcccac cttcggccaa     300
gggacacgac tggagattaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 36
<211> LENGTH: 214
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

```
Leu Ala Trp Tyr Gln Gln Lys Pro Glu Lys Ala Pro Lys Ser Leu Ile
        35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Ser
 65                  70                  75                  80
Glu Asp Phe Ala Thr Tyr Tyr Cys Gln Gln Tyr Asn Ser Tyr Pro Pro
                 85                  90                  95
Thr Phe Gly Gln Gly Thr Arg Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 37
<211> LENGTH: 1414
<212> TYPE: DNA
<213> ORGANISM: Homo Sapiens

<400> SEQUENCE: 37
gaggtgcagc tggtgcagtc tgggggaggc ttggtacatc ctgggggtc cctgagactc      60
tcctgtgcag gctctggatt caccttcagt agctatggga tgcactgggt tcgccaggct    120
ccaggaaaag gtctggagtg ggtatcaggt attggtactg gtggtggcac atactatgca    180
gactccgtga agggccgatt caccatctcc agagacaatg tcaagaactc cttgtatctt    240
caaatgaaca gcctgagagc cgaggacatg gctgtgtatt actgtgcaag aaaaaactgg    300
ggatggtttg actactgggg ccagggaacc ctggtcaccg tctctagtgc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggatgagct gaccaagaac   1080
```

```
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctatag caagctcacc gtggacaaga gcaggtggca gcagggggaac   1260 gtcttctcat gctccgtgat gcatgaggct ctgcacaacc actacacgca gaagagcctc    1320
tccctgtctc cgggtaaatg ataagtcgac atgccctgaa ttctgcagat atccatcaca    1380
ctggcggccg ctcgagcatg catctagagg gccc                                1414

<210> SEQ ID NO 38
<211> LENGTH: 446
<212> TYPE: PRT
<213> ORGANISM: Homo sapiens

<400> SEQUENCE: 38

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Gly Ile Gly Thr Gly Gly Thr Tyr Tyr Ala Asp Ser Val Lys
    50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Lys Asn Trp Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 39
<211> LENGTH: 648
<212> TYPE: DNA
<213> ORGANISM: Homo Sapiens

<400> SEQUENCE: 39
gaaattgtgc tgacccagtc tccagccacc ctgtctttgt ctccagggga agagccacc      60 ctctcctgca gggccagtca gagtattagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaaat ggcctccgta cactttggc    300 caggggacca aactcgagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct cagcctcag cagcaccctg     540 acgctgagca agcagactac gagaaacac aaagtctacg cctgcgaagt cacccatcag    600
ggcctgagct cgcccgtcac aaagagcttc aacaggggag agtgttag               648

<210> SEQ ID NO 40
<211> LENGTH: 215
<212> TYPE: PRT
<213> ORGANISM: Homo sapiens

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95
```

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 41
<211> LENGTH: 1411
<212> TYPE: DNA
<213> ORGANISM: Homo Sapiens

<400> SEQUENCE: 41
gaggtgcagc tggtgcagtc tgggggaggc ttggtacatc ctggggggtc cctgagactc      60
tcctgtgtag gctctagatt caccttcagt gcctatccta tgcactgggt tcgccaggct     120
ccaggaaaag gtctggagtg ggtatcaggt attggttctg gtggtggcac aaactatgca     180
gactccgtga agggccgatt caccatctcc agagacactg ccaagaactc cttgtatctt     240
caaatgaaca gcctgagagc cgaggacatg gctgtgtatt actgtgcaag agggaggaat     300
tcttttgact actggggcca gggaaccctg gtcaccgtct ctagtgcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca agccctcccc agcccccatc gagaaaacca tctccaaagc caaagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaatgata agtcgacatg ccctgaattc tgcagatatc catcacactg    1380
gcggccgctc gagcatgcat ctagagggcc c                                    1411

<210> SEQ ID NO 42
<211> LENGTH: 445
<212> TYPE: PRT
<213> ORGANISM: Homo sapiens

<400> SEQUENCE: 42

```
Glu Val Gln Leu Val Gln Ser Gly Gly Gly Leu Val His Pro Gly
1               5                   10                  15

Ser Leu Arg Leu Ser Cys Val Gly Ser Arg Phe Thr Phe Ser Ala Tyr
            20                  25                  30

Pro Met His Trp Val Arg Gln Ala Pro Gly Lys Gly Leu Glu Trp Val
        35                  40                  45

Ser Gly Ile Gly Ser Gly Gly Thr Asn Tyr Ala Asp Ser Val Lys
50                  55                  60

Gly Arg Phe Thr Ile Ser Arg Asp Thr Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Asn Ser Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 43
<211> LENGTH: 645
<212> TYPE: DNA
<213> ORGANISM: Homo Sapiens

<400> SEQUENCE: 43
gacatccaga tgacccagtc tccatcctca ctgtctgcat ctgtaggaga cagagtcacc      60
atcacttgtc gggcgagtca gggtattagc acctggttag cctggtatca gcagaaacca     120
gagaaagccc ctaagtccct gatctatgct gcatccagtt tgcagagtgg ggtcccatcg     180
aggttcagcg gcagtggatc tgggacagat ttcactctca ccatcagcag cctgcagcct     240
gaagattttg caacttatta ctgccaacag tataatagtt accctccgac gttcggccaa     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc      600
ctgagctcgc ccgtcacaaa gagcttcaac aggggagagt gttag                     645

<210> SEQ ID NO 44
<211> LENGTH: 214
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
              165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 1414
<212> TYPE: DNA
<213> ORGANISM: Homo Sapiens

<400> SEQUENCE: 45
gaggtccagc tggtgcagtc tgggggaggc ttggtacatc ctggggggtc cctgagactc      60
tcctgtgcag gctctggatt caccttcagt ggccatgctt tgcactgggt tcgccaggct     120
ccaggaaaag gtctggagtg ggtatcaggt attggtactc atggtgggac atactatgca     180
gactccgtga agggccgatt caccatctcc agagacaatg ccaagaactc cttgtttctt     240
caaatgaaca gcctgagcgc cgaggacatg gctgtgtatt actgtacaag aagaaactgg     300
ggacaatttg actactgggg ccagggaacc ctggtcaccg tctctagtgc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc tcccgtgct ggactccgac    1200 ggctccttct tcctctatag caagctcacc gtggacaaga gcaggtggca gcagggaac     1260 gtcttctcat gctccgtgat gcatgaggct ctgcacaacc actacacgca gaagagcctc    1320
tccctgtctc cgggtaaatg ataagtcgac atgccctgaa ttctgcagat atccatcaca    1380
ctggcggccg ctcgagcatg catctagagg gccc                                1414

<210> SEQ ID NO 46
<211> LENGTH: 446
<212> TYPE: PRT
<213> ORGANISM: Homo sapiens

<400> SEQUENCE: 46

Glu Val Gln Leu Val Gln Ser Gly Gly Gly Leu Val His Pro Gly Gly
1               5                   10                  15

-continued

Ser Leu Arg Leu Ser Cys Ala Gly Ser Gly Phe Thr Phe Ser Gly His
            20              25              30

Ala Leu His Trp Val Arg Gln Ala Pro Gly Lys Gly Leu Glu Trp Val
        35              40              45

Ser Gly Ile Gly Thr His Gly Gly Thr Tyr Tyr Ala Asp Ser Val Lys
    50              55              60

Gly Arg Phe Thr Ile Ser Arg Asp Asn Ala Lys Asn Ser Leu Phe Leu
65              70              75              80

Gln Met Asn Ser Leu Ser Ala Glu Asp Met Ala Val Tyr Tyr Cys Thr
                85              90              95

Arg Arg Asn Trp Gly Gln Phe Asp Tyr Trp Gly Gln Gly Thr Leu Val
            100             105             110

Thr Val Ser Ser Ala Ser Thr Lys Gly Pro Ser Val Phe Pro Leu Ala
        115             120             125

Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
                165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
        195             200             205

Lys Val Asp Lys Lys Val Glu Pro Lys Ser Cys Asp Lys Thr His Thr
    210             215             220

Cys Pro Pro Cys Pro Ala Pro Glu Leu Leu Gly Gly Pro Ser Val Phe
225             230             235             240

Leu Phe Pro Pro Lys Pro Lys Asp Thr Leu Met Ile Ser Arg Thr Pro
                245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
        275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
                325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
        355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
                405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
        435             440             445

<210> SEQ ID NO 47
<211> LENGTH: 648
<212> TYPE: DNA
<213> ORGANISM: Homo Sapiens

<400> SEQUENCE: 47

```
gaaattgtgc tgactcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgta cacttttggc   300
caggggacca agctggagat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagacta cgagaaacac aaagtctacg cctgcgaagt cacccatcag   600
ggcctgagct cgcccgtcac aaagagcttc aacaggggag agtgttag              648
```

<210> SEQ ID NO 48
<211> LENGTH: 215
<212> TYPE: PRT
<213> ORGANISM: Homo sapiens

<400> SEQUENCE: 48

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 49
<211> LENGTH: 1414
<212> TYPE: DNA
<213> ORGANISM: Homo Sapiens

<400> SEQUENCE: 49

```
gaggtgcagc tggtgcagtc tgggggaggc ttggtacatc ctgggggtc cctgagactc      60
tcctgtgaag gctctggatt caccttcagt agcaatggta tgcactgggt gcgccagact     120
ccaggaaaag gtctggagtg ggtatcaggt attggtactg ctggtggcac atactatgca     180
gactccgtga agggccgatt caccatttcc agagacaatg tcaagaagtc cttgtatctt     240
caaatgaaca gcctgagagc cgaggacatg gctatttatt attgtgtaag aaaagactgg     300
ggatggttcg accccctgggg ccaggagcc ctggtcaccg tctctagtgc ctccaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctatag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaatg ataagtcgac atgccctgaa ttctgcagat atccatcaca    1380
ctggcggccg ctcgagcatg catctagagg gccc                                1414
```

<210> SEQ ID NO 50
<211> LENGTH: 446
<212> TYPE: PRT
<213> ORGANISM: Homo sapiens

<400> SEQUENCE: 50

```
Glu Val Gln Leu Val Gln Ser Gly Gly Gly Leu Val His Pro Gly Gly
1               5                   10                  15

Ser Leu Arg Leu Ser Cys Glu Gly Ser Gly Phe Thr Phe Ser Ser Asn
            20                  25                  30

Gly Met His Trp Val Arg Gln Thr Pro Gly Lys Gly Leu Glu Trp Val
        35                  40                  45

Ser Gly Ile Gly Thr Ala Gly Gly Thr Tyr Tyr Ala Asp Ser Val Lys
    50                  55                  60

Gly Arg Phe Thr Ile Ser Arg Asp Asn Val Lys Lys Ser Leu Tyr Leu
65                  70                  75                  80
```

```
Gln Met Asn Ser Leu Arg Ala Glu Asp Met Ala Ile Tyr Tyr Cys Val
                 85                  90                  95
Arg Lys Asp Trp Gly Trp Phe Asp Pro Trp Gly Gln Gly Ala Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 51
<211> LENGTH: 648
<212> TYPE: DNA
<213> ORGANISM: Homo Sapiens

<400> SEQUENCE: 51
gaaattgtgc tgacccagtc tccagccacc ctgtctttgt ctccagggga aagagccacc     60
ctctcctgca gggccagtca gagtattagc agctacttag cctggtacca acagaaacct    120
```

```
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaaat ggcctccgta cacttttggc      300
caggggacca agctggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgttag               648
```

```
<210> SEQ ID NO 52
<211> LENGTH: 215
<212> TYPE: PRT
<213> ORGANISM: Homo sapiens

<400> SEQUENCE: 52
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 53
<211> LENGTH: 24
<212> TYPE: DNA
<213> ORGANISM: Artificial
<220> FEATURE:
<223> OTHER INFORMATION: oligonucleotide primer for PCR
<220> FEATURE:
<221> NAME/KEY: misc_feature
<222> LOCATION: (18)..(23)
<223> OTHER INFORMATION: n is a, c, t, or g
```

<400> SEQUENCE: 53
ggccggatag gcctcacnnn nnnt                                    24

<210> SEQ ID NO 54
<211> LENGTH: 26
<212> TYPE: DNA
<213> ORGANISM: Artificial
<220> FEATURE:
<223> OTHER INFORMATION: oligonucleotide primer for PCR

<400> SEQUENCE: 54
ggacactgac atggactgaa ggagta                                  26

<210> SEQ ID NO 55
<211> LENGTH: 21
<212> TYPE: DNA
<213> ORGANISM: Artificial
<220> FEATURE:
<223> OTHER INFORMATION: oligonucleotide primer PCR

<400> SEQUENCE: 55
ggggtcaggc tggaactgag g                                       21

<210> SEQ ID NO 56
<211> LENGTH: 54
<212> TYPE: DNA
<213> ORGANISM: Artificial
<220> FEATURE:
<223> OTHER INFORMATION: oligonucleotide primer for PCR

<400> SEQUENCE: 56
cagcagaagc ttctagacca ccatggacat gagggtgccc gctcagctcc tggg   54

<210> SEQ ID NO 57
<211> LENGTH: 48
<212> TYPE: DNA
<213> ORGANISM: Artificial
<220> FEATURE:
<223> OTHER INFORMATION: oligonucleotide primer for PCR

<400> SEQUENCE: 57
ccgctcagct cctggggctc ctgctgctgt ggctgagagg tgccagat          48

<210> SEQ ID NO 58
<211> LENGTH: 65
<212> TYPE: DNA
<213> ORGANISM: Artificial
<220> FEATURE:
<223> OTHER INFORMATION: oligonucleotide primer for PCR

<400> SEQUENCE: 58
gtggttgaga ggtgccagat gtgaaattgt gctgacccag tctccagcca ccctgtcttt   60
gtctc                                                              65

<210> SEQ ID NO 59
<211> LENGTH: 34
<212> TYPE: DNA
<213> ORGANISM: Artificial
<220> FEATURE:
<223> OTHER INFORMATION: oligonucleotide primer for PCR

<400> SEQUENCE: 59
cttgtcgact caaacactctc ccctgttgaa gctc                        34

```
<210> SEQ ID NO 60
<211> LENGTH: 22
<212> TYPE: PRT
<213> ORGANISM: Artificial
<220> FEATURE:
<223> OTHER INFORMATION: signal sequence for mammalian expression

<400> SEQUENCE: 60

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 61
<211> LENGTH: 20
<212> TYPE: DNA
<213> ORGANISM: Artificial
<220> FEATURE:
<223> OTHER INFORMATION: oligonucleotide primer for PCR

<400> SEQUENCE: 61
saggtscagy tkgtgsagtc                                         20

<210> SEQ ID NO 62
<211> LENGTH: 17
<212> TYPE: DNA
<213> ORGANISM: Artificial
<220> FEATURE:
<223> OTHER INFORMATION: oligonucleotide primer for PCR

<400> SEQUENCE: 62
ctgagttcca cgacacc                                            17

<210> SEQ ID NO 63
<211> LENGTH: 54
<212> TYPE: DNA
<213> ORGANISM: Artificial
<220> FEATURE:
<223> OTHER INFORMATION: oligonucleotide primer for PCR

<400> SEQUENCE: 63
cagcagaagc ttctagacca ccatggacat gagggtgccc gctcagctcc tggg    54

<210> SEQ ID NO 64
<211> LENGTH: 48
<212> TYPE: DNA
<213> ORGANISM: Artificial
<220> FEATURE:
<223> OTHER INFORMATION: oligonucleotide primer for PCR

<400> SEQUENCE: 64
ccgctcagct cctggggctc ctgctgctgt ggctgagagg tgccagat          48

<210> SEQ ID NO 65
<211> LENGTH: 43
<212> TYPE: DNA
<213> ORGANISM: Artificial
<220> FEATURE:
<223> OTHER INFORMATION: oligonucleotide primer for PCR

<400> SEQUENCE: 65
gtggttgaga ggtgccagat gtgaggtgca gctggtgcag tct               43

<210> SEQ ID NO 66
<211> LENGTH: 50
<212> TYPE: DNA
<213> ORGANISM: Artificial
```

```
<220> FEATURE:
<223> OTHER INFORMATION: oligonucleotide primer for PCR

<400> SEQUENCE: 66
gtggaggcac tagagacggt gaccagggct ccctggcccc aggggtcgaa      50

<210> SEQ ID NO 67
<211> LENGTH: 1409
<212> TYPE: DNA
<213> ORGANISM: Homo sapiens

<400> SEQUENCE: 67
tctagaccac catggacatc aggctcagct tagttttcct tgtccttttc ataaaaggtg      60
tccagtgtga ggtagaactg gtggagtctg ggggcggctt agtacaacct ggaaggtcca     120
tgacactctc ctgtgcagcc tcgggattca ctttcagaac ctatggcatg gcctgggtcc     180
gccaggcccc aacgaagggt ctggagtggg tctcatcaat tactgctagt ggtggtacca     240
cctactatcg agactccgtg aagggccgct tcactatttt tagggataat gcaaaaagta     300
ccctatacct gcagatggac agtccgaggt ctgaggacac ggccacttat ttctgtacat     360
caatttcgga atactggggc cacggagtca tggtcaccgt ctctagtgcc tccaccaagg     420
gcccatcggt cttccccctg gcaccctcct ccaagagcac ctctgggggc acagcggccc     480
tgggctgcct ggtcaaggac tacttccccg aaccggtgac ggtgtcgtgg aactcaggcg     540
ccctgaccag cggcgtgcac accttcccgg ctgtcctaca gtcctcagga ctctactccc     600
tcagcagcgt ggtgaccgtg ccctccagca gcttgggcac ccagacctac atctgcaacg     660
tgaatcacaa gcccagcaac accaaggtgg acaagaaagt tgagcccaaa tcttgtgaca     720
aaactcacac atgcccaccg tgcccagcac ctgaactcct ggggggaccg tcagtcttcc     780
tcttcccccc aaaacccaag gacaccctca tgatctcccg gacccctgag gtcacatgcg     840
tggtggtgga cgtgagccac gaagaccctg aggtcaagtt caactggtac gtggacggcg     900
tggaggtgca taatgccaag acaaagccgc gggaggagca gtacaacagc acgtaccgtg     960
tggtcagcgt cctcaccgtc ctgcaccagg actggctgaa tggcaaggag tacaagtgca    1020
aggtctccaa caaagccctc ccagccccca tcgagaaaac catctccaaa gccaagggc    1080 agccccgaga accacaggtg tacaccctgc cccatcccg ggatgagctg accaagaacc    1140
aggtcagcct gacctgcctg gtcaaaggct tctatcccag cgacatcgcc gtggagtggg    1200
agagcaatgg gcagccggag aacaactaca gaccacgcc tcccgtgctg gactccgacg    1260
gctccttctt cctctatagc aagctcaccg tggacaagag caggtggcag caggggaacg    1320
tcttctcatg ctccgtgatg catgaggctc tgcacaacca ctacacgcag aagagcctct    1380
ccctgtctcc gggtaaatga taagtcgac                                      1409

<210> SEQ ID NO 68
<211> LENGTH: 5
<212> TYPE: PRT
<213> ORGANISM: Mus musculus

<400> SEQUENCE: 68

Ser Val Pro Thr Asp
1               5

<210> SEQ ID NO 69
<211> LENGTH: 5
<212> TYPE: PRT
<213> ORGANISM: Homo sapiens
```

```
<400> SEQUENCE: 69

Asp Leu Ala Thr Glu
1               5

<210> SEQ ID NO 70
<211> LENGTH: 50
<212> TYPE: PRT
<213> ORGANISM: Mus musculus

<400> SEQUENCE: 70

Thr Leu Ser Asn Gly Lys Leu Arg Val Asn Gln Asp Gly Phe Tyr Tyr
1               5                   10                  15

Leu Tyr Ala Asn Ile Cys Phe Arg His His Glu Thr Ser Gly Ser Val
            20                  25                  30

Pro Thr Asp Tyr Leu Gln Leu Met Val Tyr Val Val Lys Thr Ser Ile
        35                  40                  45

Lys Ile
    50

<210> SEQ ID NO 71
<211> LENGTH: 50
<212> TYPE: PRT
<213> ORGANISM: Homo sapiens

<400> SEQUENCE: 71

Thr Leu Ser Asn Gly Lys Leu Ile Val Asn Gln Asp Gly Phe Tyr Tyr
1               5                   10                  15

Leu Tyr Ala Asn Ile Cys Phe Arg His His Glu Thr Ser Gly Asp Leu
            20                  25                  30

Ala Thr Glu Tyr Leu Gln Leu Met Val Tyr Val Thr Lys Thr Ser Ile
        35                  40                  45

Lys Ile
    50

<210> SEQ ID NO 72
<211> LENGTH: 50
<212> TYPE: PRT
<213> ORGANISM: Artificial
<220> FEATURE:
<223> OTHER INFORMATION: murine DE variant amino acid sequence

<400> SEQUENCE: 72

Thr Leu Ser Asn Gly Lys Leu Arg Val Asn Gln Asp Gly Phe Tyr Tyr
1               5                   10                  15

Leu Tyr Ala Asn Ile Cys Phe Arg His His Glu Thr Ser Gly Asp Leu
            20                  25                  30

Ala Thr Glu Tyr Leu Gln Leu Met Val Tyr Val Val Lys Thr Ser Ile
        35                  40                  45

Lys Ile
    50

<210> SEQ ID NO 73
<211> LENGTH: 23
<212> TYPE: DNA
<213> ORGANISM: Artificial
<220> FEATURE:
<223> OTHER INFORMATION: oligonucleotide primer for PCR

<400> SEQUENCE: 73
cctctcatat ggactacaag gac                                           23
```

```
<210> SEQ ID NO 74
<211> LENGTH: 30
<212> TYPE: DNA
<213> ORGANISM: Artificial
<220> FEATURE:
<223> OTHER INFORMATION: oligonucleotide primer for PCR

<400> SEQUENCE: 74
agtagccagg tctcccgatg tttcatgatg                                    30

<210> SEQ ID NO 75
<211> LENGTH: 30
<212> TYPE: DNA
<213> ORGANISM: Artificial
<220> FEATURE:
<223> OTHER INFORMATION: oligonucleotide primer for PCR

<400> SEQUENCE: 75
ctggctactg aatatcttca gctgatggtg                                    30

<210> SEQ ID NO 76
<211> LENGTH: 25
<212> TYPE: DNA
<213> ORGANISM: Artificial
<220> FEATURE:
<223> OTHER INFORMATION: oligonucleotide primer for PCR

<400> SEQUENCE: 76
cctctcctcg agttagtcta tgtcc                                         25

<210> SEQ ID NO 77
<211> LENGTH: 5
<212> TYPE: PRT
<213> ORGANISM: Homo sapiens

<400> SEQUENCE: 77

Gly His Ala Leu His
1               5

<210> SEQ ID NO 78
<211> LENGTH: 16
<212> TYPE: PRT
<213> ORGANISM: Homo sapiens

<400> SEQUENCE: 78

Gly Ile Gly Thr His Gly Gly Thr Tyr Tyr Ala Asp Ser Val Lys Gly
1               5                   10                  15

<210> SEQ ID NO 79
<211> LENGTH: 8
<212> TYPE: PRT
<213> ORGANISM: Homo sapiens

<400> SEQUENCE: 79

Arg Asn Trp Gly Gln Phe Asp Tyr
1               5

<210> SEQ ID NO 80
<211> LENGTH: 5
<212> TYPE: PRT
<213> ORGANISM: Homo sapiens

<400> SEQUENCE: 80

His Tyr Pro Leu His
1               5
```

```
<210> SEQ ID NO 81
<211> LENGTH: 16
<212> TYPE: PRT
<213> ORGANISM: Homo sapiens

<400> SEQUENCE: 81

Gly Ile His Thr Gly Gly Gly Thr Tyr Tyr Thr Asp Ser Val Lys Gly
1               5                   10                  15

<210> SEQ ID NO 82
<211> LENGTH: 7
<212> TYPE: PRT
<213> ORGANISM: Homo sapiens

<400> SEQUENCE: 82

Gly Arg Asn Ser Phe Asp Tyr
1               5

<210> SEQ ID NO 83
<211> LENGTH: 5
<212> TYPE: PRT
<213> ORGANISM: Homo sapiens

<400> SEQUENCE: 83

Ala Tyr Pro Met His
1               5

<210> SEQ ID NO 84
<211> LENGTH: 16
<212> TYPE: PRT
<213> ORGANISM: Homo sapiens

<400> SEQUENCE: 84

Gly Ile Gly Ser Gly Gly Gly Thr Asn Tyr Ala Asp Ser Val Lys Gly
1               5                   10                  15

<210> SEQ ID NO 85
<211> LENGTH: 5
<212> TYPE: PRT
<213> ORGANISM: Homo sapiens

<400> SEQUENCE: 85

Ser Tyr Gly Met His
1               5

<210> SEQ ID NO 86
<211> LENGTH: 16
<212> TYPE: PRT
<213> ORGANISM: Homo sapiens

<400> SEQUENCE: 86

Gly Ile Gly Thr Gly Gly Gly Thr Tyr Tyr Ala Asp Ser Val Lys Gly
1               5                   10                  15

<210> SEQ ID NO 87
<211> LENGTH: 8
<212> TYPE: PRT
<213> ORGANISM: Homo sapiens

<400> SEQUENCE: 87

Lys Asn Trp Gly Trp Phe Asp Tyr
1               5

<210> SEQ ID NO 88
<211> LENGTH: 5
<212> TYPE: PRT
```

<213> ORGANISM: Homo sapiens

<400> SEQUENCE: 88

Ser Asn Gly Met His
1               5

<210> SEQ ID NO 89
<211> LENGTH: 16
<212> TYPE: PRT
<213> ORGANISM: Homo sapiens

<400> SEQUENCE: 89

Gly Ile Gly Thr Ala Gly Gly Thr Tyr Tyr Ala Asp Ser Val Lys Gly
1               5                   10                  15

<210> SEQ ID NO 90
<211> LENGTH: 8
<212> TYPE: PRT
<213> ORGANISM: Homo sapiens

<400> SEQUENCE: 90

Lys Asn Trp Gly Trp Phe Asp Pro
1               5

<210> SEQ ID NO 91
<211> LENGTH: 8
<212> TYPE: PRT
<213> ORGANISM: Homo sapiens

<400> SEQUENCE: 91

Lys Asp Trp Gly Trp Phe Asp Pro
1               5

<210> SEQ ID NO 92
<211> LENGTH: 11
<212> TYPE: PRT
<213> ORGANISM: Homo sapiens

<400> SEQUENCE: 92

Arg Ala Ser Gln Gly Ile Ser Ser Trp Leu Ala
1               5                   10

<210> SEQ ID NO 93
<211> LENGTH: 7
<212> TYPE: PRT
<213> ORGANISM: Homo sapiens

<400> SEQUENCE: 93

Ala Ala Ser Ser Leu Gln Ser
1               5

<210> SEQ ID NO 94
<211> LENGTH: 9
<212> TYPE: PRT
<213> ORGANISM: Homo sapiens

<400> SEQUENCE: 94

Gln Gln Tyr Asn Ser Tyr Pro Pro Thr
1               5

<210> SEQ ID NO 95
<211> LENGTH: 11
<212> TYPE: PRT
<213> ORGANISM: Homo sapiens

<400> SEQUENCE: 95

```
Arg Ala Ser Gln Gly Ile Ser Thr Trp Leu Ala
1               5                   10

<210> SEQ ID NO 96
<211> LENGTH: 11
<212> TYPE: PRT
<213> ORGANISM: Homo sapiens

<400> SEQUENCE: 96

Arg Ala Ser Gln Ser Ile Ser Ser Tyr Leu Ala
1               5                   10

<210> SEQ ID NO 97
<211> LENGTH: 7
<212> TYPE: PRT
<213> ORGANISM: Homo sapiens

<400> SEQUENCE: 97

Asp Ala Ser Asn Arg Ala Thr
1               5

<210> SEQ ID NO 98
<211> LENGTH: 10
<212> TYPE: PRT
<213> ORGANISM: Homo sapiens

<400> SEQUENCE: 98

Gln Gln Arg Ser Lys Trp Pro Pro Tyr Thr
1               5                   10

<210> SEQ ID NO 99
<211> LENGTH: 11
<212> TYPE: PRT
<213> ORGANISM: Homo sapiens

<400> SEQUENCE: 99

Arg Ala Ser Gln Ser Val Asn Ser Tyr Leu Ala
1               5                   10

<210> SEQ ID NO 100
<211> LENGTH: 10
<212> TYPE: PRT
<213> ORGANISM: Homo sapiens

<400> SEQUENCE: 100

Gln Gln Arg Ser Asn Trp Pro Pro Phe Thr
1               5                   10

<210> SEQ ID NO 101
<211> LENGTH: 11
<212> TYPE: PRT
<213> ORGANISM: Homo sapiens

<400> SEQUENCE: 101

Arg Ala Ser Gln Ser Val Ser Ser Tyr Leu Ala
1               5                   10

<210> SEQ ID NO 102
<211> LENGTH: 10
<212> TYPE: PRT
<213> ORGANISM: Homo sapiens

<400> SEQUENCE: 102

Gln Gln Arg Ser Asn Trp Pro Pro Tyr Thr
1               5                   10
```

```
<210> SEQ ID NO 103
<211> LENGTH: 5
<212> TYPE: PRT
<213> ORGANISM: Homo sapiens

<400> SEQUENCE: 103

Asp Leu Ala Thr Glu
1               5
```